United States Patent [19]
Mitch et al.

[11] Patent Number: 5,998,434
[45] Date of Patent: Dec. 7, 1999

[54] COMPOSITION FOR TREATING PAIN

[75] Inventors: Charles H. Mitch, Columbus; Harlan E. Shannon, Carmel, both of Ind.

[73] Assignee: Eli Lilly and Company, Indianapolis, Ind.

[21] Appl. No.: 09/091,143

[22] PCT Filed: Dec. 5, 1996

[86] PCT No.: PCT/US96/19229

§ 371 Date: Jun. 4, 1998

§ 102(e) Date: Jun. 4, 1998

[87] PCT Pub. No.: WO97/20819

PCT Pub. Date: Jun. 12, 1997

Related U.S. Application Data

[60] Provisional application No. 60/009,510, Dec. 6, 1995, provisional application No. 60/008,276, Dec. 6, 1995, provisional application No. 60/008,279, Dec. 6, 1995, provisional application No. 60/008,273, Dec. 6, 1995, provisional application No. 60/008,280, Dec. 6, 1995, provisional application No. 60/008,270, Dec. 6, 1995, provisional application No. 60/008,274, Dec. 6, 1995, and provisional application No. 60/008,275, Dec. 6, 1995.

[51] Int. Cl.⁶ .............. A61K 31/41; A61K 31/55

[52] U.S. Cl. .............. 514/305; 514/326; 514/364; 514/299; 514/252; 514/253; 514/214

[58] Field of Search ............... 514/305, 326, 514/364, 299, 252, 253, 214

[56] References Cited

U.S. PATENT DOCUMENTS

| | | | |
|---|---|---|---|
| 4,929,625 | 5/1990 | Cliffe | 514/304 |
| 5,043,345 | 8/1991 | Sauerberg et al. | 514/342 |
| 5,082,843 | 1/1992 | Cliffe | 514/253 |
| 5,512,574 | 4/1996 | Husbands et al. | 514/253 |
| 5,527,813 | 6/1996 | Sauerberg et al. | 514/361 |
| 5,605,908 | 2/1997 | Merritt et al. | 514/305 |

*Primary Examiner*—James H. Reamer
*Attorney, Agent, or Firm*—David M. Stemerick; Arleen Palmberg; MaCharri Vorndran-Jones

[57] ABSTRACT

The present invention provides a composition and method for treating pain using Selected Muscarinic Compounds and one or more compounds selected from the group consisting of Nonsteroidal Anti-inflammatory drugs, acetaminophen, opioids, and alpha-adrenergic compounds.

41 Claims, No Drawings

COMPOSITION FOR TREATING PAIN

This application is a continuation of provisional applications:

U.S. Ser. No. 60/009,510 Dec. 6, 1995
U.S. Ser. No. 60/008,276 Dec. 6, 1995
U.S. Ser. No. 60/008,279 Dec. 6, 1995
U.S. Ser. No. 60/008,273 Dec. 6, 1995
U.S. Ser. No. 60/008,280 Dec. 6, 1995
U.S. Ser. No. 60/008,270 Dec. 6, 1995
U.S. Ser. No. 60/008,274 Dec. 6, 1995
U.S. Ser. No. 60/008,275 Dec. 6, 1995

The present invention relates to a method for using a combination of compounds for treating pain.

This invention relates to a therapeutic combination of compounds to provide analgesic activity.

More active analgesic combinations effects are in constant demand because they offer the attractive possibility of relieving pain with reduced dosages, thereby diminishing the expected side effects and toxicity that would otherwise result from higher dosages. It would be particularly desirable to acquire a synergistic combination effect. Such a composition is the subject of the present invention.

The composition of this invention provides a surprising synergistically effective treatment for pain using compounds which are independently known in the art. The synergistic effect of the present composition provides a means for treating pain using a lower dosage of each compound in the composition, thus providing a treatment with a more desirable side effect profile.

The present invention provides a composition useful for the treatment of pain, comprising a First Compound selected from the group consisting of:

Formula I

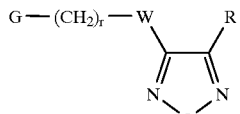

Formula I'

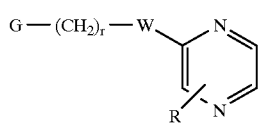

wherein

W is oxygen or sulphur;

R is hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $-CF_3$, $-CN$, Y, phenyl or phenoxy wherein phenyl or phenoxy is optionally substituted with halogen, $-CN$, $C_{1-4}$-alkyl, $C_{1-4}$-alkoxy, $-OCF_3$, $-CF_3$, $-CONH_2$ or $-CSNH_2$; or R is phenyl or benzyloxycarbonyl, each of which is optionally substituted with halogen, $-CN$, $C_{1-4}$-alkyl, $C_{1-4}$-alkoxy, $-OCF_3$, $-CF_3$, $-CONH_2$ or $-CSNH_2$; or R is $-OR^5Y$, $-SR^5Y$, $OR^5-Z-Y$, $-SR^5ZY$, $-O-R^5-Z-R^4$ or $-S-R^5-Z-R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

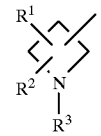

het-1

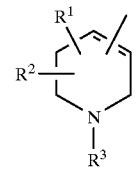

het-2

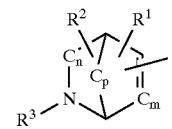

het-3

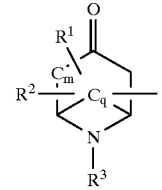

het-4

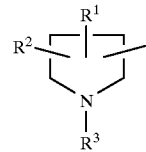

het-5

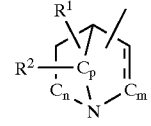

het-6

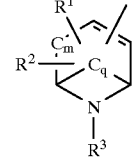

het-7 or G can optionally be substituted $C_3$–$C_8$ cycloalkyl or optionally substituted $C_{1-6}$-alkyl wherein the substitution is $-NR^6R^7$;

$R^6$ and $R^7$ independently are hydrogen, $C_{1-6}$-alkyl; or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with $-OH$, $-COR^{6'}$, $CH_2-OH$, halogen, $-NH_2$, carboxy, or phenyl;

$R^3$ is hydrogen, $C_{1-5}$-alkyl, $C_{2-5}$-alkenyl or $C_{2-5}$-alkynyl;

$R^{6'}$ is hydrogen, $C_{1-6}$-alkyl;

n is 0, 1 or 2;

m is 0, 1 or 2;

p is 0, 1 or 2;

q is 1 or 2;

r is 0, 1 or 2;

....... is a single or double bond; and

Formula I$^{1'}$ $$G'-(CH_2)_{r'}-W' \quad R' \atop {\underset{S}{N \diagdown \diagup N}}\qquad (I^{1'})$$

wherein

W' is oxygen or sulfur;

R' is hydrogen, amino, halogen, NHR$^{6'}$, NR$^{6'}$R$^{7'}$, R$^{4'}$, —OR$^{4'}$, —SR$^{4'}$, —SOR$^{4'}$, —SO$_2$R$^{4'}$, $C_{3-10}$-cycloalkyl, $C_{4-12}$-(cycloalkylalkyl), —Z'—$C_{3-10}$-cycloalkyl and —Z'—$C_{4-12}$-(cycloalkylalkyl) wherein R$^{4'}$ is $C_{1-15}$-alkyl, $C_{2-15}$-alkenyl, $C_{2-15}$-alkynyl, each of which is optionally substituted with one or more halogen(s), —CF$_3$, —CN, Y', phenyl or phenoxy wherein phenyl or phenoxy is optionally substituted with halogen, —CN, $C_{1-4}$-alkyl, $C_{1-4}$-alkoxy, —OCF$_3$, —CF$_3$, —CONH$_2$ or —CSNH$_2$; or R' is phenyl or benzyloxycarbonyl, each of which is optionally substituted with halogen, —CN, $C_{1-4}$-alkyl, $C_{1-4}$-alkoxy, —OCF$_3$, —CF$_3$, —CONH$_2$ or —CSNH$_2$; or R' is —OR$^{5'}$Y', —SR$^{5'}$Y', OR$^{5'}$—Z'—Y', —SR$^{5'}$Z'Y', —O—R$^{5'}$—Z—R$^{4'}$ or —S—R$^{5'}$—Z'—R$^{4'}$ wherein Z, is oxygen or sulphur, R$^{5'}$ is $C_{1-15}$-alkyl, $C_{2-15}$-alkenyl, $C_{2-15}$-alkynyl, and Y' is a 5 or 6 membered heterocyclic group; and G' is selected from one of the following azacyclic or azabicyclic ring systems:

het-1
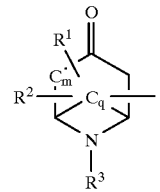

het-2
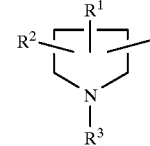

het-3
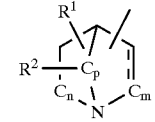

het-4
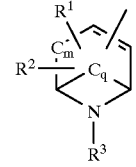

het-5

het-6
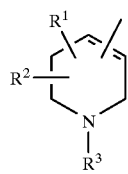

het-7
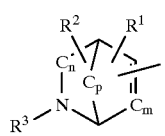

or G' can optionally be substituted $C_3$–$C_8$ cycloalkyl or optionally substituted $C_{1-6}$-alkyl wherein the substitution is —NR$^{6'}$R$^{7'}$;

R$^{6'}$ and R$^{7'}$ independently are hydrogen, $C_{1-6}$-alkyl; or

R$^{6'}$ and R$^{7'}$ together with the nitrogen atom optionally form a 4- to 6-member ring;

R$^1$ and R$^2$ independently are hydrogen, $C_{1-5}$-alkyl, $C_{2-5}$-alkenyl, $C_{2-5}$-alkynyl, $C_{1-10}$-alkoxy, $C_{1-5}$-alkyl substituted with —OH, —COR$^{6''}$, CH$_2$—OH, halogen, —NH$_2$, carboxy, or phenyl;

R$^3$ is hydrogen, $C_{1-5}$-alkyl, $C_{2-5}$-alkenyl or $C_{2-5}$-alkynyl;

R$^{6''}$ is hydrogen, $C_{1-15}$-alkyl n is 0, 1 or 2;

m is 0, 1 or 2;

p is 0, 1 or 2;

q is 1 or 2;

r is 0, 1 or 2;

....... is a single or double bond; or a pharmaceutically acceptable salt or solvate thereof and one or more Synergistic Analgesics in a weight ratio of First Compound to Synergistic Analgesic of from about 1 to about 1000.

The present invention provides a method for treating pain comprising administering to a patient in need thereof, using an anagesic composition comprising a First Compound selected from the group consisting of:

Formula I

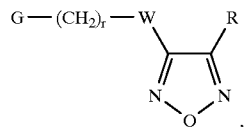

Formula I'

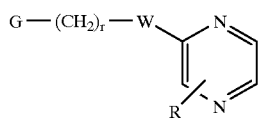

wherein

W is oxygen or sulphur;

R is hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $-CF_3$, $-CN$, Y, phenyl or phenoxy wherein phenyl or phenoxy is optionally substituted with halogen, $-CN$, $C_{1-4}$-alkyl, $C_{1-4}$-alkoxy, $-OCF_3$, $-CF_3$, $-CONH_2$ or $-CSNH_2$; or R is phenyl or benzyloxycarbonyl, each of which is optionally substituted with halogen, $-CN$, $C_{1-4}$-alkyl, $C_{1-4}$-alkoxy, $-OCF_3$, $-CF_3$, $-CONH_2$ or $-CSNH_2$; or R is $-OR^5Y$, $-SR^5Y$, $OR^5-Z-Y$, $-SR^5ZY$, $-O-R^5-Z-R^4$ or $-S-R^5-Z-R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

het-1

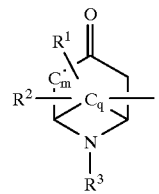

het-2

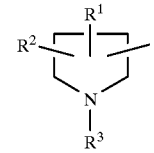

het-3

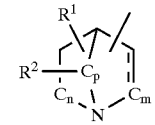

het-4

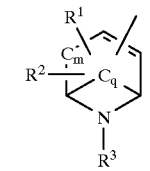

het-5 het-6 het-7 or G can optionally be substituted $C_3$–$C_8$ cycloalkyl or optionally substituted $C_{1-6}$-alkyl wherein the substitution is $-NR^6R^7$;

$R^6$ and $R^7$ independently are hydrogen, $C_{1-6}$-alkyl; or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with $-OH$, $-COR^{6'}$, $CH_2-OH$, halogen, $-NH_2$, carboxy, or phenyl;

$R^3$ is hydrogen, $C_{1-5}$-alkyl, $C_{2-5}$-alkenyl or $C_{2-5}$-alkynyl;

$R^{6'}$ is hydrogen, $C_{1-6}$-alkyl;

n is 0, 1 or 2;

m is 0, 1 or 2;

p is 0, 1 or 2;

q is 1 or 2;

r is 0, 1 or 2;

.......  is a single or double bond; and

Formula I¹'

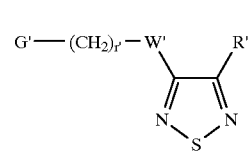

wherein

W' is oxygen or sulfur;

R' is hydrogen, amino, halogen, $NHR^{6'}$, $NR^{6'}R^{7'}$, $R^{4'}$, $-OR^{4'}$, $-SR^{4'}$, $-SOR^{4'}$, $-SO_2R^{4'}$, $C_{3-10}$-cycloalkyl, $C_{4-12}$-(cycloalkylalkyl), —Z'—$C_{3-10}$-cycloalkyl and —Z'-$C_{4-12}$-(cycloalkylalkyl) wherein $R^{4'}$ is $C_{1-15}$-alkyl, $C_{2-15}$-alkenyl, $C_{2-15}$-alkynyl, each of which is optionally substituted with one or more halogen(s), —$CF_3$, —CN, Y', phenyl or phenoxy wherein phenyl or phenoxy is optionally substituted with halogen, —CN, $C_{1-4}$-alkyl, $C_{1-4}$-alkoxy, —$OCF_3$, —$CF_3$, —$CONH_2$ or —$CSNH_2$; or R' is phenyl or benzyloxycarbonyl, each of which is optionally substituted with halogen, —CN, $C_{1-4}$-alkyl, $C_{1-4}$-alkoxy, —$OCF_3$, —$CF_3$, —$CONH_2$ or —$CSNH_2$; or R' is —$OR^{5'}Y'$, —$SR^{5'}Y'$, $OR^{5'}$—Z'—Y', —$SR^{5'}Z'Y'$, —O—$R^{5'}$—Z—$R^{4'}$ or —S—$R^{5'}$—Z'—$R^{4'}$ wherein Z' is oxygen or sulphur, $R^{5'}$ is $C_{1-15}$-alkyl, $C_{2-15}$-alkenyl, $C_{2-15}$-alkynyl, and Y' is a 5 or 6 membered heterocyclic group; and G' is selected from one of the following azacyclic or azabicyclic ring systems:

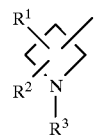

het-1

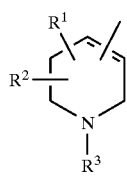

het-2

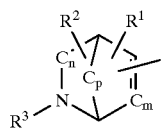

het-3

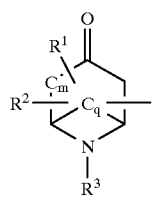

het-4

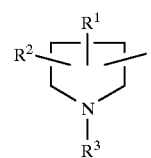

het-5

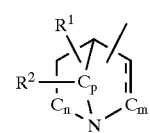

het-6

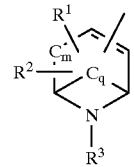

het-7 or G' can optionally be substituted $C_3$–$C_8$ cycloalkyl or optionally substituted $C_{1-6}$-alkyl wherein the substitution is —$NR^{6'}R^{7'}$;

$R^{6'}$ and $R^{7'}$ independently are hydrogen, $C_{1-6}$-alkyl; or $R^{6'}$ and $R^{7'}$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$alkoxy, $C_{1-5}$-alkyl substituted with —OH, —$COR^{6''}$, $CH_2$—OH, halogen, —$NH_2$, carboxy, or phenyl;

$R^3$ is hydrogen, $C_{1-5}$-alkyl, $C_{2-5}$-alkenyl or $C_{2-5}$-alkynyl;

$R^{6''}$ is hydrogen, $C_{1-15}$-alkyl n is 0, 1 or 2;

m is 0, 1 or 2;

p is 0, 1 or 2;

q is 1 or 2;

r is 0, 1 or 2;

⋯⋯ is a single or double bond; or a pharmaceutically acceptable salt or solvate thereof; one or more Synergistic Analgesics in a weight ratio of First Compound to Synergistic Analgesic of from about 1 to about 1000.

It is to be understood that the invention extends to the use of each of the stereoisomeric forms of the compounds of the present invention as well as the pure diastereomeric, pure enantiomeric, and racemic forms of the named compounds.

As used herein, the terms "Synergistic Analgesic" and "Synergistic Analgesics" refer to the group consisting of Nonsteroidal anti-inflammatory drugs (NSAIDS), acetaminophen, alpha-adrenergic compounds, and opioids.

As used herein, the term "Selected Muscarinic Compound" and "Selected Muscarinic Compounds" refers to a compound selected from the group consisting of Formula I

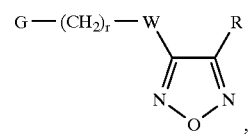

I

Formula I'

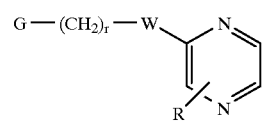

I' wherein

W is oxygen or sulphur;

R is hydrogen, amino, halogen, $NHR^6$, $NR^6R^7$, $R^4$, —$OR^4$, —$SR^4$, —$SOR^4$, —$SO_2R^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), —$CF_3$, —CN, Y, phenyl or phenoxy wherein phenyl or phenoxy is optionally substituted with halogen, —CN, $C_{1-4}$-alkyl, $C_{1-4}$-alkoxy, —$OCF_3$, —$CF_3$, —$CONH_2$ or —$CSNH_2$; or R is phenyl or benzyloxycarbonyl, each of which is optionally substituted with halogen, —CN, $C_{1-4}$-alkyl, $C_{1-4}$-alkoxy, —$OCF_3$, —$CF_3$, —$CONH_2$ or —$CSNH_2$; or R is —$OR^5Y$, —$SR^5Y$, $OR^5$—Z—Y, —$SR^5ZY$, —O—$R^5$—Z—$R^4$ or —S—$R^5$—Z—$R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

het-1
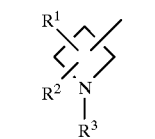

het-2
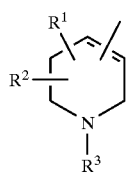

het-3
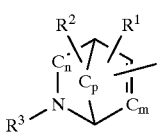

het-4
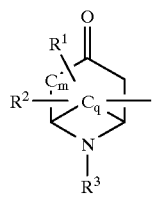

het-5
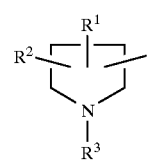

het-6
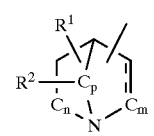

-continued het-7
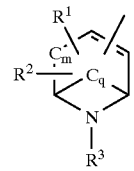

or G can optionally be substituted $C_3$–$C_8$ cycloalkyl or optionally substituted $C_{1-6}$-alkyl wherein the substitution is —$NR^6R^7$;

$R^6$ and $R^7$ independently are hydrogen, $C_{1-6}$-alkyl; or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —$COR^{6'}$, $CH_2$—OH, halogen, —$NH_2$, carboxy, or phenyl;

$R^3$ is hydrogen, $C_{1-5}$-alkyl, $C_{2-5}$-alkenyl or $C_{2-5}$-alkynyl;

$R^{6'}$ is hydrogen, $C_{1-6}$-alkyl;

n is 0, 1 or 2;

m is 0, 1 or 2;

p is 0, 1 or 2;

q is 1 or 2;

r is 0, 1 or 2;

........ is a single or double bond; and

Formula I¹'

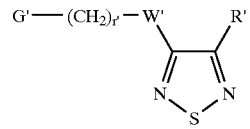

(I¹')

wherein

W' is oxygen or sulfur;

R' is hydrogen, amino, halogen, $NHR^{6'}$, $NR^{6'}R^{7'}$, $R^{4'}$, —$OR^{4'}$, —$SR^{4'}$, —$SOR^{4'}$, —$SO_2R^{4'}$, $C_{3-10}$-cycloalkyl, $C_{4-12}$-(cycloalkylalkyl), —Z'—$C_{3-10}$-cycloalkyl and —Z'—$C_{4-12}$-(cycloalkylalkyl) wherein $R^{4'}$ is $C_{1-15}$-alkyl, $C_{2-15}$-alkenyl, $C_{2-15}$-alkynyl, each of which is optionally substituted with one or more halogen(s), —$CF_3$, —CN, Y', phenyl or phenoxy wherein phenyl or phenoxy is optionally substituted with halogen, —CN, $C_{1-4}$-alkyl, $C_{1-4}$-alkoxy, —$OCF_3$, —$CF_3$, —$CONH_2$ or —$CSNH_2$; or R' is phenyl or benzyloxycarbonyl, each of which is optionally substituted with halogen, —CN, $C_{1-4}$-alkyl, $C_{1-4}$-alkoxy, —$OCF_3$, —$CF_3$, —$CONH_2$ or —$CSNH_2$; or R' is —$OR^{5'}Y'$, —$SR^{5'}Y'$, $OR^5$—Z'—Y', —$SR^{5'}Z'Y'$, —O—$R^{5'}$—Z—$R^{4'}$ or —S—$R^{5'}$—Z'—$R^{4'}$ wherein Z' is oxygen or sulphur, $R^{5'}$ is $C_{1-15}$-alkyl, $C_{2-15}$-alkenyl, $C_{2-15}$-alkynyl, and Y' is a 5 or 6 membered heterocyclic group; and G' is selected from one of the following azacyclic or azabicyclic ring systems:

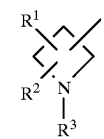
het-1

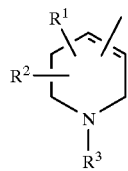
het-2

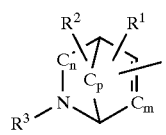
het-3

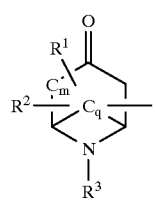
het-4

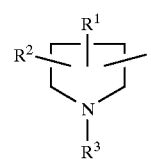
het-5

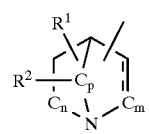
het-6

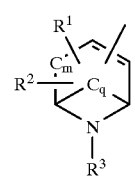
het-7 or G' can optionally be substituted $C_3$–$C_8$ cycloalkyl or optionally substituted $C_{1-6}$-alkyl wherein the substitution is —$NR^{6'}R^{7'}$;

$R^{6'}$ and $R^{7'}$ independently are hydrogen, $C_{1-6}$-alkyl; or $R^{6'}$ and $R^{7'}$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —$COR^{6''}$, $CH_2$—OH, halogen, —$NH_2$, carboxy, or phenyl;

$R^3$ is hydrogen, $C_{1-5}$-alkyl, $C_{2-5}$-alkenyl or $C_{2-5}$-alkynyl;

$R^{6''}$ is hydrogen, $C_{1-15}$alkyl n is 0, 1 or 2;

m is 0, 1 or 2;

p is 0, 1 or 2;

q is 1 or 2;

r is 0, 1 or 2;

⋯⋯ is a single or double bond; or a pharmaceutically acceptable salt or solvate thereof.

The term "alkyl" refers to the number of carbon atoms indicated; however, when no number is specified, the term refers to $C_{1-6}$ alkyl. The alkyl may be linear or branched unless specified.

As used herein with reference to the G and/or G' substituent, the —$(CH_2)_{r'}$—W'-thiadiazole, —$(CH_2)_r$—W-oxadiazole, or —$(CH_2)_r$—W-pyrazine moiety can be attached at any carbon atom of the azacyclic or azabicyclic ring. Further, $R^1$ and $R^2$ of the G and/or G' substituent may be present at any position, including the point of attachment of the —$(CH_2)_{r'}$—W'-thiadiazole, —$(CH_2)_r$—W-oxadiazole, or —$(CH_2)_r$—W-pyrazine moiety.

As used herein with reference to the G and/or G' substituent, the phrase "$R^6$ and $R^7$ together with the nitrogen atom optionally form a 4- to 6-member ring" and "$R^{6'}$ and $R^{7'}$ together with the nitrogen atom optionally form a 4- to 6-member ring" means that $R^6$ and $R^7$ or $R^{6'}$ and $R^{7'}$ are each independently hydrogen, $C_1$–$C_6$ alkyl wherein the $R^6$ and $R^7$ or $R^{6'}$ and $R^{7'}$ groups may optionally join to form a 4- to 6-member ring including the nitrogen. For example, optionally joined groups include, but are not limited to:

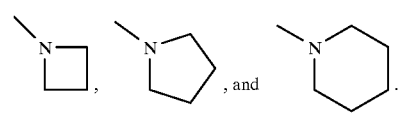

As used herein with reference to the G substituent, the numbering shall be as follows:

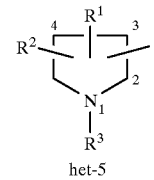
het-5

As used herein the term α shall refer to a position on the G substituent which is one position away from the N atom of the G substituent. For example, in the following illustration (1E), both positions 2 and 6 are considered α. The term γ shall refer to the position on the G substituent which is opposite the N atom. For example, in the illustration (1E), position 4 is considered γ. Likewise, β shall refer to the 3 and 5 position in the illustration.

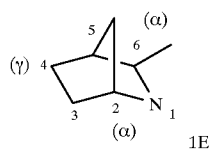

As used herein the phrase "interacting with a muscarinic cholinergic receptor" shall include compounds which block muscarinic cholinergic receptors or modulate such receptors. Likewise, the term "interacting with a nicotinic cholinergic receptor" shall include compounds which block or modulate the receptor. The phrase shall include the effect observed when compounds act as agonists, partial agonists and/or antagonists at a cholinergic receptor.

As used herein, the term h⁺ refers to an alkoxide metal, wherein the term "alkoxide metal" means a metal suitable for alkoxide formation. Such alkoxide metals include, but are not limited to, $Li^+$, $K^+$, $Na^+$, $Cs^+$, and $Ca^{++}$. Especially preferred alkoxide metals include $Li^+$, $K^+$, and $Na^+$.

As used herein, the term "halogen" means Cl, Br, F, and I. Especially preferred halogens include Cl, Br, and I.

As used herein the phrase "one or more selected from" shall more preferredly refer to from 1–3 substituents. The term shall further preferredly refer to from 1–2 substituents.

The terms "$C_1$–$C_{n'}$ alkyl" wherein n' can be from 2 through 15, as used herein, represent a branched or linear alkyl group having from one to the specified number of carbon atoms. Typical $C_1$–$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$–$C_{n'}$ alkenyl" wherein n' can be from 3 through 10, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=$CHCH_2CH_3$), hexenyl, pentenyl, and the like.

The term "$C_2$–$C_5$ alkynyl" refers to an unsaturated branched or linear group having from 2 to 5 carbon atoms and at least one triple bond. Examples of such groups include, but are not limited to, 1-propynyl, 2-propynyl, 1-butynyl, 2-butynyl, 1-pentynyl, and the like.

The terms "halogen($C_1$–$C_6$)alkyl" and "halogen($C_2$–$C_6$) alkenyl" refer to alkyl or alkenyl substituents having one or more independently selected halogen atoms attached at one or more available carbon atoms. These terms include, but are not limited to, chloromethyl, 1-bromoethyl, 2-bromoethyl, 1,1,1-trifluoroethyl, 1,1,2-trifluoroethyl, 1,2,2-trifluoroethyl, 2,2,2-trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, 1-chloroethylenyl, 2-chloroethylenyl, 5-fluoro-3-pentenyl, 3-chloro-2-bromo-5-hexenyl, 3-chloro-2-bromobutyl, trichloromethyl, 1,1-dichloroethyl, 1,2-dichloroethyl, 2,2-dichloroethyl, 1,4-dichlorobutyl, 3-bromopentyl, 1,3-dichlorobutyl, 1,1-dichloropropyl, and the like.

The term "$C_2$–$C_{10}$ alkanoyl" represents a group of the formula C(O) ($C_1$–$C_9$) alkyl. Typical $C_2$–$C_{10}$ alkanoyl groups include acetyl, propanoyl, butanoyl, and the like.

The term "($C_1$–$C_6$ alkyl) amino" refers to a monoalkylamino group. Examples of such groups are methylamino, ethylamino, iso-propylamino, n-propylamino, (n-propyl) amino, (iso-propyl)amino, n-propylamino, t-butylamino, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "substituted($C_5$–$C_{n'}$) cycloalkyl" refers to a cycloalkyl group as described supra wherein the cycloalkyl group may be substituted with from one to four substituents independently selected from the group consisting of hydrogen, $C_1$–$C_6$ alkyl, $NO_2$, halogen, halogen($C_1$–$C_6$) alkyl, halogen($C_2$–$C_6$)alkenyl, $C_2$–$C_6$ alkenyl, $CO_2R^{20}$, ($C_1$–$C_6$ alkyl) amino, —$SR^{20}$, and $OR^{20}$; wherein $R^{20}$ is selected from the group consisting of $C_{1-15}$-alkyl, $C_{2-15}$-alkenyl, $C_{2-15}$-alkynyl.

The term "$C_3$–$C_8$ cycloalkyl-($C_1$–$C_3$)alkyl" represents an alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms. Such groups include, but are not limited to, cyclohexyl-1,3-dienyl, cyclohexenyl, cyclopentenyl, cycloheptenyl, cyclooctenyl, cyclohexyl-1,4-dienyl, cycloheptyl-1,4-dienyl, cyclooctyl-1,3,5-trienyl and the like.

The term "substituted ($C_5$–$C_8$) cycloalkenyl" refers to a cycloalkenyl group as described supra. wherein the cycloalkenyl group may be substituted with from one to four substituents independently selected from the group consisting of hydrogen, $C_1$–$C_6$ alkyl, $NO_2$, halogen, halogen ($C_1$–$C_6$)alkyl, halogen($C_2$–$C_6$)alkenyl, $C_2$–$C_6$ alkenyl, $COR^{20}$, $C_2$–$C_{10}$ alkanoyl, $C_7$–$C_{16}$ arylalkyl, $CO_2R^{20}$, ($C_1$–$C_6$ alkyl) amino, —$SR^{20}$, and —$OR^{20}$; wherein $R^{20}$ is selected from the group consisting of $C_{1-15}$-alkyl, $C_{2-15}$-alkenyl, and $C_{2-15}$-alkynyl.

The term "$C_5$–$C_8$ cycloalkenyl-($C_1$–$C_3$)alkyl" represents a $C_1$–$C_3$ alkyl group substituted at a terminal carbon with a $C_5$–$C_8$ cycloalkenyl group.

As used herein, the phrase "5 or 6 membered heterocyclic group" means a group containing from one to four N, O or S atom(s) or a combination thereof, which heterocyclic group is optionally substituted at carbon or nitrogen atom(s) with $C_{1-6}$-alkyl, —$CF_3$, phenyl, benzyl or thienyl, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having 3-heteroatoms; 6-membered heterocycles with one heteroatom (e.g. pyridine, quinoline, isoquinoline, phenanthrine, 5,6-cycloheptenopyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-member heterocycles with four heteroatoms. Particularly preferred are thiophenes, pyridines, and furans.

As used herein the term "carboxy" refers to a substituent having the common meaning understood by the skilled artisan, wherein the point of attachment may be through the carbon or oxygen atom of the group.

As used herein the term "aryl" means an organic radical derived from an aromatic hydrocarbon by the removal of one atom; e.g., phenyl or naphthyl. Most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The term "aryl($C_1$–$C_3$) alkyl" refers to any aryl group which is attached to the parent moiety via the alkyl group.

As used herein the term "phosphorous(III) compound" has the art accepted meaning of the term. For example, the term includes, but is in no way limited to, triphenylphosphine, tri(p-toluyl) phosphine, tributyl phosphine, tri(p-dimethylaminiophenyl) phosphine, triethyl phosphine, and trimethyl phosphine. The artisan can choose other appropriate phosphorous(III) compounds using methods and literature references which are commonly available to the chemist artisan.

As used herein the term "diester of azodicarboxylate" has the art accepted meaning of the term. For example, the term includes, but is in no way limited to diethylazodicarboxylate, dimethylazodicarboxylate, diisopropylazodicarboxylate, and ditertbutylazodicarboxylate. The skilled chemist can determine other appropriate diesters of azodicarboxylate using methods and literature readily available to the chemist artisan.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

The compounds of Formula I' can be prepared using the chemical processes illustrated in Scheme I. The starting materials for the illustrated process are commercially available or may be prepared using methods known to the skilled artisan

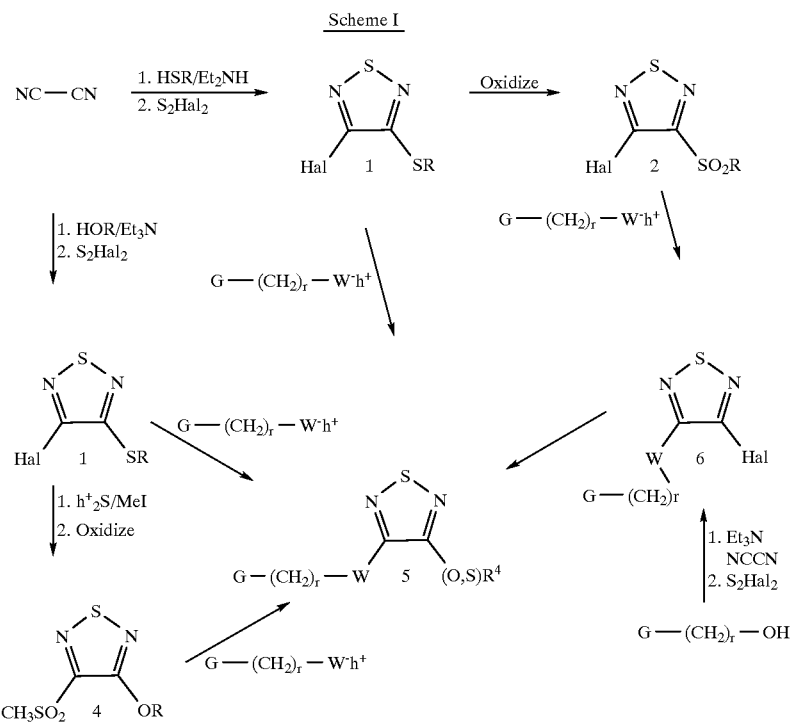

Scheme I

As used in Scheme I, R, h$^+$, and G are as defined supra. As used in Scheme I, the term "Hal" refers to Cl, Br, and $R^9SO_2$. Preferred oxidizing agents for the process of Scheme I include oxone and sodium periodate. Oxone is an especially preferred oxidizing agent for the process of Scheme I. Compounds of Formula 3, as illustrated in Scheme I wherein the OR group is replaced by an $R^4$ group, can be prepared using methods well known in the art. See for example, U.S. Pat. No. 5,043,345.

Further, compounds of Formula I may be prepared using the process illustrated in the following Scheme II

Scheme II

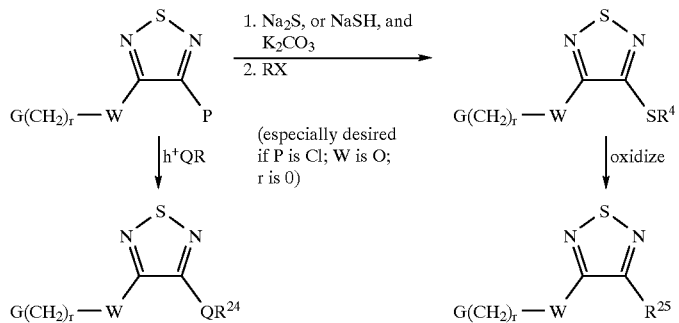

As used in Scheme II, Q may be N, O or S; $R^{24}$ is selected from the group consisting of hydrogen, $R^4$, $R^5$, $R^6$, and $R^7$; $R^{25}$ is selected from the group consisting of $SOR^4$ and $SO_2R^4$; all other meanings are as defined supra.

Additional compounds of Formula I may be prepared using the process illustrated by Scheme III.

Scheme III

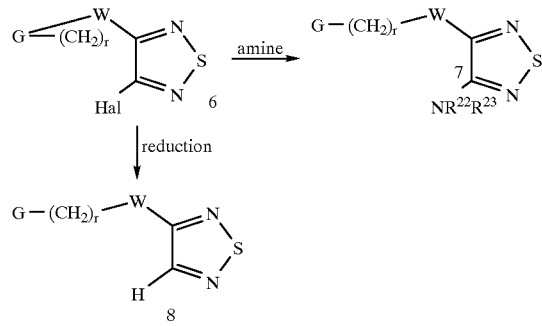

As used in Scheme III, Hal, W, r, and G are as defined supra. As used in Scheme III, $R^{22}$ and $R^{23}$ are independently selected from the group consisting of hydrogen, $R^6$ and $R^7$.

Certain intermediates of the present invention may be prepared using the process illustrated in Scheme IV.

Scheme IV

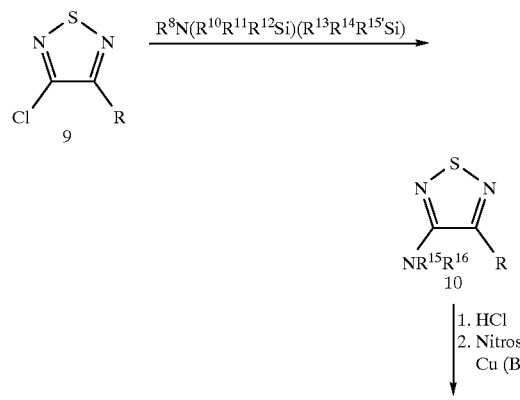

-continued

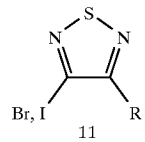

As used in Scheme IV, $R^8$, Si, $R^{10}$, $R^{11}$, $R^{12}$, $R^{13}$, $R^{14}$, $R^{15'}$, $R^{15}$ and $R^{16}$ are as defined supra. For example, $R^8N[(R^{10}R^{11}R^{12}Si)(R^{13}R^{14}R^{15'}Si)$ may be, but is not limited to lithium bis(tri-2-propylsilyl)amide, sodium bis(trimethylsilyl)amide, potassium bis(trimethylsilyl)amide, lithium bis(tri-2-propylsilyl)amide, sodium bis(ethyldimethylsilyl)amide, potassium bis(1-propylethylmethylsilyl)amide, lithium bis(tri-phenylsilyl)amide, sodium bis(triphenylmethylsilyl)amide, potassium bis(2-butyl-2-propylmethylsilyl)amide, lithium (tri-2-propylsilyl)(2-butyldiethylsilyl)amide, sodium (trimethylsilyl)(triphenylsilyl)amide, potassium (dimethyl phenylsilyl)(ethyldimethylsilyl)amide, and the like. Most preferably, $R^{15}$ and $R^{16}$ are each hydrogen when the process of Scheme III is used for preparing a compound of 11 from a compound of 10. The intermediate 10 may be nitrosated using standard nitrosating procedures. A preferred nitrosating agent is isoamyl nitrite; however, other known nitrosating agents are appropriate. As used in Scheme III, the term "Cu(Br,I)" refers to copper (I) bromide, copper (II) bromide, or copper (I) iodide. The artisan will recognize that the copper (I) bromide, copper (II) bromide, or copper (I) iodide reagent shall determine the substitution on the product of the process illustrated in Scheme III.

Certain compounds of this invention may more preferably be prepared by a process using a hydroxyalkylamine (G—OH) wherein G has the meaning defined supra. in the presence of a phosphorus(III) compound and a diester of azodicarboxylate to give the 1,2,5-thiadiazoyloxyalkylamine as illustrated by Scheme V.

Scheme V

-continued

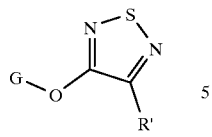

The G groups are as defined supra. The R' is selected from the group consisting of hydrogen, halogen, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl);

$R^4$ is selected from the group consisting of $C_{1-15}$-alkyl, $C_{2-15}$-alkenyl, $C_{2-15}$-alkynyl, each of which is optionally substituted with one or more independently selected from the group consisting of halogen(s), $-CF_3$, $-CN$, Y, phenyl and phenoxy wherein phenyl or phenoxy is optionally substituted with one or more independently selected from the group consisting of halogen, $-CN$, $C_{1-4}$-alkyl, $C_{1-4}$-alkoxy, $-OCF_3$, or $-CF_3$; or R' is phenyl or benzyloxycarbonyl, each of which is optionally substituted with one or more independently selected from the group consisting of halogen, $-CN$, $C_{1-4}$-alkyl, $C_{1-4}$-alkoxy, $-OCF_3$, and $-CF_3$; or R' selected from the group consisting of $-OR^5Y$, $-SR^5Y$, $OR^5-Z-Y$, $-SR^5ZY$, $-O-R^5-Z-R^4$ and $-S-R^5-Z-R^4$;

Z is oxygen or sulphur;

$R^5$ is selected from the group consisting of $C_{1-15}$-alkyl, $C_{2-15}$-alkenyl, and $C_{2-15}$-alkynyl;

Y is a 5 or 6 membered heterocyclic group;

$R^{1'}$ is selected from the group consisting of phenyl, $C_{1-15}$-alkyl, $C_{2-5}$-alkenyl, $C_{2-5}$-alkynyl and $(NR^{2'})_3$;

$R^{2'}$ and $R^{3'}$ are independently selected from the group consisting of hydrogen, $C_{1-15}$-alkyl, $C_{2-5}$-alkenyl, $C_{2-5}$-alkynyl, and $C_{1-5}$-alkyl substituted with one or more selected from the group consisting of halogen and phenyl;

W is oxygen or sulphur;

$R^6$, and $R^7$ independently are $C_{1-6}$-alkyl; or $R^6$ and $R^7$ together with the nitrogen atom optionally form a 4- to 6-member ring;

$R^1$ and $R^2$ are independently selected from hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of $-COR^{6'}$, halogen, and phenyl;

$R^{6'}$ is hydrogen or $C_1$–$C_3$ alkyl;

$R^3$ is selected from the group consisting of $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

........ is a single or double bond.

Preferred $R^{1'}$ groups include phenyl, $C_{1-15}$-alkyl, and $(NR^{2'})_3$. The process of Scheme IV is particularly advantageous because the process provides a method for inverting the stereochemistry at the carbon bearing the hydroxyl group in G.

Another new process illustrated by Scheme VI, involves the sequential reaction of 3,4-dihydroxy-1,2,5-thiadiazole with G—OH wherein G is defined as defined supra. in the presence of a phosphorous(III) compounds and a diester of azodicarboxylate to give an unisolated hydroxy-1,2,5-thiadiazole ether I" followed by reaction of I" with $R^4OH$ where $R^4$ is defined as supra. with phosphorous(III) compounds and a diester of azodicarboxylate to give the diethers of 3,4-dihydroxy-1,2,5-thiadiazole which are useful as muscarinic agonists and antagonists. (See, Org. Prep. & Procedures 1969, 1, 255–258) The substituents illustrated in Scheme VI are as defined supra.

Scheme VI

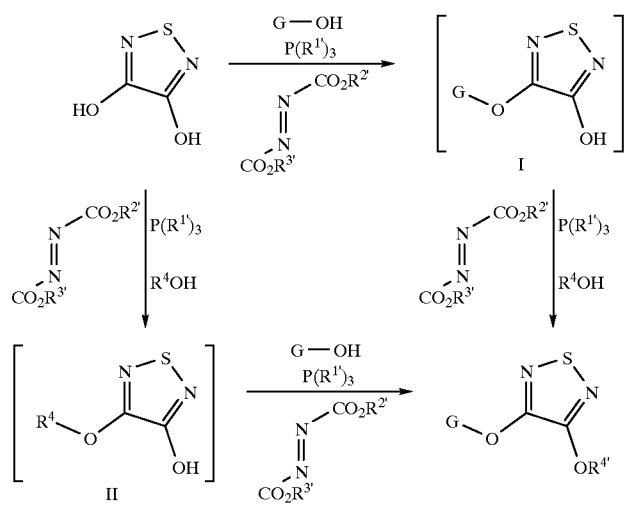

Alternatively, the order of addition of the alcohols may be reversed as shown above to give unisolated hydroxy-1,2,5-thiadiazole ether II which is subsequently converted to the same final muscarinic active compound.

The process illustrated by Scheme VII encompases the reaction of a phenol or hydroxyheteroaryl compound with compound III in the presence of a phosphorus(III) compound and a diester of azodicarboxylate to give compound IV.

Scheme VII

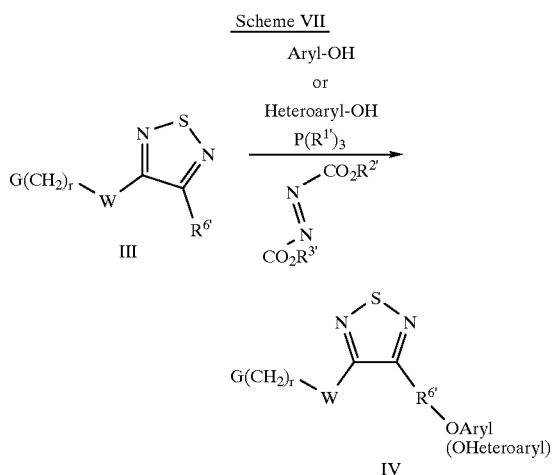

In compound III, $G(CH_2)_rW$ is as defined supra. and $R^{6'}$ is selected from the group consisting of $R^7$, $-OR^7$, $-SR^7$, $-SOR^7$, $-SO_2R^7$, $C_{3-10}$-cycloalkyl, $C_{4-12}$-(cycloalkylalkyl), $-Z-C_{3-10}$-cycloalkyl and $-Z-C_{4-12}$-(cycloalkylalkyl);

$R^7$ is $C_{1-15}$-alkyl, $C_{2-15}$-alkenyl, $C_{2-15}$-alkynyl, each of which is optionally substituted with one or more independently selected from the group consisting of halogen(s), $-CF_3$, $-CN$, Y, phenyl and phenoxy; wherein phenyl or phenoxy is optionally substituted with one or more selected from the group consisting of halogen, $-CN$, $C_{1-4}$-alkyl, $C_{1-4}$-alkoxy, $-OCF_3$, and $-CF_3$;

provided that at least one alkyl atom of $R^6$, is substituted with a hydroxyl group or $R^{6'}$ is a substituent selected from the group consisting of $-OR^8Y$, $-SR^8Y$, $OR^8-Z-Y$, $-SR^8ZY$, $-O-R^8-Z-R^7$ and $-S-R^8-Z-R^7$ wherein each $-OR^8Y$, $-SR^8Y$, $OR^8-Z-Y$, $-SR^8ZY$, $-O-R^8-Z-R^7$ and $-S-R^8-Z-R^7$ is substituted with a alkylhydroxyl;

Y is a 5 or 6 membered heterocyclic group;

Z is oxygen or sulphur;

$R^8$ is $C_{1-15}$-alkyl, $C_{2-15}$-alkenyl, $C_{2-15}$-alkynyl; aryl and heteroaryl is optionally substituted with one or more independently selected from the group consisting of halogen, $-CN$, $C_{1-4}$-alkyl, $C_{1-4}$-alkoxy, $C_{1-4}$-alkylthio, $C_{1-4}$-alkylsulfone, $C_{1-4}$-alkylsulfoxide, $-OCF_3$, $NO_2$, $N(R^7)_2$, and $-CF_3$; heteroaryl group is a 5 or 6 membered heterocycle containing one to four N, O, or S atoms or a combination thereof.

Another process of this invention, illustrated by Scheme VIII, is the synthesis of 3-hydroxy-4-alkylthio-1,2,5-thiadiazoles by treating 3-halo-4-alkylthio-1,2,5-thiadiazoles with aqueous alkaline metal hydroxides in the presence or absence of a dipolar aprotic solvent. In this scheme, Hal has the meanings defined supra. and M is an alkali metal, W is O or S.

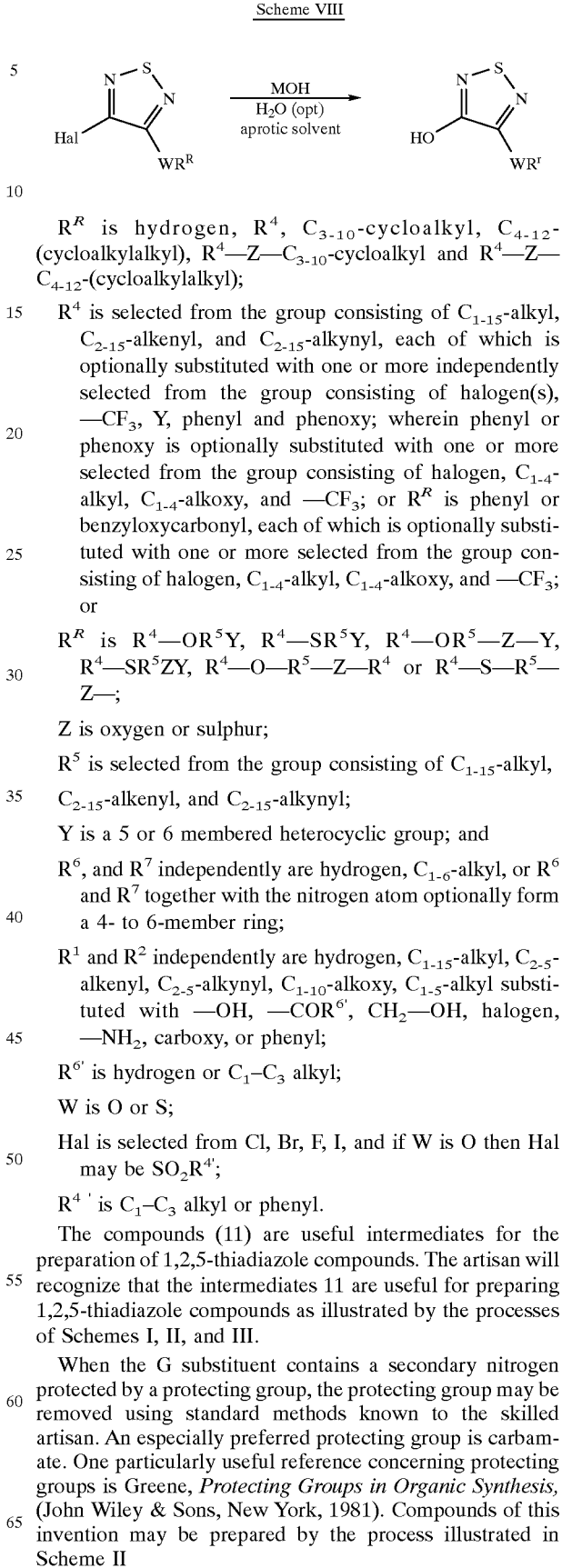

$R^R$ is hydrogen, $R^4$, $C_{3-10}$-cycloalkyl, $C_{4-12}$-(cycloalkylalkyl), $R^4-Z-C_{3-10}$-cycloalkyl and $R^4-Z-C_{4-12}$-(cycloalkylalkyl);

$R^4$ is selected from the group consisting of $C_{1-15}$-alkyl, $C_{2-15}$-alkenyl, and $C_{2-15}$-alkynyl, each of which is optionally substituted with one or more independently selected from the group consisting of halogen(s), $-CF_3$, Y, phenyl and phenoxy; wherein phenyl or phenoxy is optionally substituted with one or more selected from the group consisting of halogen, $C_{1-4}$-alkyl, $C_{1-4}$-alkoxy, and $-CF_3$; or $R^R$ is phenyl or benzyloxycarbonyl, each of which is optionally substituted with one or more selected from the group consisting of halogen, $C_{1-4}$-alkyl, $C_{1-4}$-alkoxy, and $-CF_3$; or $R^R$ is $R^4-OR^5Y$, $R^4-SR^5Y$, $R^4-OR^5-Z-Y$, $R^4-SR^5ZY$, $R^4-O-R^5-Z-R^4$ or $R^4-S-R^5-Z-$;

Z is oxygen or sulphur;

$R^5$ is selected from the group consisting of $C_{1-15}$-alkyl, $C_{2-15}$-alkenyl, and $C_{2-15}$-alkynyl;

Y is a 5 or 6 membered heterocyclic group; and $R^6$, and $R^7$ independently are hydrogen, $C_{1-6}$-alkyl, or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with $-OH$, $-COR^{6'}$, $CH_2-OH$, halogen, $-NH_2$, carboxy, or phenyl;

$R^{6'}$ is hydrogen or $C_1-C_3$ alkyl;

W is O or S;

Hal is selected from Cl, Br, F, I, and if W is O then Hal may be $SO_2R^{4'}$;

$R^{4'}$ is $C_1-C_3$ alkyl or phenyl.

The compounds (11) are useful intermediates for the preparation of 1,2,5-thiadiazole compounds. The artisan will recognize that the intermediates 11 are useful for preparing 1,2,5-thiadiazole compounds as illustrated by the processes of Schemes I, II, and III.

When the G substituent contains a secondary nitrogen protected by a protecting group, the protecting group may be removed using standard methods known to the skilled artisan. An especially preferred protecting group is carbamate. One particularly useful reference concerning protecting groups is Greene, *Protecting Groups in Organic Synthesis*, (John Wiley & Sons, New York, 1981). Compounds of this invention may be prepared by the process illustrated in Scheme II

Scheme II

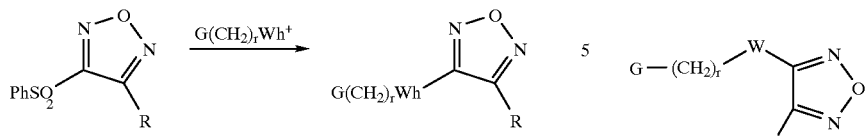

The artisan will recognize that the starting materials for the process of Scheme II are commercially available or can be prepared using methods familiar to the skilled artisan.

Compounds of Formula I wherein R is an $R^4$ group, can be prepared using methods well known in the art. See for example, U.S. Pat. No. 5,043,345.

Further, compounds of Formula I may be prepared using the process illustrated in the following Scheme III

Scheme III

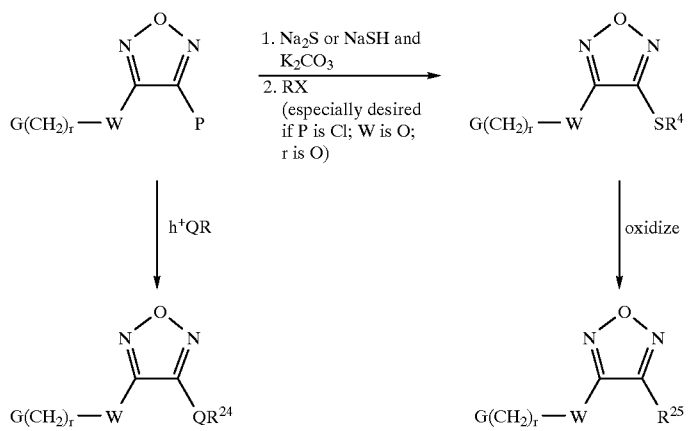

As used in Scheme III, Q may be N, O or S; $R^{24}$ is selected from the group consisting of hydrogen, $R^4$, $R^5$, $R^6$, and $R^7$; $R^{25}$ is selected from the group consisting of $SOR^4$ and $SO_2R^4$; all other meanings are as defined supra.

Additional compounds of Formula I may be prepared using the process illustrated by Scheme IV.

Scheme IV

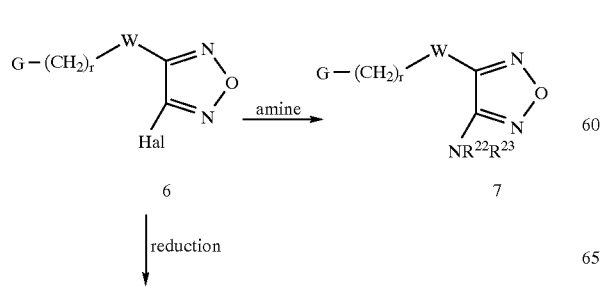

As used in Scheme IV, Hal, W, r, and G are as defined supra. As used in Scheme IV, $R^{22}$ and $R^{23}$ are independently selected from the group consisting of hydrogen, $R^6$ and $R^7$.

Compounds of Formula I' can be prepared by a) reacting a compound of formula II

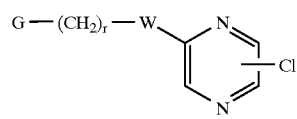

II wherein G, W and r have the meaning defined above with $h^+QR$ wherein $h^+$ is an alkoxide metal; Q is O or S and R has the meaning defined above, or b) reacting a compound of formula III or IV

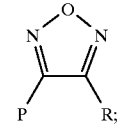

III

-continued

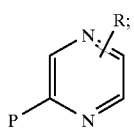
IV wherein P is $R^9SO_2$ or halogen; $R^9$ is $C_{1-8}$ straight or branched chain alkyl or aryl; and R has the meaning defined above; with G—$(CH_2)_r$—$W^-$—$h^+$ wherein $h^+$, G, W and r have the meanings defined above.

The compounds of Formula I' can be prepared as described supra. and by using the chemical processes illustrated in Scheme I. The starting materials for the illustrated process are commercially available or may be prepared using methods known to the skilled artisan.

Scheme I

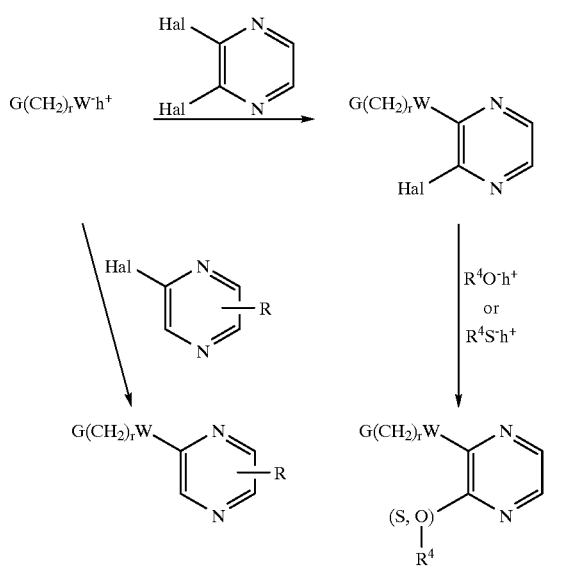

As used in Scheme I, R, $h^+$, and G are as defined supra. As used in Scheme I, the term "Hal" refers to Cl, Br, I, and $R^9SO_2$.

When the G substituent contains a secondary nitrogen protected by a protecting group, the protecting group may be removed using standard methods known to the skilled artisan. An especially preferred protecting group is carbamate. One particularly useful reference concerning protecting groups is Greene, *Protecting Groups in Organic Synthesis*, (John Wiley & Sons, New York, 1981).

Certain compounds of this invention may more preferredly be prepared using the process of Scheme V.

Scheme V

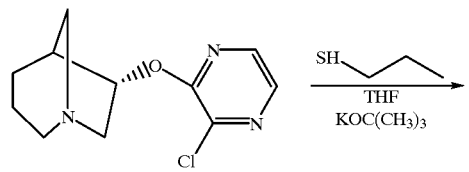

-continued

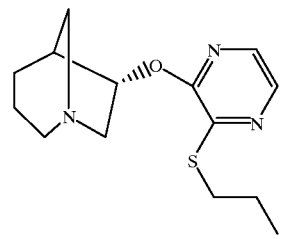

Potassium t-butoxide or another appropriate alkali metal base was added at about 0° C. to an alkylthiol in THF and stirred. The haloopyrazine was added and the reaction stirred at about room temperature. A sample of about 1 N acid was added and the aqueous solution washed. The pH was adjusted to about 12.0. The product was extracted, dried and evaporated. The salt was optionally formed using standard methods.

Certain of the compounds of this invention can more preferredly be prepared using the process illustrated by Scheme VI.

Scheme VI

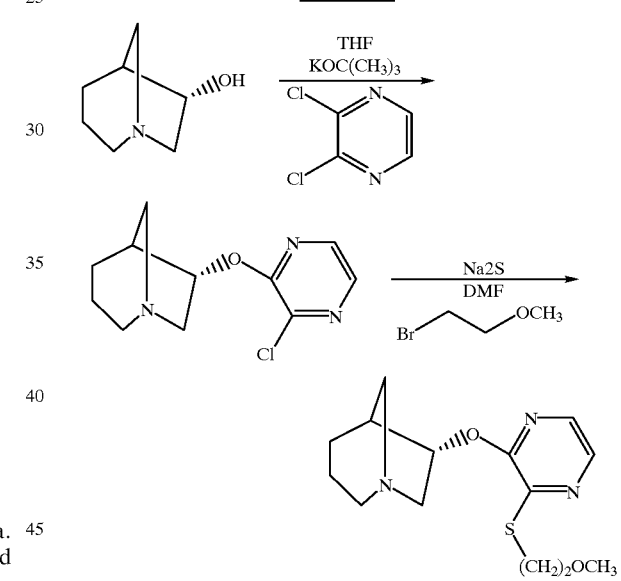

The alcohol was added to a mixture of potassium t-butoxide in THF at about room temperature. The reaction was cooled to about 5° C. The 2,3-dichloropyrazine in THF was added to the mixture. The reaction mixture was stirred at about room temperature for about 2 hrs, condensed, diluted with water and ethyl acetate. The organic solution was dried and condensed. The chloropyrazine derivative and sodium sulfide ($Na_2S\cdot 9H_2O$), were heated in DMF at about 50° C. for about 3.5 hr, cooled to about 0° C. Then 2-Bromoethylmethylether was added. The reaction was stirred at about room temperature overnight and diluted with ethyl acetate and about 5 N acid. The aqueous layer was washed and the pH adjusted to about 12.0. The product was extracted, dried, condensed and purified by HPLC. The salt form of the product was optionally formed using standard methods.

The term "analgesic dose", as used herein, represents an amount of compound necessary to prevent or treat a human susceptible to or suffering from pain following administration to such human. The active compounds are effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from anxiety, the compounds may also be administered by a variety of other routes such as the transdermal, parenterally, subcutaneous, intranasal, intramuscular and intravenous routes. Such formulations may be designed to provide delayed or controlled release using formulation techniques which are known in the art.

The term "NSAIDS", as used herein, represents a non-steroidal anti-inflammatory drug which can be identified as such by the skilled artisan. For example, the Merck Manual, 16th Edition, Merck Research Laboratories (1990) pp 1308–1309 provide well known examples of NSAIDS. The term is intended to include, but is not limited to salicylates such as aspirin, indomethacin, ibuprofen, naproxen, fenoprofen, tolmetin, sulindac, meclofenamate, keoprofen, piroxicam, flurbiprofen, and diclofenac. Especially preferred NSAIDS include aspirin, ibuprofen, and naproxen. Alternative preferred NSAIDS are indomethacin, ibuprofen, naproxen, fenoprofen, tolmetin, sulindac, meclofenamate, keoprofen, piroxicam, flurbiprofen, and diclofenac. Particularly preferred NSAIDS include aspirin and ibuprofen. The salicylates may include acetylsalicylic acid, sodium acetylsalicylic acid, calcium acetylsalicylic acid, salicylic acid, and sodium salicylate. An especially preferred NSAID is ibuprofen.

The term "acetaminophen", as used herein, shall have the art accepted meaning and refers to N-(4-Hydroxyphenyl) acetamide and 4'-hydroxyacetanilide. The compound is claimed in U.S. Pat. No. 2,998,450 and is known to the skilled artisan.

The term "central alpha-adrenergic active compounds", as used herein, represents a compound having central alpha-adrenergic receptor activity. The most preferred central alpha-adrenergic active compound is clonidine or a pharmaceutically acceptable salt thereof having the chemical name: 2-(2,6-dichlorophenylamino)-2-imidazoline.

Clonidine is known to be useful for treating hypertension. see Physicians' Desk Reference, 45th Ed. (1991) p. 673.

The term "opioid", as used herein, represents opioid analgesics and antagonists including natural opioid analgesics, synthetic opioid analgesics, opioid antagonists and opioid agonist-antagonists. Preferred an opioid compounds are selected from the group consisting of morphine, codeine, meperidine, methadone, propoxyphene, levorphanol, hydromorphone, oxymorphone, oxycodone, brompton's cocktail, naloxone, naltrexone, pentazocine, butorphanol, nabuphine, and buprenorphine. More preferred opioid compounds are selected from the group consisting of codeine, nabuphine, naloxone, and naltrexone.

Preferred an opioid compounds are morphine, codeine, meperidine, methadone, propoxyphene, levorphanol, hydromorphone, oxymorphone, oxycodone, brompton's cocktail, naloxone, naltrexone, pentazocine, butorphanol, nabuphine, and buprenorphine.

Especially preferred opioid compounds are selected from the group consisting of hydromorphone, hydrocodone, meperidone, buprenorphine, butorphenol, nalbuphine, pentazocine, oxymorphone, oxycodone, levorphanol, fentanyl, and alphaprodine.

Particularly preferred opioid compounds are selected from the group consisting of propoxyphene, methadone, morphine, hydrocodone, hydromorphine, and codeine. The especially particularly preferred opioid compounds are selected from morphine and codeine.

As used herein, the phrase "one or more" most preferredly refers to one; however, two, three, or more may be used.

We have discovered that a group of compounds having muscarinic cholinergic activity can be particular useful for treating pain when used in combination with non-steroidal antiinflammatory agents (NSAIDS). More specifically, the invention provides a method of treating pain in humans using a specified known compounds (collectively referred to herein as "selected muscarinic compounds") in combination with a NSAIDS to provide a synergistic effect. The Selected Muscarinic Compounds are believed to be active based on activity at muscarinic cholinergic receptors; however, the present invention is in no way limited by the mechanism of action.

We have discovered that a group of compounds having muscarinic cholinergic activity can be particular useful for treating pain when used in combination with acetaminophen. More specifically, the invention provides a method of treating pain in humans using a specified Selected Muscarinic Compounds in combination with acetaminophen to provide a synergistic effect.

Further, we have discovered that a group of compounds having muscarinic cholinergic activity can be particularly useful for treating pain when used in combination with central alpha-adrenergic active compounds. More specifically, the invention provides a method of treating pain in humans using Selected Muscarinic Compounds in combination with a central alpha-adrenergic active compound to provide a synergistic effect.

Oral combinations of aspirin with codeine or other narcotic analgesics are known to provide additive analgesic effects in man. The Pharmacological Basis of Therapeutics, 5th edition, Macmillan Publishing Co., 1975, pp 325–358.

The present invention further envisions that one or more Selected Muscarinic Compounds may be used at one time in the composition of this invention to provide the desired analgesic effect.

In the composition of this invention a Selected Muscarinic Compound and NSAIDS compound are combined in a weight ratio of Compound to NSAIDS of from about 1 to about 1000.

A preferred composition is a weight ratio of Compound to NSAIDS of from about 1 to about 100. An especially preferred ratio is from about 1 to about 30. A further preferred ratio may be from about 1 to about 10. A final preferred ratio may be from about 1 to about 3.

There are many NSAIDS known in the literature and to the skilled artisan.

In the composition of this invention a Selected Muscarinic Compound and acetaminophen are combined in a weight ratio of Selected Muscarinic Compound to acetaminophen of from about 1 to about 1000.

A preferred composition is a weight ratio of Selected Muscarinic Compound to acetaminophen of from about 1 to about 100. An especially preferred ratio is from about 1 to about 30. A further preferred ratio may be from about 1 to about 10. A final preferred ratio may be from about 1 to about 3.

The Selected Muscarinic Compounds are effective over a wide dosage range; however, it is desirable to administer a dosage that is as low as possible. The amount of NSAIDS present in the composition is adjusted as described above in ratio to the Selected Muscarinic Compound dosage. The amount of acetaminophen present in the composition is adjusted as described above in ratio to the Selected Muscarinic compound dosage.

In the composition of this invention a Selected Muscarinic Compound selected and one or more opioid compounds are combined in a weight ratio of Selected Muscarinic Compound to opioid compound of from about 1 to about 1000.

A preferred composition is a weight ratio of Selected Muscarinic Compound to opioid compound of from about 1 to about 100. An especially preferred ratio is from about 1 to about 30. A further preferred ratio may be from about 1 to about 10. A final preferred ratio may be from about 1 to about 3.

The amount of opioid compound present in the composition is adjusted as described above in ratio to the Selected Muscarinic Compound dosage.

However, for each composition claimed herein, it will be understood that the amount of the Selected Muscarinic Compound actually administered will be determined by a physician, in the light of the relevant circumstances including the condition to be treated, the choice of Selected Muscarinic Compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from pain, the compounds may also be administered by a variety of other routes such as the transdermal, parenterally, subcutaneous, intranasal, intramuscular and intravenous routes. Such formulations may be designed to provide delayed or controlled release using formulation techniques which are known in the art.

Transdermal formulations containing the composition claimed herein most preferably deliver the active substances in an effective amount for from about three days to about seven days. However, for chronic pain such as arthritis or cancer pain, a transdermal delivery of from about three days to up to about two weeks is desirable. Alternatively, it may be preferred to deliver the claimed compositions transdermally in an effective amount for from about one day to about three days.

As used herein the term "treating" includes prophylaxis of a physical and/or mental condition or amelioration or elimination of the developed physical and/or mental condition once it has been established or alleviation of the characteristic symptoms of such condition.

The Selected Muscarinic Compounds employed in the invention are not believed to act via the GABA/benzodiazepine, 5HT1A, or D1 receptor systems in humans. Rather, the activity of the present Selected Muscarinic Compounds as analgesic agents is believed to be based upon modulation of muscarinic cholinergic receptors. However, the mechanism by which the present compounds function is not necessarily the mechanism stated supra., and the present invention is not limited by any mode of operation.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

The route of administration may be any route, which effectively transports the active compound to the appropriate or desired site of action, such as oral or parenteral e.g. rectal, transdermal, depot, subcutaneous, intravenous, intramuscular or intranasal, the oral route being preferred.

The dosage administered will, of course, vary depending on known factors such as the pharmacodynamic characteristics of the particular agent, and its mode and route of administration; age, health, and weight of the recipient; nature and extent of the symptoms, kind of concurrent treatment, frequency of treatment, and the effect desired. Usually, the daily dosage can be such that the active ingredient is administered at a daily dosage of from about 0.2 mg/kg to about 100 mg/kg of body weight Selected Muscarinic Compound and from about 0.6 to about 200 mg/kg of NSAIDS.

Compositions suitable for internal administration contain from about one half (0.5) milligrams to about 600 milligrams of active ingredient per unit. In these pharmaceutical compositions, the active ingredient will ordinarily be present in an amount of from about 0.5% to about 95% by weight based on the total weight of the composition.

For compositions containing acetaminophen, usually, the daily dosage can be such that the active ingredient is administered at a daily dosage of from about 0.2 mg/kg to about 500 mg/kg of body weight Selected Muscarinic Compound and from about 0.6 to about 200 mg/kg of acetaminophen.

Typical compositions include a compound of Selected Muscarinic Compound and one or more NSAIDSs, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

Typical compositions include a Selected Muscarinic Compound and acetaminophen, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used, as described above.

A preferred composition is a weight ratio of Selected Muscarinic Compound to central alpha-adrenergic active compound of from about 1 to about 100. An especially preferred ratio is from about 1 to about 30. A further preferred ratio may be from about 1 to about 10. A final preferred ratio may be from about 1 to about 3.

The Selected Muscarinic Compounds are effective over a wide dosage range; however, it is desirable to administer a dosage that is as low as possible. The amount of central alpha-adrenergic active compound present in the composition is adjusted as described above in ratio to the Selected Muscarinic Compound dosage.

Usually, the daily dosage can be such that the active ingredient is administered at a daily dosage of from about 0.2 mg/kg to about 500 mg/kg of body weight Selected Muscarinic ompound and from about 0.6 to about 200 mg/kg of central alpha-adrenergic active compound.

Typical compositions include a Selected Muscarinic Compound and one or more central alpha-adrenergic active compounds, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compositions of this invention are dispensed in unit form comprising from about 0.1 to about 300 mg in a pharmaceutically acceptable carrier per unit dosage.

The compositions of this invention may be suitable for administration to an animal. Such animals include both domestic animals, for example livestock, laboratory animals, and household pets, and non-domestic animals such as wildlife. More preferredly, the animal is a vertebrate. Most preferredly, a composition of this invention shall be administered to a mammal. It is especially preferred that the animal is a domestic mammal or a human. The most preferred mammal is a human. For such domestic animal purposes, a composition of this invention may be administered as a feed additive.

The following models and assays are useful for illustrating the effectiveness of the compositions claimed herein.

Nociceptive Pain Model

Acetic acid-induced writhing: A standard procedure for detecting and comparing the analgesic activity of different classes of analgesic drugs for which there is a good correlation with human analgesic activity is the prevention of acetic acid-induced writhing in mice. Mice, are subcutaneously administered various doses of the claimed composition and are injected injected intraperitoneally with acetic acid (0.5% solution, 10 ml/kg) 5 min prior to a designated observation period. For scoring purposes a "writhe" is indicated by whole body stretching or contraction of the abdomen during the observation period beginning 5 min after receiving the acetic acid. Inhibition of writhing behavior is demonstrative of analgesic activity.

See, Haubrich, D. R., Ward, S. J., Baizman, E., Bell, M. R., Bradford, J., Ferrari, R., Miller, M., Perrone, M., Pierson, A. K., Saelens, J. K. and Luttinger, D.: Pharmacology of pravadoline: a new analgesic agent. The Journal of Pharmacology and Experimental Therapeutics 255 (1990) 511–522.

Neuropathic Pain Model

Sciatic nerve ligation model: Rats are anesthetized and a nerve ligation procedure performed. The common sciatic nerve is exposed and 4 ligatures tied loosely around it with about 1 mm spacing. One day to 10 weeks after surgery, the nociceptive testing is performed. Responses to noxious heat are determined by placing the rats in a chamber with a clear glass floor and aiming at the plantar surface of the affected foot a radiant heat source from beneath the floor. Increased latency to withdraw the hindpaw is demonstrative of analgesic activity. Responses to normally innocuous mechanical stimuli is determined by placing the rats in a chamber with a screen floor and stimulating the plantar surface of the hind paw with graduated von Frey hairs which are calibrated by the grams of force required to bend them. Rats with sciatic nerve ligation respond to lower grams of mechanical stimulation by reflexive withdrawal of the foot than unoperated rats. This response to stimuli which are normally innocuous is termed allodynia. Increases in the grams of mechanical force required to produce foot withdrawal is demonstrative of antiallodynic activity.

See, Bennett, G. J. and Xie, Y.-K. A peripheral mononeuropathy in rat that produces disorders of pain sensation like those seen in man. Pain 33 (1988) 87–107. See also, Lee, Y.-W., Chaplan, S. R. and Yaksh, T. L.: Systemic and supraspinal, but not spinal, opiates suppress allodynia in a rat neuropathic pain model. Neuroci Lett 186 (1995) 111–114.

Formalin paw test: Rats are anesthetized and when there is a loss of spontaneous movement the rats are injected subcutaneously in the dorsal surface of the hindpaw with 50 ul of 5% formalin solution using a 30 gauge needle. Rats are then individually placed in an open Plexiglas chamber for observation, and within a maximum interval of 1 to 2 min, the animal displays recovery from anesthesia with spontaneous activity and normal motor function. Pain behavior is quantified by periodically counting the incidents of spontaneous flinching/shaking of the injected paw. The flinches are counted for 1-min periods at 1- to 2-, 5- to 6- and 5 min intervals during the interval from 10 to 60 min. Inhibition of the pain behavior is demonstrative of an analgesic activity.

See, Malmberg, A. B. and Yaksh, T. L.: Antinociceptive actions of spinal nonsteroidal anti-inflammatory agents on the formalin test in the rat. The Journal of Pharmacology and Experimental Therapeutics 263 (1992) 136–146.

Inflammatory Pain Model

Brewer's yeast-induced hyperalgesia (Randall-Selitto Test): To assess nociceptive threshold in rats, ascending pressure is applied gradually to the paw with a motor driven weight of a Ugo Basile Analgesy Meter. Rats respond to the pressure by either pulling free of the device, struggling or vocalizing. Hyperalgesia is induced by a hind paw subplantar injection of 0.1 ml of 1% suspension of brewer's yeast in 0.9% saline. The composition of this invention is administered at varying times (0–4 hr) after injection of brewer's yeast and pressure threshold for the inflamed paw again determined at varying times. Increases in the pressure which produces a behavioral response is demonstrative of analgesic activity.

See, Haubrich, D. R., Ward, S. J., Baizman, E., Bell, M. R., Bradford, J., Ferrari, R., Miller, M., Perrone, M., Pierson, A. K., Saelens, J. K. and Luttinger, D.: Pharmacology of pravadoline: a new analgesic agent. The Journal of Pharmacology and Experimental Therapeutics 255 (1990) 511–522.

Utility Test Methods

The unexpectedly enhanced analgesic activity of the composition of the invention is evidenced by tests intially conducted on mice. Male mice are fasted for 16–22 hours and weighed. Mice weighing from about 18–22 grams at the time of testing are used for the following studies. All mice are dosed sequentially by the oral route with suspensions of a composition of this invention. Doses are coded using a code unknown to the observer.

A stock suspension of the test composition is prepared by mixing the active ingredients with about 40 mL of an aqueous vehicle containing about 2% Tween 80 (R), a pharmacological dispersant and containing 100% polysorbate 80, and 1% by weight Methocel (R) MC powder, and containing 100% methylcellulose, in distilled water. The mixture may be sonicated for about 10 to about 15 seconds using an ultrasound sytem. All dosing suspensions are prepared by dilution of the stock suspension with Methocel/Tween 80. All suspensions are used within two hours of preparation.

Mouse Writhing Test

An accepted standard for detecting and comparing the analgesic activity of different classes of analgesic compounds for which there is a good correlation with human analgesic activity is the prevention of phenyl-p-benzoquinone induced writhing in mice. [H. Blumberg et al. Proc. Soc. Exp. biol. Med., 118, 763–766 (1965)].

Mice, treated with various doses of Selected Muscarinic Compound, composition or vehicle are injected intraperitoneally with a standard challenge dose of phenyl-p-benzoquinone 5 minutes prior to a designated observation period. The pheyl-p-benzoquinone is prepared as about 0.1 mg/ml solution in about 5% by volume of ethanol in water. The writhing dose is 1.25 mg/kg injected at a volume of about 0.25 ml/10 g. For scoring purposes a "writhe" is indicated by whole body stretching or contracting of the abdomen during an observation period beginning about five minutes after the phenyl-p-benzoquinone dose.

All ED50 values and their 95% confidence limits are determined using accepted numerical methods. For example, see W. F. Thompson, *Bacteriological Rev.*, 11, 115–145 (1947). The interaction of the dosages on phenyl-p-benzoquinone induced writhing in mice is demonstrated by the Loewe isobologram (S. Loewe, Pharm. Rev. 9, 237–242 (1957).

The solid line connecting the ED50 dosages of Selected Muscarinic Compound (alone) and Synergistic Analgesic as claimed herein (alone) represents the "ED50 addition line" which indicates the expected location of the ED50's for Selected Muscarinic Compound and classical analagesic combinations if simple additivity were to describe their combined effects. The 95% confidence range for the ED50 addition line is shown by the area between the broken lines above and below the ED50 addition line.

According to Loewe's isobolic theory, if the analgesic effects are simply additive to one another, then the expected location of the ED50's of the Selected Muscarinic Compound and Synergistic Analgesic component of each fixed dosage ratio would be contained within or overlap the region of the ED50 addition line. Combination ED50's located significantly below the ED50 addition line would represent unexpectedly enhanced analgesic activity and combination ED50's located above the line would represent unexpected diminished analgesic effect.

One method to establish the significance of such unexpected enhanced or diminished activity is to calculate the best fitting polynomial regression line to the observed ED50's using standard mathematical techniques.

Such experiments demonstrate that compositions comprised of a Selected Muscarinic Compound and one or more Synergistic Analgesics provides a statistically significant synergistic analgesic effect.

Preferred compounds of Formula I' are selected from the group consisting of:
(+/−)-3-butylthio-4-(azabicyclo[2.2.2]octyl-3-oxy)-pyrazine, (+/−)-3-(2-butyloxy)-4-[(+/−)-3-azabicyclo[2.2.2]octyloxy)pyrazine, (+/−)-3-butyloxy-4-[endo-(+/−)-6-[1-azabicyclo[3.2.1]octyloxy)]-pyrazine, 3-(2,2,3,3,4,4,4-heptaflurorobutyloxy)-4-[(+/−)-3-(1-azabicyclo[2.2.2] octyloxy)]-pyrazine, 3-methoxy-4-(1-azabicyclo[2.2.2] octyl-3-oxy)-pyrazine, 3-pentylthio-4-(1 -azabicyclo[2.2.2] ocytl-3-oxy)-pyrazine, trans-3-butyloxy-4-(2-dimethylaminocyclopentyloxy)-pyrazine, 3-butylthio-4-(3-azetidinyloxy)-pyrazine, 3-(3-N-(2-thiazolidonyl) propylthio)-4-(1-azabicyclo[2.2.2]octyl-3-oxy)-pyrazine, 3-chloro-4-(1-azabicyclo[3.2.1]octyl-6-oxy)-pyrazine, 3-(2-2-thio-5-trifluoromethylthienyl)ethylthio)-4-azabicyclo [2.2.2]octyl-3-oxy)-pyrazine, 3-butylthio-4-[3-±-endo-(1-azabicyclo[2.2.1]heptyloxy)]-pyrazine, 3-hexyloxy-4-[6-±-endo-(2-azabicyclo[2.2.2]ocyloxy)]-pyrazine, 3-(4,4,4-trifluorobutylthio)-4-[2-±-exo-(7-azabicyclo[2.2.1] heptyloxy)]-pyrazine, 3-(2-phenoxyethylthio)-4-[3-±-endo-(1-azabicyclo[3.2.1]octyloxy)]-pyrazine, 3-(5-hexenyloxy)-4-[7-±-endo-(2-azabicyclo[2.2.1]heptyloxy)]-pyrazine, 3-butyl-4-[5-(1-azabicyclo[3.2.1]octyloxy)]-pyrazine, and 3-cyclobutylmethyl-4-[2-±-endo-(8-azabicyclo[3.2.1] octyloxy)]-pyrazine.

Some examples of compounds of Formula I' for use in the present analgesic composition include, but are not limited to: 2-[exo-(+/−)-3-[1-azabicyclo[3.2.1]octyloxy)]pyrazine, 3-butylthio-2-(1-azabicyclo[2.2.2]ocytl-3-oxy)]pyrazine, 3-butyloxy-2-[3-±-endo-(1-azabicyclo[2.2.1]heptyloxy)] pyrazine, 3-(2-butynyloxy)-2-[6-±-endo-(1-azabicyclo [3.2.1]octyloxy)pyrazine, 3-hexylthio-2-[6-±-exo-(2-azabicyclo[2.2.1]heptyloxy)]pyrazine, 3-(3-phenylpropynylthio)-2-[2-±-exo-(7-azabicyclo[2.2.1] heptyloxy)]pyrazine, 3-(2-methylthioethoxy)-2-[3-±-exo-(1-azabicyclo[3.2.1]octyloxy)]pyrazine, 3-propargyl-2-[4-(1-azabicyclo[2.2.1]heptyloxy)]pyrazine, and 3-cyclopropylmethylthio-2-[2-±-exo-(8-azabicyclo[3.2.1] octyloxy)]pyrazine.

For analgesic use, Compounds of Formula I may be preferred. Alternatively, Compounds of Formula I' may be preferred. Alternatively, Compounds of Formula I$^{1'}$ may be preferred.

Some prefered characteristics of compounds of Formula I' for use in the present analgesic composition are:

A) W is S;
B) r is 1 or 2;
C) G is selected from het-1 and het-5;
D) G is unsaturated;
E) G is het-4;
F) G is an azabicycle having 7 ring carbon atoms and a nitrogen atom;
G) G is het-6;
H) r is 0;
I) R is selected from halogen, —OR⁵Y, —SR⁵Y, —OR⁵ZY, —SR⁵ZY, —OR⁵ZR⁴, —SR⁵ZR⁴, —OR⁴, and —SR⁴;
J) W is O;
K) m is 1;
L) n is 1;
M) p is 2;
N) G is het-3
O) G is het-2
P) a compound of Formula I'
Q) a compound of Formula I'
wherein W is oxygen or sulphur;

R is selected from the group consisting of hydrogen, amino, halogen, NHR⁶, NR⁶R⁷, R⁴, —OR⁴, —SR⁴, —SOR⁴, —SO₂R⁴, C₃₋₁₀-cycloalkyl, C₄₋₁₂-(cycloalkylalkyl), —Z—C₃₋₁₀-cycloalkyl and —Z—C₄₋₁₂-(cycloalkylalkyl); R⁴ is selected from the group consisting of C₁₋₁₅-alkyl, C₂₋₁₅-alkenyl, and C₂₋₁₅-alkynyl, each of which is optionally substituted with one or more independently selected from the group consisting of halogen(s), —CF₃, —CN, Y, phenyl and phenoxy wherein phenyl or phenoxy is optionally substituted with one or more selected from the group consisting of halogen, —CN, C₁₋₄-alkyl, C₁₋₄-alkoxy, —OCF₃, —CF₃, —CONH₂ and —CSNH₂; or R is phenyl or benzyloxycarbonyl, each of which is optionally substituted with one or more substituents independently selected from the group consisting of halogen, —CN, C₁₋₄-alkyl, C₁₋₄-alkoxy, —OCF₃, —CF₃, —CONH₂ and —CSNH₂; or R is selected from the group consisting of —OR⁵Y, —SR⁵Y, OR⁵—Z—Y, —SR⁵ZY, —O—R⁵—Z—R⁴ and —S—R⁵—Z—R⁴;

Z is oxygen or sulphur;

R⁵ is selected from the group consisting of C₁₋₁₅-alkyl, C₂₋₁₅-alkenyl, and C₂₋₁₅-alkynyl;

Y is a 5 or 6 membered heterocyclic group; and

G is selected from one of the following azacyclic or azabicyclic ring systems:

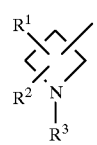
het-1

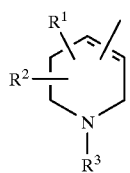
het-2

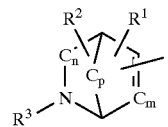
het-3

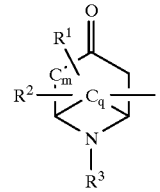
het-4

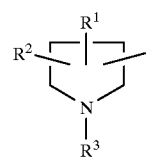
het-5

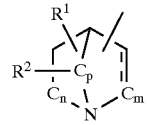
het-6

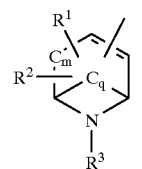
het-7 or G can optionally be substituted C₃–C₈ cycloalkyl wherein the substitution is —NR⁶R⁷;

R⁶ and R⁷ independently are selected from the group consisting of hydrogen and C₁₋₆-alkyl; or R⁶ and R⁷ together with the nitrogen atom optionally form a 4- to 6-member ring;

R¹ and R² independently are selected from the group consisting of hydrogen, C₁₋₁₅-alkyl; C₂₋₅-alkenyl, C₂₋₅-alkynyl, C₁₋₁₀-alkoxy, and C₁₋₅-alkyl substituted with a subsituent independently selected from the group consisting of —OH, —COR⁶', CH₂—OH, halogen, —NH₂, carboxy, and phenyl;

R³ is selected from the group consisting of hydrogen, C₁₋₅-alkyl, C₂₋₅-alkenyl and C₂₋₅-alkynyl;

R⁶' is selected from the group consisting of hydrogen and C₁₋₆-alkyl;

n is 0, 1 or 2;
m is 0, 1 or 2;
p is 0, 1 or 2;
q is 1 or 2;
r is 0, 1 or 2;
⋯⋯ is a single or double bond;

provided that when W is O and G is a saturated azabicyclic group having from 7 to 11 ring carbon atoms and a nitrogen atom wherein the nitrogen atom is separated from the W atom by 2 to 3 ring carbon atoms;

or a pharmaceutically acceptable salt or solvate thereof;

R) The G substituent is selected from the group consisting of

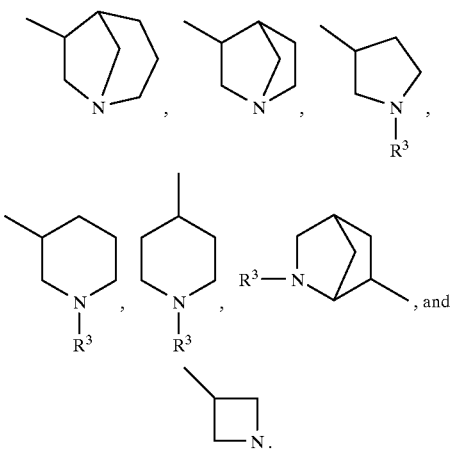

S) The G substituent is

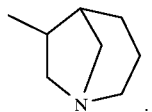

T) R is selected from the group consisting of —SR$^{4'}$, SOR$^{4'}$, —SO$_2$R$^{4'}$, substituted benzyloxycarbonyl wherein the substituents are one or more independently selected from the group consisting of —CN, —OCF$_3$, —CF$_3$, —CONH$_2$ and —CSNH$_2$; or C$_{3-10}$-cycloalkyl, C$_{4-12}$-(cycloalkylalkyl), —Z—C$_{3-10}$-cycloalkyl and —Z—C$_{4-12}$-(cycloalkylalkyl).

U) R is selected from the group consisting of R$^4$, C$_{3-10}$-cycloalkyl, C$_{4-12}$-(cycloalkylalkyl), —Z—C$_{3-10}$-cycloalkyl and —Z—C$_{4-12}$-(cycloalkylalkyl); and R$^4$ is selected from the group consisting of substituted C$_{5-15}$-alkyl, optionally substituted C$_{2-15}$-alkenyl, and optionally substituted C$_{2-15}$-alkynyl, wherein such substituent is one or more independently selected from the group consisting of halogen(s), —CF$_3$, —CN, Y, phenyl and phenoxy; wherein phenyl or phenoxy is optionally substituted with one or more substituents selected from the group consisting of halogen, —CN, C$_{1-4}$-alkyl, C$_{1-4}$-alkoxy, —OCF$_3$, —CF$_3$, —CONH$_2$ and —CSNH$_2$.

V) G is selected from the group consisting of het-4, het-7, het-6 wherein n=2; het-3 wherein one of n and m is 0 or 2; and het-3 wherein the I or I' group is attached at the bridgehead of het-3.

Especially preferred compounds of this invention have the characteristics of A–F,P; A–F,Q; characteristics of A, G, H, M, F; characteristics of G–O,Q; or the characteristics of G–J,M,P; or G–J,M,Q. The characteristics of R and S may be particularly preferred.

Further, especially preferred R groups include phenyl, benzyloxycarbonyl, —OR$^5$Y, —SR$^5$Y, OR$^5$—Z—Y, —SR$^5$ZY, —O—R$^4$—Z—R$^5$ or —S—R$^4$—Z—R$^5$, —SOR$^4$, C$_{3-10}$-cycloalkyl, C$_{4-12}$-(cycloalkylalkyl), —Z—C$_{3-10}$-cycloalkyl and —Z—C$_{4-12}$-(cycloalkylalkyl) wherein Z is oxygen or sulphur, R$^5$ is C$_{1-15}$-alkyl, C$_{2-15}$-alkenyl, C$_{2-15}$-alkynyl, Y is a 5 or 6 membered heterocyclic group containing one to four N, O or S atom(s) or a combination thereof, R$_4$ is C$_{1-15}$-alkyl, C$_{2-15}$-alkenyl, and C$_{2-15}$-alkynyl.

Preferred compounds of Formula I$^{1'}$ are any one or more selected from the group consisting of:

(±)-3-Methoxy-4-(1-azabicyclo[2.2.2]octyl-3-oxy)-1,2,5-thiadiazole,
(±)-3-Ethoxy-4-(1-azabicyclo[2.2.2]octyl-3-oxy)-1,2,5-thiadiazole,
(±)-3-Propyloxy-4-(1-azabicyclo[2.2.2]octyl-3-oxy)-1,2,5-thiadiazole,
(±)-3-Butyloxy-4-(1-azabicyclo[2.2.2]octyl-3-oxy)-1,2,5-thiadiazole,
(±)-3-Pentyloxy-4-(1-azabicyclo[2.2.2]octyl-3-oxy)-1,2,5-thiadiazole,
(±)-3-Hexyloxy-4-(1-azabicyclo[2.2.2]octyl-3-oxy)-1,2,5-thiadiazole,
(±)-3-(4-Methylpentyloxy)-4-(1-azabicyclo[2.2.2]octyl-3-oxy)-1,2,5-thiadiazole,
(±)-3-Chloro-4-(1-azabicyclo[2.2.2]octyl-3-oxy)-1,2,5-thiadiazole,
(±)-3-Propylthio-4-(1-azabicyclo[2.2.2]octyl-3-oxy)-1,2,5-thiadiazole,
(±)-3-Butylthio-4-(1-azabicyclo[2.2.2]octyl-3-oxy)-1,2,5-thiadiazole,
(±)-3-Pentylthio-4-(1-azabicyclo[2.2.2]octyl-3-oxy)-1,2,5-thiadiazole,
(S)-3-Pentylthio-4-(1-azabicyclo[2.2.2]octyl-3-oxy)-1,2,5-thiadiazole,
(±)-3-Hexylthio-4-(1-azabicyclo[2.2.2]octyl-3-oxy)-1,2,5-thiadiazole,
(±)-3-(3,3-Dimethylbutylthio)-4-(1-azabicyclo[2.2.2]octyl-3-oxy)-1,2,5-thiadiazole,
(±)-3-(2-(2-Thienylthio)ethylthio)-4-(1-azabicyclo[2.2.2]octyl-3-oxy)-1,2,5-thiadiazole,
(±)-3-(2,2,3,3,3-Pentafluoropropylthio)-4-(1-azabicyclo[2.2.2]octyl-3-oxy)-1,2,5-thiadiazole,
(±)-3-(3-(2-Thienyl)propylthio)-4-(1-azabicyclo[2.2.2]octyl-3-oxy)-1,2,5-thiadiazole,
(±)-3-Butylthio-4-((1-azabicyclo[2.2.2]octan-3-yl)methoxy)-1,2,5-thiadiazole,
(±)-Exo-3-pentylthio-4-(1-azabicyclo[3.2.1]octyl-6-oxy)-1,2,5-thiadiazole,
(±)-Endo-3-pentylthio-4-(1-azabicyclo[3.2.1]octyl-6-oxy)-1,2,5-thiadiazole,
(±)-Endo-3-butyloxy-4-(1-azabicyclo[2.2.1]heptyl-3-oxy)-1,2,5-thiadiazole,
(±)-Exo-3-butyloxy-4-(1-azabicyclo[2.2.1]heptyl-3-oxy)-1,2,5-thiadiazole,
(±)-3-Butyloxy-4-(3-pyrrolidinyloxy)-1,2,5-thiadiazole,
(±)-3-Butyloxy-4-(1-methyl-3-pyrrolidinyloxy)-1,2,5-thiadiazole,
(±)-3-Butylthio-4-(1-methyl-3-piperidyloxy)-1,2,5-thiadiazole,
3-Butylthio-4-(1-methyl-4-piperidyloxy)-1,2,5-thiadiazole,
(S)-3-Butyloxy-4-(1-methyl-2-pyrrolidinylmethoxy)-1,2,5-thiadiazole,
(S)-3-Butyloxy-4-(2-pyrrolidinylmethoxy)-1,2,5-thiadiazole,
3-Butyloxy-4-(2-(dimethylamino)ethoxy)-1,2,5-thiadiazole,
3-Butylthio-4-(2-(diethylamino)ethoxy)-1,2,5-thiadiazole,
3-Butyloxy-4-(2-(trimethylamino)ethoxy)-1,2,5-thiadiazole iodide,
(R)-3-Pentylthio-4-(1-azabicyclo[2.2.2]octyl-3-oxy)-1,2,5-thiadiazole,
(±)-3-(4-Methylpentylthio)-4-(1-azabicyclo[2.2.2]octyl-3-oxy)-1,2,5-thiadiazole,
(±)-3-(3-Phenylpropylthio)-4-(1-azabicyclo[2.2.2]octyl-3-oxy)-1,2,5-thiadiazole,
(±)-3-(4-Cyanobenzylthio)-4-(1-azabicyclo[2.2.2]octyl-3-oxy)-1,2,5-thiadiazole,
(±)-3-(4-Fluorobenzylthio)-4-(1-azabicyclo[2.2.2]octyl-3-oxy)-1,2,5-thiadiazole, (±)-3-(2-Phenylethylthio)-4-(1-azabicyclo[2.2.2]octyl-3-oxy)-1,2,5-thiadiazole,
(±)-3-(2-Phenyloxyethylthio)-4-(1-azabicyclo[2.2.2]octyl-3-oxy)-1,2,5-thiadiazole,
Endo-3-butyloxy-4-(N-methyl-8-azabicyclo[3.2.1]octyl-3-oxy)-1,2,5-thiadiazole,
(±)-Exo-3-butyloxy-4-(6-(N-methyl-8-azabicyclo[3.2.1]octan-3-onoxy))-1,2,5-thiadiazole,
(±)-Exo-3-chloro-4-(1-azabicyclo[3.2.1]octyl-6-oxy)-1,2,5-thiadiazole,
(±)-Endo-3-chloro-4-(1-azabicyclo[3.2.1]octyl-6-oxy)-1,2,5-thiadiazole,
(±)-Endo-3-(4-cyanobenzylthio)-4-(1-azabicyclo[3.2.1]octyl-6-oxy)-1,2,5-thiadiazole,
3-Butyloxy-4-(3-azetidinyloxy)-1,2,5-thiadiazole,
3-Butylthio-4-(3-azetidinyloxy)-1,2,5-thiadiazole,
(±)-(Trans-3-butyloxy-4-(2-dimethylaminocyclopentyloxy)-1,2,5-thiadiazole,
(±)-3-Butylthio-4-(3-pyrrolidinyloxy)-1,2,5-thiadiazole,
(±)-3-(2-(2-(5-(2-Thienyl)thienyl)thio)ethylthio)-4-(1-azabicyclo[2.2.2]octyl-3-oxy)-1,2,5-thiadiazole,
(±)-3-(2-(5-(2-Thienyl)thienyl)thio)-4-(1-azabicyclo[2.2.2]octyl-3-oxy)-1,2,5-thiadiazole,
(±)-3-(3-N-(2-Thiazolidonyl)propylthio)-4-(1-azabicyclo[2.2.2]octyl-3-oxy)-1,2,5-thiadiazole,
(±)3-Butylthio-4-(exo-2-azabicyclo[2.2.2]oct-6-yloxy)-1,2,5-thiadiazole,
(±)3-(2,2,3,3,4,4,4-heptafluorobutyloxy)-4-[-3-(1-azabicyclo[2.2.2]octyloxy)]-1,2,5-thiadiazole,
(±)3-(1-butylthio)-4-[endo-6-(1-azabicyclo[3.2.1]octyloxy)]-1,2,5-thiadiazole,
(±)3-(3-phenylpropylthio)-4-[endo-6-(1-azabicyclo-[3.2.1]octyloxy)]-1,2,5-thiadiazole
(±)3-[3-(4-fluorophenyl)propylthio]-4-[-3-(1-azabicyclo-[2.2.2]octyloxy)]-1,2,5-thiadiazole
(±)3-{3-[4-(trifluoromethyl)phenyl]propylthio}-4-[-3-(1-azabicyclo[2.2.2]octyloxy)]-1,2,5-thiadiazole; and
(±)3-(1-Butylamino)-4-[-3-(1-azabicyclo[2.2.2]octyloxy)]-1,2,5-thiadiazole; and
(±)-3-(2-Methylthioethyl)-4-(1-azabicyclo[2.2.2]octyl-3-oxy)-1,2,5-thiadiazole
(±)-3-(1-Azabicyclo[2.2.2]octyl-3-oxy)-1,2,5-thiadiazole
(±)-3-Hexyl-4-(1-azabicyclo[2.2.2]octyl-3-oxy)-1,2,5-thiadiazole
(±)-3-Butylsulfonyl-4-(1-azabicyclo[2.2.2]octyl-3-oxy)-1,2,5-thiadiazole
(±)-3-Propylsulfonyl-4-(1-azabicyclo[2.2.2]octyl-3-oxy)-1,2,5-thiadiazole
(±)-3-(4,4,4-Trifluorobutyloxy)-4-(1-azabicyclo[2.2.2]octyl-3-oxy)-1,2,5-thiadiazole
(±)-3-(2-Butynyloxy)-4-(1-azabicyclo[2.2.2]octyl-3-oxy)-1,2,5-thiadiazole
(±)-3-(Cyclopropylmethoxy)-4-(1-azabicyclo[2.2.2]octyl-3-oxy)-1,2,5-thiadiazole
(±)-3-(3-Phenylpropynyloxy)-4-(1-azabicyclo[2.2.2]octyl-3-oxy)-1,2,5-thiadiazole
(±)-3-(3-Butenyloxy)-4-(1-azabicyclo[2.2.2]octyl-3-oxy)-1,2,5-thiadiazole
(±)-3-(trans-2-Butenyloxy)-4-(1-azabicyclo[2.2.2]octyl-3-oxy)-1,2,5-thiadiazole
(±)-3-(cis-2-Butenyloxy)-4-(1-azabicyclo[2.2.2]octyl-3-oxy)-1,2,5-thiadiazole
(±)-3-(2-Methoxyethoxy)-4-(1-azabicyclo[2.2.2]octyl-3-oxy)-1,2,5-thiadiazole
(±)-3-(2-Phenoxyethoxy)-4-(1-azabicyclo[2.2.2]octyl-3-oxy)-1,2,5-thiadiazole
(±)-3-(3-Butynoxy)-4-(1-azabicyclo[2.2.2]octyl-3-oxy)-1,2,5-thiadiazole
(±)-3-(2-Cyclopropylethoxy)-4-(1-azabicyclo[2.2.2]octyl-3-oxy)-1,2,5-thiadiazole
(±)-3-(2-(Methylthio)ethoxy)-4-(1-azabicyclo[2.2.2]octyl-3-oxy)-1,2,5-thiadiazole
(±)-3-(3-Chloropropoxy)-4-(1-azabicyclo[2.2.2]octyl-3-oxy)-1,2,5-thiadiazole
(±)-3-(4-Fluorobutyloxy)-4-(1-azabicyclo[2.2.2]octyl-3-oxy)-1,2,5-thiadiazole
(±)-3-(2-[4-Chlorophenoxy]ethoxy)-4-(1-azabicyclo[2.2.2]octyl-3-oxy)-1,2,5-thiadiazole
(±)-3-(3-[2-methoxy-5-pyridyl]propyloxy)-4-(1-azabicyclo[2.2.2]octyl-3-oxy)-1,2,5-thiadiazole
(±)-3-(trans-3-Chloro-2-propenyloxy)-4-(1-azabicyclo[2.2.2]octyl-3-oxy)-1,2,5-thiadiazole
(±)-3-(2-[4-Fluorophenoxy]ethoxy)-4-(1-azabicyclo[2.2.2]octyl-3-oxy)-1,2,5-thiadiazole
(±)-3-(4-Pentenyloxy)-4-(1-azabicyclo[2.2.2]octyl-3-oxy)-1,2,5-thiadiazole
(±)-3-(3-Fluoropropyloxy)-4-(1-azabicyclo[2.2.2]octyl-3-oxy)-1,2,5-thiadiazole
(±)-3-(Cyclobutylmethoxy)-4-(1-azabicyclo[2.2.2]octyl-3-oxy)-1,2,5-thiadiazole
(±)-3-(3,3,3,2,2-Pentafluoropropyloxy)-4-(1-azabicyclo[2.2.2]octyl-3-oxy)-1,2,5-thiadiazole
(±)-3-(2-[Phenylthio]ethoxy)-4-(1-azabicyclo[2.2.2]octyl-3-oxy)-1,2,5-thiadiazole
(±)-3-(2-[1-napthyloxy]ethoxy)-4-(1-azabicyclo[2.2.2]octyl-3-oxy)-1,2,5-thiadiazole
(±)-3-(2-[4-Bromophenoxy]ethoxy)-4-(1-azabicyclo[2.2.2]octyl-3-oxy)-1,2,5-thiadiazole
(±)-3-(2-Hydroxyethoxy)-4-(1-azabicyclo[2.2.2]octyl-3-oxy)-1,2,5-thiadiazole
3-Butylthio-4-hydroxy-1,2,5-thiadiazole
(±)Exo-3-Butylthio-4-(1-azabicyclo[2.2.1]heptyl-3-oxy)-1,2,5-thiadiazole
(±)-3-(2-[3-{1,2,5-Thiadiazoyloxy}]ethoxy)-4-(1-azabicyclo[2.2.2]octyl-3-oxy)-1,2,5-thiadiazole
(±)-exo-3-Butyloxy-4-(7-azabicyclo[2.2.1]heptyl-3-oxy)-1,2,5-thiadiazole
(±)-3-Butyloxy-4-(3-piperidinyloxy)-1,2,5-thiadiazole
3-Butyloxy-4-(cis-1R-2-aminocyclopentanoxy)-1,2,5-thiadiazole
(±)-endo-3-Hexyloxy-4-(1-azabicyclo[3.2.1]octyl-6-oxy)-1,2,5-thiadiazole
(5S, 6S-(endo-3-Butylthio-4-(1-azabicyclo[3.2.1]octyl-6-oxy)-1,2,5-thiadiazole
(5R, 6R-(endo-3-Butylthio-4-(1-azabicyclo[3.2.1]octyl-6-oxy)-1,2,5-thiadiazole
(±)-trans-3-Butylthio-4-(1-azabicyclo[4.3.0]nonyl-5-oxy)-1,2,5-thiadiazole
(±)-cis-3-Butylthio-4-(1-azabicyclo[4.3.0]nonyl-5-oxy)-1,2,5-thiadiazole
(±)-trans-3-Butylthio-4-(2-dimethylaminocyclopentyloxy)-1,2,5-thiadiazole
3-Butylthio-4-(2-dimethylaminoethoxy)-1,2,5-thiadiazole
(±)-trans-3-Butylthio-4-(N-tert-butylcarboxy-4-hydroxypyrollidin-3-oxy)-1.2.5-thiadiazole
(±)-trans-3-Butylthio-4-(4-hydroxy-pyrollidin-3-oxy)-1.2.5-thiadiazole
(±)-endo-3-Butyloxy-4-(1-azabicyclo[3.2.1]octyl-6-oxy)-1,2,5-thiadiazole
(±)-3-(4-Phenylbutylthio)-4-(1-azabicyclo[2.2.2]octyl-3-oxy)-1,2,5-thiadiazole
(±)-3-(3-Phenyl-2-propenylthio)-4-(1-azabicyclo[2.2.2]octyl-3-oxy)-1,2,5-thiadiazole
(±)-3-(3-[4-Fluorophenyl]propan-3-onethio)-4-(1-azabicyclo[2.2.2]octyl-3-oxy)-1,2,5-thiadiazole (±)-3-(3-[N-Phenothiazinyl]propylthio)-4-(1-azabicyclo[2.2.2]octyl-3-oxy)-1,2,5-thiadiazole
(±)-3-(3-[4-Fluorophenyl]-3-[4-fluorophenoxy]propylthio)-4-(1-azabicyclo[2.2.2]octyl-3-oxy)-1,2,5-thiadiazole
(±)-3-(3-Phenyl-3-[4-trifluoromethylphenoxy]propylthio)-4-(1-azabicyclo[2.2.2]octyl-3-oxy)-1,2,5-thiadiazole
(±)-3-(4,4,4-Trifluorobutylthio)-4-(1-azabicyclo[2.2.2]octyl-3-oxy)-1,2,5-thiadiazole
(±)-3-(3-[3-Pyridyl]propylthio)-4-(1-azabicyclo[2.2.2]octyl-3-oxy)-1,2,5-thiadiazole
(±)-endo-3-(2-Phenoxyethylthio)-4-(1-azabicyclo[3.2.1]octyl-6-oxy)-1,2,5-thiadiazole
(±)-exo-3-Propythio-4-(2-methoxycarbonyl-2-azabicyclo[2.2.2]octyl-6-oxy)-1,2,5-thiadiazole
(±)-exo-3-Propylsulfonyl-4-(2-methoxycarbonyl-2-azabicyclo[2.2.2]octyl-6-oxy)-1,2,5-thiadiazole
(±)-exo-3-(4,4,4-Trifluorobutyloxy)-4-(2-methoxycarbonyl-2-azabicyclo[2.2.2]octyl-6-oxy)-1,2,5-thiadiazole
(±)-exo-3-(4,4,4-Trifluorobutyloxy)-4-(2-azabicyclo[2.2.2]octyl-6-oxy)-1,2,5-thiadiazole
(±)-exo-3-(Hexyloxy)-4-(2-azabicyclo[2.2.2]octyl-6-oxy)-1,2,5-thiadiazole
(±)-endo-3-(4,4,4-Trifluorobutyloxy)-4-(2-azabicyclo[2.2.2]octyl-6-oxy)-1,2,5-thiadiazole
(±)-exo-3-(2-[Fluorophenoxy]ethylthio)-4-(2-methoxycarbonyl-2-azabicyclo[2.2.2]octyl-6-oxy)-1,2,5-thiadiazole
(±)-exo-3-(2-[Fluorophenoxy]ethylthio)-4-(2-azabicyclo[2.2.2]octyl-6-oxy)-1,2,5-thiadiazole
(±)-endo-3-Propylthio-4-(1-azabicyclo[3.2.1]octyl-6-oxy)-1,2,5-thiadiazole
(±)-endo-3-Propylsulfonyl-4-(1-azabicyclo[3.2.1]octyl-6-oxy)-1,2,5-thiadiazole
(±)-endo-3-(4,4,4-Trifluorobutoxy)-4-(1-azabicyclo [3.2.1]octyl-6-oxy)-1,2,5-thiadiazole
(±)-endo-3-(2-Butynyloxy)-4-(1-azabicyclo[3.2.1]octyl-6-oxy)-1,2,5-thiadiazole
(±)-endo-3-(trans-2-Butenyloxy)-4-(1-azabicyclo[3.2.1]octyl-6-oxy)-1,2,5-thiadiazole
(±)-endo-3-(2-Methylthioethoxy)-4-(1-azabicyclo[3.2.1]octyl-6-oxy)-1,2,5-thiadiazole
(±)-endo-3-(2-(4-Methyl-1,3-thiazol-5-yl)ethoxy)-4-(1-azabicyclo[3.2.1]octyl-6-oxy)-1,2,5-thiadiazole
(±)-endo-3-(4-Methylthiobenzyloxy)-4-(1-azabicyclo[3.2.1]octyl-6-oxy)-1,2,5-thiadiazole
(±)-endo-3-(2-Thienylmethoxy)-4-(1-azabicyclo[3.2.1]octyl-6-oxy)-1,2,5-thiadiazole
(±)-endo-3-(2-Cyclohexenyloxy)-4-(1-azabicyclo[3.2.1]octyl-6-oxy)-1,2,5-thiadiazole
(±)-endo-3-(3-Pentynyloxy)-4-(1-azabicyclo[3.2.1]octyl-6-oxy)-1,2,5-thiadiazole
(±)-endo-3-(3-Hexynyloxy)-4-(1-azabicyclo[3.2.1]octyl-6-oxy)-1,2,5-thiadiazole
(±)-endo-3-(3-Chloropropoxy)-4-(1-azabicyclo[3.2.1]octyl-6-oxy)-1,2,5-thiadiazole
(±)-endo-3-[2-(2-Napthalyl)ethoxy]-4-(1-azabicyclo[3.2.1]octyl-6-oxy)-1,2,5-thiadiazole
(±)-endo-3-(4-Chloro-α-cyclopropyl-benzyloxy)-4-(1-azabicyclo[3.2.1]octyl-6-oxy)-1,2,5-thiadiazole
(±)-endo-3-(4-Methyl-3-pentenyloxy)-4-(1-azabicyclo[3.2.1]octyl-6-oxy)-1,2,5-thiadiazole
(±)-endo-3-(cis-2-Butenyloxy)-4-(1-azabicyclo[3.2.1]octyl-6-oxy)-1,2,5-thiadiazole
(±)-endo-3-(Cyclopropylmethoxy)-4-(1-azabicyclo[3.2.1]octyl-6-oxy)-1,2,5-thiadiazole
(±)-endo-3-(2-Methoxyethoxy)-4-(1-azabicyclo[3.2.1]octyl-6-oxy)-1,2,5-thiadiazole
(±)-endo-3-(3-Butenyloxy)-4-(1-azabicyclo[3.2.1]octyl-6-oxy)-1,2,5-thiadiazole
(±)-endo-3-(2-Cyclopropylethoxy)-4-(1-azabicyclo[3.2.1]octyl-6-oxy)-1,2,5-thiadiazole
(±)-endo-3-(3-Butynyloxy)-4-(1-azabicyclo[3.2.1]octyl-6-oxy)-1,2,5-thiadiazole
(±)-endo-3-(4,4,4,3,3,2,2-Heptafluorobutoxy)-4-(1-azabicyclo[3.2.1]octyl-6-oxy)-1,2,5-thiadiazole
(±)-endo-3-[2-(3-Trifluoromethylphenyl)ethoxy]-4-(1-azabicyclo[3.2.1]octyl-6-oxy)-1,2,5-thiadiazole
(±)-endo-3-[2-(2-Thienyl)ethoxy]-4-(1-azabicyclo[3.2.1]octyl-6-oxy)-1,2,5-thiadiazole
(±)-endo-3-(3,3,3,2,2,Pentafluoropropoxy)-4-(1-azabicyclo[3.2.1]octyl-6-oxy)-1,2,5-thiadiazole
(±)-endo-3-(2-Phenoxyethoxy)-4-(1-azabicyclo [3.2.1]octyl-6-oxy)-1,2,5-thiadiazole
(±)-endo-3-(4-n-Butylbenzyloxy)-4-(1-azabicyclo[3.2.1]octyl-6-oxy)-1,2,5-thiadiazole
(±)-endo-3-[3-(4-Methoxyphenyl)propoxy]-4-(1-azabicyclo [3.2.1]octyl-6-oxy)-1,2,5-thiadiazole
(±)-endo-3-(4-Fluorobenzyloxy)-4-(1-azabicyclo[3.2.1]octyl-6-oxy)-1,2,5-thiadiazole
(±)-endo-3-(2,4-Difluorobenzyloxy)-4-(1-azabicyclo[3.2.1]octyl-6-oxy)-1,2,5-thiadiazole
(±)-endo-3-[4-(Trifluoromethoxy)benzyloxy]-4-(1-azabicyclo[3.2.1]octyl-6-oxy)-1,2,5-thiadiazole
(±)-endo-3-(4-Fluorobutoxy)-4-(1-azabicyclo[3.2.1]octyl-6-oxy)-1,2,5-thiadiazole
(±)-endo-3-(4-tert-Butylbenzyloxy)-4-(1-azabicyclo[3.2.1]octyl-6-oxy)-1,2,5-thiadiazole
(±)-endo-3-(1-Cyclopropylethoxy)-4-(1-azabicyclo[3.2.1]octyl-6-oxy)-1,2,5-thiadiazole
(±)-endo-3-(2-Cyclohexylethoxy)-4-(1-azabicyclo[3.2.1]octyl-6-oxy)-1,2,5-thiadiazole
(±)-endo-3-(3-Methyl-2-butenyloxy)-4-(1-azabicyclo[3.2.1]octyl-6-oxy)-1,2,5-thiadiazole
(±)-endo-3-(4-Cyclohexylbutoxy)-4-(1-azabicyclo[3.2.1]octyl-6-oxy)-1,2,5-thiadiazole
(±)-endo-3-(3-Butyn-2-oxy)-4-(1-azabicyclo[3.2.1]octyl-6-oxy)-1,2,5-thiadiazole
(±)-endo-3-(3-Methyl-3-phenylbutoxy)-4-(1-azabicyclo[3.2.1]octyl-6-oxy)-1,2,5-thiadiazole
(±)-endo-3-(3-Fluoropropoxy)-4-(1-azabicyclo[3.2.1]octyl-6-oxy)-1,2,5-thiadiazole
(±)-endo-3-[3-(2-Thienyl)propoxy]-4-(1-azabicyclo[3.2.1]octyl-6-oxy)-1,2,5-thiadiazole
(±)-3-(2-[4-Fluorophenoxy]ethylthio)-4-(1-azabicyclo[2.2.2]octyl-3-oxy)-1,2,5-thiadiazole
(±)-3-(2-Methylthioethyl)-4-(1-azabicyclo[2.2.2]octyl-3-oxy)-1,2,5-thiadiazole
(±)-3-(1-Azabicyclo[2.2.2]octyl-3-oxy)-1,2,5-thiadiazole
(±)-3-Hexyl-4-(1-azabicyclo[2.2.2]octyl-3-oxy)-1,2,5-thiadiazole
3-Butylthio-4-hydroxy-1,2,5-thiadiazole
(±)-3-(2-[3-{1,2,5-Thiadiazoyloxy}]ethoxy)-4-(1-azabicyclo[2.2.2]octyl-3-oxy)-1,2,5-thiadiazole and
(±)Exo-3-Butylthio-4-(1-azabicyclo[2.2.1]heptyl-3-oxy)-1,2,5-thiadiazole.

Preferred compounds of Formula I are selected from the group consisting of:
(+/−)-3-butylthio-4-(azabicyclo[2.2.2]octyl-3-oxy)-1,2,5-oxadiazole, (+/−)-3-(2-butyloxy)-4-[(+/−)-3-azabicyclo[2.2.2]octyloxy)-1,2,5-oxadiazole, (+/−)-3-butyloxy-4-[endo-(+/−)-6-[1-azabicyclo[3.2.1]octyloxy)]-1,2,5-oxadiazole, 3-(2,2,3,3,4,4,4-heptaflurorobutyloxy)-4-[(+/−)-3-(1-azabicyclo[2.2.2]octyloxy)]-1,2,5-oxadiazole, 3-methoxy-4-(1-azabicyclo[2.2.2]octyl-3-oxy)-1,2,5- oxadiazole, 3-pentylthio-4-(1-azabicyclo[2.2.2]ocytl-3-oxy)-1,2,5-oxadiazole, trans-3-butyloxy-4-(2-dimethylaminocyclopentyloxy)-1,2,5-oxadiazole, 3-butylthio-4-(3-azetidinyloxy)-1,2,5-oxadiazole, 3-(3-N-(2-thiazolidonyl)propylthio)-4-(1-azabicyclo[2.2.2]octyl-3-oxy)-1,2,5-oxadiazole, 3-chloro-4-(1-azabicyclo[3.2.1]octyl-6-oxy)-1,2,5-oxadiazole, 3-(2-2-thio-5-trifluoromethylthienyl)ethylthio)-4-azabicyclo[2.2.2]octyl-3-oxy)-1,2,5-oxadiazole, 3-butylthio-4-[3-±-endo-(1-azabicyclo[2.2.1]heptyloxy)]-1,2,5-oxadiazole, 3-hexyloxy-4-[6-±-endo-(2-azabicyclo[2.2.2]ocyloxy)]-1,2,5-oxadiazole, 3-(4,4,4-trifluorobutylthio)-4-[2-±-exo-(7-azabicyclo[2.2.1]heptyloxy)]-1,2,5-oxadiazole, 3-(2-phenoxyethylthio)-4-[3-±-endo-(1-azabicyclo[3.2.1]octyloxy)]-1,2,5-oxadiazole, 3-(5-hexenyloxy)-4-[7-±-endo-(2-azabicyclo[2.2.1]heptyloxy)]-1,2,5-oxadiazole, 3-butyl-4-[5-(1-azabicyclo[3.2.1]octyloxy)]-1,2,5-oxadiazole, and 3-cyclobutylmethyl-4-[2-±-endo-(8-azabicyclo[3.2.1]octyloxy)]-1,2,5-oxadiazole.

Some prefered characteristics of compound of Formula I for the composition are:
A) W is S;
B) r is 1 or 2;
C) G is selected from het-1 and het-5;
D) G is unsaturated;
E) G is het-4;
F) G is an azabicycle having 7 ring carbon atoms and a nitrogen atom;
G) G is het-6;
H) r is 0;
I) R is selected from halogen, —$OR^5Y$, —$SR^5Y$, —$OR^5ZY$, —$SR^5ZY$, —$OR^5ZR^4$, —$SR^5ZR^4$, —$OR^4$, and —$SR^4$;
J) W is O;
K) m is 1;
L) n is 1;
M) p is 2;
N) G is het-3
O) G is het-2
P) a compound of Formula I
Q) a compound of Formula I
R) a compound of Formula I
wherein W is oxygen or sulphur;
R is selected from the group consisting of hydrogen, amino, halogen, $NHR^6$, $NR^6R^7$, $R^4$, —$OR^4$, —$SR^4$, —$SOR^4$, —$SO_2R^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl); $R^4$ is selected from the group consisting of $C_{1-15}$-alkyl, $C_{2-15}$-alkenyl, and $C_{2-15}$-alkynyl, each of which is optionally substituted with one or more independently selected from the group consisting of halogen(s), —$CF_3$, —CN, Y, phenyl and phenoxy wherein phenyl or phenoxy is optionally substituted with one or more selected from the group consisting of halogen, —CN, $C_{1-4}$-alkyl, $C_{1-4}$-alkoxy, —$OCF_3$, —$CF_3$, —$CONH_2$ and —$CSNH_2$; or
R is phenyl or benzyloxycarbonyl, each of which is optionally substituted with one or more substituents independently selected from the group consisting of halogen, —CN, $C_{1-4}$-alkyl, $C_{1-4}$-alkoxy, —$OCF_3$, —$CF_3$, —$CONH_2$ and —$CSNH_2$; or
R is selected from the group consisting of —$OR^5Y$, —$SR^5Y$, $OR^5$—Z—Y, —$SR^5ZY$, —O—$R^5$—Z—$R^4$ and —S—$R^5$—Z—$R^4$;
Z is oxygen or sulphur;
$R^5$ is selected from the group consisting of $C_{1-15}$-alkyl, $C_{2-15}$-alkenyl, and $C_{2-15}$-alkynyl;

Y is a 5 or 6 membered heterocyclic group; and

G is selected from one of the following azacyclic or azabicyclic ring systems:

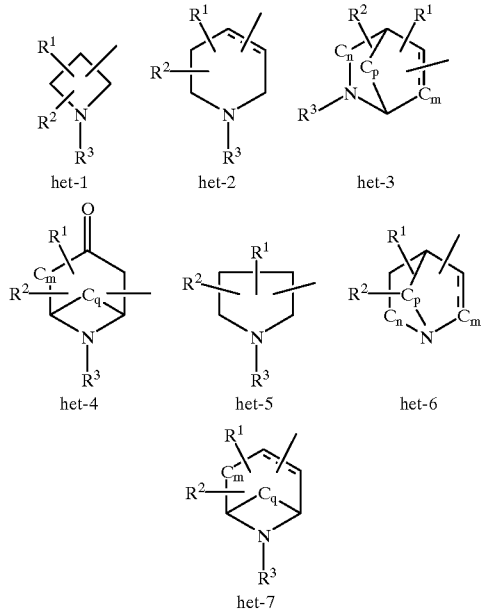

or G can optionally be substituted $C_3$-$C_8$ cycloalkyl wherein the substitution is —$NR^6R^7$;

$R^6$ and $R^7$ independently are selected from the group consisting of hydrogen and $C_{1-6}$-alkyl; or $R^6$ and $R^7$ together with the nitrogen atom optionally form a 4- to 6-member ring;

$R^1$ and $R^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with a subsituent independently selected from the group consisting of —OH, —$COR^{6'}$, $CH_2$—OH, halogen, —$NH_2$, carboxy, and phenyl;

$R^3$ is selected from the group consisting of hydrogen, $C_{1-5}$-alkyl, $C_{2-5}$-alkenyl and $C_{2-5}$-alkynyl;

$R^{6'}$ is selected from the group consisting of hydrogen and $C_{1-6}$-alkyl;

n is 0, 1 or 2;

m is 0, 1 or 2;

p is 0, 1 or 2;

q is 1 or 2;

r is 0, 1 or 2;

╌╌╌╌ is a single or double bond;

provided that when W is O and G is a saturated azabicyclic group having from 7 to 11 ring carbon atoms and a nitrogen atom wherein the nitrogen atom is separated from the W atom by 2 to 3 ring carbon atoms;

or a pharmaceutically acceptable salt or solvate thereof;

S) The G substituent is selected from the group consisting of

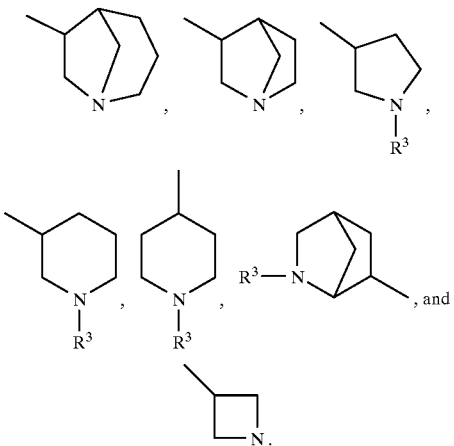

T) The G substituent is

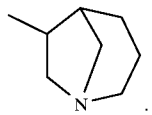

U) R is selected from the group consisting of —SR⁴', SOR⁴', —SO₂R⁴', substituted benzyloxycarbonyl wherein the substituents are one or more independently selected from the group consisting of —CN, —OCF₃, —CF₃, —CONH₂ and —CSNH₂; or $C_{3-10}$-cycloalkyl, $C_{4-12}$-(cycloalkylalkyl), —Z—$C_{3-10}$-cycloalkyl and —Z—$C_{4-12}$-(cycloalkylalkyl).

V) R is selected from the group consisting of $R^4$, $C_{3-10}$-cycloalkyl, $C_{4-12}$-(cycloalkylalkyl) , —Z—$C_{3-10}$-cycloalkyl and —Z—$C_{4-12}$-(cycloalkylalkyl); and —$R^4$ is selected from the group consisting of substituted $C_{5-15}$-alkyl, optionally substituted $C_{2-15}$-alkenyl, and optionally substituted $C_{2-15}$-alkynyl, wherein such substituent is one or more independently selected from the group consisting of halogen (s), —CF₃, —CN, Y, phenyl and phenoxy; wherein phenyl or phenoxy is optionally substituted with one or more substituents selected from the group consisting of halogen, —CN, $C_{1-4}$-alkyl, $C_{1-4}$-alkoxy, —OCF₃, —CF₃, —CONH₂ and —CSNH₂.

W) G is selected from the group consisting of het-4, het-7, het-6 wherein n=2; het-3 wherein one of n and m is 0 or 2; and het-3 wherein the I or I group is attached at the bridgehead of het-3.

Especially preferred compounds of this invention have the characteristics of A–F,P; A–F,Q; characteristics of A, G, H, M, F; characteristics of G–O,Q; or the characteristics of G–J,M,P; or G–J,M,Q. The characteristics of R and S may be particularly preferred.

Further, especially preferred R groups include phenyl, benzyloxycarbonyl, —OR⁵Y, —SR⁵Y, OR⁵—Z—Y, —SR⁵ZY, —O—R⁴—Z—R⁵ or —S—R⁴—Z—R⁵, —SOR⁴, $C_{3-10}$-cycloalkyl, $C_{4-12}$-(cycloalkylalkyl), —Z—$C_{3-10}$-cycloalkyl and —Z—$C_{4-12}$-(cycloalkylalkyl) wherein Z is oxygen or sulphur, $R^5$ is $C_{1-15}$-alkyl, $C_{2-15}$-alkenyl, $C_{2-15}$-alkynyl, Y is a 5 or 6 membered heterocyclic group containing one to four N, O or S atom(s) or a combination thereof, $R_4$ is $C_{1-15}$-alkyl, $C_{2-15}$-alkenyl, and $C_{2-15}$-alkynyl.

Further, especially preferred G groups include the following heterocycles:

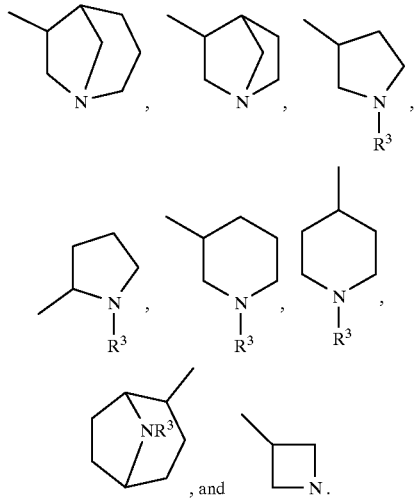

wherein the point of attachment to the —(CH₂)ᵣ—W— group is as indicated

Some particularly preferred G groups include

It is another preferred embodiment of this invention that G is not an azabicycle, particularly when W is oxygen.

Additionally, another embodiment of this invention which can be preferred is that when W is O and G is alkyl, R is not halogen.

The invention will now be described in further detail with reference to the following examples. Many compounds of Formula I' can be prepared using the methods and procedures illustrated by the following examples. The examples are provided for illustrative purposes, and are not to be construed as limiting the scope of the invention in any way. The NSAIDS can be purchased from commercial vendors or prepared using methods that are well known in the art.

EXAMPLE 1

3-Chloro-4-(1-butylthio)-1,2,5-thiadiazole

Cyanogen (36 g, 0.69 mol) was bubbled into ether (250 mL) maintained at −10° C. To the solution was added dropwise diethylamine (3 mL) followed by dropwise addition of 1-butylthiol (47 mL, 0.64 mol) at such a rate that the temperature did not exceed −5° C. The reaction was maintained below 0° C. for 5 h then stirred at ambient overnight. Ether was distilled from the reaction until the pot temperature reached 50° C. The reaction was cooled to ambient and then added dropwise to a solution of sulfur monochloride (55 mL, 0.688 mol) in DMF (50 mL) that was cooled to 5° C. Cooling was removed and reaction was stirred overnight. The reaction was cooled in an ice-water bath and excess sulfur monochloride destroyed by careful addition of $H_2O$ while maintaining the temperature below 40° C. The liquid was decanted from the semi-solid sulfur precipitant and the sulfur residue triturated with hexane. The aqueous fraction was extracted with hexane (3×) and the combined extracts and triturants were washed with $H_2O$, aqueous $NaHCO_3$, brine, dried, and the solvent evaporated. The residue was distilled at 2 mm Hg to give a yellow liquid (24.6 g), b.p. 105–110° C. (Compound 1).

EXAMPLE 2

3-Chloro-4-butylsulfonyl-1,2,5-thiadiazole

A solution of Oxone™ (12 g, 0.0195 mol) in $H_2O$ (60 mL) was vigorous stirred as 3-chloro-4-butylthio-1,2,5-thiadiazole (2.1 g, 0.01 mol) in THF (30 mL) was added dropwise. After 24 h, the THF was evaporated and the residue extracted with ether (3×). Extracts were washed with $H_2O$, dried, and solvent evaporated to give a clear liquid. Radial chromatography eluting with 30% EtOAc/hexane gave a colorless liquid (2.3 g). (Compound 2).

EXAMPLE 3

3-Chloro-4-ethylthio-1,2,5-thiadiazole

Cyanogen (36 g, 0.69 mol) was bubbled into ether (250 mL) maintained at −10° C. To the solution was added dropwise diethylamine (3 mL) followed by dropwise addition of ethanethiol (47 mL, 0.64 mol) at such a rate that the temperature did not exceed −5° C. The reaction was maintained below 0° C. for 5 h then stirred at ambient temperature overnight. Ether was distilled from the reaction until the pot temperature reached 50° C. The reaction was cooled to ambient and then added dropwise to a solution of sulfur monochloride (125 mL, 1.56 mol) in DMF (150 mL) that was cooled to 5° C. Cooling was removed and the reaction was stirred overnight. The reaction was cooled in an EtOH-ice bath as the excess sulfur monochloride was destroyed by dropwise addition of water while maintaining the temperature below 35° C. The liquid was decanted from the semi-solid sulfur precipitant and the sulfur residue triturated with hexane. The aqueous fraction was extracted with hexane (3×) and the combined extracts and triturants were washed with $H_2O$, aqueous $NaHCO_3$, brine, dried, and the solvent evaporated. The brown liquid residue was distilled at 3 mm Hg to give a yellow liquid (80.2 g), b.p. 91–96° C. (Compound 3).

EXAMPLE 4

3-Chloro-4-ethylsulfonyl-1,2,5-thiadiazole

A solution of Oxone (84 g, 0.137 mol) in $H_2O$ (400 mL) was rapidly stirred as 3-chloro-4-ethylthio-1,2,5-thiadiazole (12.2 g, 0.067 mol) in THF (200 mL) was added. After stirring overnight, the THF was evaporated and the residue extracted with ether (3×). The extracts were washed with $H_2O$, aqueous $NaHCO_3$, and brine then the solvent dried and evaporated to give a clear liquid (13.6 g). (Compound 4).

EXAMPLE 5

(±)-3-Methoxy-4-(1-azabicyclo[2.2.2]octyl-3-oxy)-1,2,5-thiadiazole

A solution of 1-azabicyclo[2.2.2]octan-3-ol (1.36 g, 0.0104 mol) in THF (20 mL) was treated dropwise with 1.6 M n-butyllithium in hexane (7.4 mL, 0.0118 mol). To this solution was added 3-methoxy-4-methanesulfonyl-1,2,5-thiadiazole (2.08 g, 0.0107 mol) in THF (40 mL), the reaction heated to 40° C. for 2 h, and then stirred at ambient temperature overnight. The solvent was evaporated, the residue acidified with 1 N HCl, and the mixture extracted with ether. The aqueous solution was made basic and extracted with EtOAc. The extracts were washed with $H_2O$, dried, and the solvent evaporated. The residue was purified by radial chromatography (2.5% EtOH-0.25% $NH_4OH$-$CHCl_3$) to give a clear oil. The HCl salt of the oil (0.85 g) crystallized from MeOH-EtOAc, m.p. 197–198° C. (Compound 5).

EXAMPLE 6

(±)-3-Ethoxy-4-(1-azabicyclo[2.2.2]octyl-3-oxy)-1,2,5-thiadiazole

A solution of 1-azabicyclo[2.2.2]octan-3-ol (0.75 g, 0.0059 mol) in THF (50 mL) was treated dropwise with 1.6 M n-butyllithium in hexane (3.7 mL, 0.0059 mol). To this solution was added 3-ethoxy-4-methanesulfonyl-1,2,5-thiadiazole (1.0 g, 0.0048 mol) in THF (12 mL) and the reaction heated to 60° C. for 5 h. The solvent was evaporated, the residue acidified with 1 N HCl, and the mixture extracted with ether. The aqueous solution was made basic and extracted with ether. The extracts were washed with $H_2O$, dried, and the solvent evaporated to give a clear oil. The HCl salt of the oil (0.47 g) crystallized from 2-propanol, m.p. 212–213° C. (Compound 6).

EXAMPLE 7

(±)-3-Propyloxy-4-(1-azabicyclo[2.2.2]octyl-3-oxy)-1,2,5-thiadiazole

A solution of 1-azabicyclo[2.2.2]octan-3-ol (1.1 g, 0.0087 mol) in THF (75 mL) was treated dropwise with 1.6 M n-butyllithium in hexane (5.0 mL, 0.008 mol). To this solution was added 3-propyloxy-4-methanesulfonyl-1,2,5-thiadiazole (1.3 g, 0.0059 mol) in THF (15 mL) and the reaction heated to 60° C. for 4 h. The solvent was evaporated, the residue acidified with 1 N HCl, and the mixture extracted with ether. The aqueous solution was made basic and extracted with EtOAc. The extracts were washed with $H_2O$, dried, and the solvent evaporated to give a clear oil. The HCl salt of the oil (0.59 g) crystallized from 2-propanol, m.p. 218–219° C. (Compound 7).

EXAMPLE 8

(±)-3-Butyloxy-4-(1-azabicyclo[2.2.2]octyl-3-oxy)-1,2,5-thiadiazole

A solution of 1-azabicyclo[2.2.2]octan-3-ol (2.2 g, 0.0168 mol) in THF (25 mL) was treated dropwise with 1.6 M n-butyllithium in hexane (10.8 mL, 0.0173 mol). To this solution was added 3-butyloxy-4-methanesulfonyl-1,2,5-thiadiazole (1.98 g, 0.084 mol) in THF (25 mL) and the reaction heated to 52° C. for 3.5 h. The solvent was evaporated, the residue acidified with 1 N HCl, and the mixture extracted with ether. The aqueous solution was made basic and extracted with EtOAc. The extracts were washed with $H_2O$, dried, and the solvent evaporated to give a clear oil. The HCl salt of the oil (2.0 g) crystallized from $CHCl_3$-EtOAc-ether, m.p. 204–205° C. (Compound 8).

EXAMPLE 9

(±)-3-Pentyloxy-4-(1-azabicyclo[2.2.2]octyl-3-oxy)-1,2,5-thiadiazole

A solution of 1-azabicyclo[2.2.2]octan-3-ol (0.75 g, 0.0059 mol) in THF (50 mL) was treated dropwise with 1.6 M n-butyllithium in hexane (3.7 mL, 0.0059 mol). To this solution was added 3-pentyloxy-4-methanesulfonyl-1,2,5-thiadiazole (1.0 g, 0.004 mol) in THF (10 mL) and the reaction heated to 60° C. for 4 h. The solvent was evaporated, the residue acidified with 1 N HCl, and the mixture extracted with ether. The aqueous solution was made basic and extracted with ether. The extracts were washed with $H_2O$, dried, and the solvent evaporated to give a clear oil. The HCl salt of the oil (0.75 g) crystallized from EtOAc, m.p. 171–172° C. (Compound 9).

EXAMPLE 10

(±)-3-Hexyloxy-4-(1-azabicyclo[2.2.2]octyl-3-oxy)-1,2,5-thiadiazole

A solution of 1-azabicyclo[2.2.2]octan-3-ol (2.2 g, 0.0168 mol) in THF (25 mL) was treated dropwise with 1.6 M n-butyllithium in hexane (10.8 mL, 0.0173 mol). To this solution was added 3-hexyloxy-4-methanesulfonyl-1,2,5-thiadiazole (2.2 g, 0.004 mol) in THF (25 mL) and the reaction heated to 52° C. for 3.5 h. The solvent was evaporated, the residue acidified with 1 N HCl, and the mixture extracted with ether. The aqueous solution was made basic and extracted with ether. The extracts were washed with $H_2O$, dried, and the solvent evaporated to give a clear oil. The HCl salt of the oil (1.76 g) crystallized from EtOAc, m.p. 165–166° C. (Compound 10).

EXAMPLE 11

(±)-3-(4-Methylpentyloxy)-4-(1-azabicyclo[2.2.2]-octyl-3-oxy)-1,2,5-thiadiazole

A solution of 1-azabicyclo[2.2.2]octan-3-ol (0.75 g, 0.0059 mol) in THF (50 mL) was treated dropwise with 1.6 M n-butyllithium in hexane (3.7 mL, 0.0059 mol). To this solution was added 3-(4-methylpentyloxy)-4-methanesulfonyl-1,2,5-thiadiazole (1.2 g, 0.0045 mol) in THF (10 mL) and the reaction heated to reflux for 6 h. The solvent was evaporated, the residue acidified with 1 N HCl, and the mixture extracted with ether. The aqueous solution was made basic and extracted with ether. The extracts were washed with $H_2O$, dried, and the solvent evaporated to give a clear oil. The HCl salt of the oil (1.1 g) crystallized from EtOAc, m.p. 179–180° C. (Compound 11).

EXAMPLE 12

(±)-3-Chloro-4-(1-azabicyclo[2.2.2]octyl-3-oxy)-1,2,5-thiadiazole

A solution of 1-azabicyclo[2.2.2]octan-3-ol (1.1 g, 0.0084 mol) in THF (25 mL) was treated dropwise with 1.6 M n-butyllithium in hexane (5.4 mL, 0.0086 mol). This solution was added dropwise to a solution of 3-chloro-4-butylsulfonyl-1,2,5-thiadiazole (2.1 g, 0.0086 mol) in THF (15 mL) at such a rate that the temperature did not exceed 32° C. After stirring for 3 days, the reaction was treated with $H_2O$ (10 mL), diluted with ether (100 mL), and extracted with 1 N HCl (25 mL). The aqueous solution was washed with ether, made basic, and extracted with ether. The extracts were dried, the solvent evaporated, and the residue purified by radial chromatography (2.5% EtOH-0.25% $NH_4OH$—$CHCl_3$) to give a straw colored liquid (1.1 g). The oxalate salt (0.39 g) crystallized from MeOH-EtOAc, m.p. 154–156° C. (Compound 12).

Alternative Synthesis of (±)-3-Chloro-4-(1-azabicyclo[2.2.2]octyl-3-oxy)-1,2,5-thiadiazole A solution of 1-azabicyclo[2.2.2]octan-3-ol (1.2 g, 0.0092 mol) in THF (25 mL) was treated dropwise with 1.6 M n-butyllithium in hexane (5.9 mL, 0.0095 mol). The solution was cooled to −8° C. and a solution of 3-chloro-4-ethylsulfonyl-1,2,5-thiadiazole (1.83 g, 0.0086 mol) in THF (15 mL) was added dropwise. After 15 min, cooling was removed and the reaction stirred overnight. The reaction was treated with $H_2O$ (10 mL), diluted with ether (100 mL), and extracted with 1 N HCl (25 mL). The aqueous solution was washed with ether, made basic, and extracted with ether. The extracts were dried and the solvent evaporated to give crude (compound 12) (1.05 g) as a brownish liquid.

Alternative Synthesis of (±)-3-Chloro-4-(1-azabicyclo[2.2.2]octyl-3-oxy)-1,2,5-thiadiazole A mixture of 1-azabicyclo[2.2.2]octan-3-ol (12.7 g, 0.1 mol), triethylamine (0.3 mL), and $CHCl_3$ (150 mL) was cooled to 5° C. and cyanogen (7.25 g, 0.139 mol) bubbled into the mixture. The reaction was stirred another hour then allowed to come to ambient temperature overnight. The solvent was evaporated, the residue dissolved in DMF (20 mL), and the solution added dropwise to a solution of $S_2Cl_2$ (47.3 g, 0.35 mol) in DMF (30 mL) that was cooled in an ice-water bath. After addition, cooling was removed and reaction exothermed to 32° C. After 5 h, reaction cooled and excess $S_2Cl_2$ destroyed by careful addition of $H_2O$. The reaction was diluted with more $H_2O$ (300 mL) and the aqueous solution decanted from the sulfur residue. The sulfur residue was triturated with $H_2O$ and the combined aqueous solutions evaporated to a small volume (150 mL). The solution was washed with ether and then made basic with 50% NaOH while maintaining the temperature below 30° C. The mixture was extracted with $CHCl_3$, the extracts dried, and the solvents thoroughly evaporated. The residue was suspended in ether, dried, filtered and the solvent evaporated to give (compound 12) (18.1 g) as a yellow oil that slowly solidified.

EXAMPLE 13

(±)-3-Propylthio-4-(1-azabicyclo[2.2.2]octyl-3-oxy)-1,2,5-thiadiazole

A solution of the crude compound 12 (1.67 g, 0.0068 mol) in DMF (25 mL) was treated portionwise with freshly ground flaked $Na_2S$-$9H_2O$ (1.8 g, 0.0075 mol). After 40 min, 1-bromopropane (1.25 g, 0.010 mol) was added and the reaction stirred overnight. The solvent was evaporated, the residue was acidified with 1 N HCl, and the mixture extracted with ether. The aqueous was made basic and extracted with ether. The extracts were dried and the solvent evaporated to give a straw-colored liquid. The HCl salt (1.28

EXAMPLE 14

(±)-3-Butylthio-4-(1-azabicyclo[2.2.2]octyl-3-oxy)-1,2,5-thiadiazole

A solution of the crude compound 12 (1.8 g, 0.0073 mol) in DMF (25 mL) was treated portionwise with freshly ground flaked $Na_2S-9H_2O$ (1.94 g, 0.0081 mol). After 1 h, 1-iodobutane (2 g, 0.011 mol) was added and the reaction stirred overnight. The solvent was evaporated, the residue was acidified with 1 N HCl, and the mixture extracted with ether. The aqueous was made basic and extracted with ether. The extracts were dried and the solvent evaporated to give a straw-coloured liquid. The HCl salt (1.82 g) crystallized from $CHCl_3$-EtOAc-ether, m.p. 151–153° C. (Compound 14).

EXAMPLE 15

(±)-3-Pentylthio-4-(1-azabicyclo[2.2.2]octyl-3-oxy)-1,2,5-thiadiazole

A solution of the crude compound 12 (1.67 g, 0.0068 mol) in DMF (25 mL) was treated portionwise with freshly ground flaked $Na_2S-9H_2O$ (1.8 g, 0.0075 mol). After 1 h, 1-bromopentane (1.53 g, 0.010 mol) was added and the reaction stirred overnight. The solvent was evaporated, the residue was acidified with 1 N HCl, and the mixture extracted with ether. The aqueous was made basic and extracted with ether. The extracts were dried and the solvent evaporated to give a straw-coloured liquid. The HCl salt (1.07 g) crystallized from $CHCl_3$-EtOAc-ether, m.p. 186–187° C. (Compound 15).

EXAMPLE 16

(S)-3-Pentylthio-4-(1-azabicyclo[2.2.2]octyl-3-oxy)-1,2,5-thiadiazole

A solution of (S)-1-azabicyclo[2.2.2]octan-3-ol (2.0 g, 0.0157 mol) in THF (40 mL) was cooled to 10° C. as 1.6 M n-butyllithium in hexane (10 mL, 0.016 mol) was added dropwise. The resulting mixture was treated with 3-chloroethylsulfonyl-1,2,5-thiadiazole (3.34 g, 0.0157 mol) in THF (25 mL) and stirred for 16 h. The reaction was treated with $H_2O$ (10 mL), ether (170 mL) and extracted with 1 N HCl (43 mL). The aqueous fraction was washed with ether, made basic, and extracted with ether. The extracts were dried and the solvent evaporated to give an oil (1.7 g). The oil was dissolved in DMF (25 mL), treated portionwise with freshly ground flaked $Na_2S-9H_2O$ (1.83 g, 0.0076 mol), and heated (40° C.). After 1.25 h, 1-bromopentane (1.58 g, 0.0105 mol) was added and the reaction stirred overnight. The solvent was evaporated, the residue was acidified with 1 N HCl, and the mixture extracted with ether. The aqueous was made basic and extracted with ether. The extracts were dried and the solvent evaporated to give a straw-colored liquid that was purified by radial chromatography (5% EtOH-0.5% $NH_4OH$-$CHCl_3$). The HCl salt (0.87 g) crystallized from $CHCl_3$-EtOAc-ether, m.p. 194–195° C., $[\alpha]_D$= 25.41° (EtOH). (Compound 16).

EXAMPLE 17

(±)-3-Hexylthio-4-(1-azabicyclo[2.2.2]octyl-3-oxy)-1,2,5-thiadiazole

A solution of the crude compound 12 (1.8 g, 0.0073 mol) in DMF (25 mL) was treated portionwise with freshly ground flaked $Na_2S-9H_2O$ (1.94 g, 0.0081 mol). After 1 h, 1-iodohexane (2.3 g, 0.011 mol) was added and the reaction stirred overnight. The solvent was evaporated, the residue was acidified with 1 N HCl, and the mixture extracted with ether. The aqueous was made basic and extracted with ether. The extracts were dried and the solvent evaporated to give a straw-colored liquid. The HCl salt (1.0 g) crystallized from $CHCl_3$-EtOAc-ether, m.p. 165–167° C. (Compound 17).

EXAMPLE 18

(±)-3-(3,3-Dimethylbutylthio)-4-(1-azabicyclo [2.2.2]-octyl-3-oxy)-1,2,5-thiadiazole A solution of the crude (compound 12) (1.05 g, 0.0043 mol) in DMF (25 mL) was treated portionwise with freshly ground flaked $Na_2S-9H_2O$ (1.24 g, 0.0051 mol). After 1 h, 1-bromo-3,3-dimethylbutane (1.18 g, 0.007 mol) was added and the reaction stirred overnight. The solvent was evaporated, the residue was acidified with 1 N HCl, and the mixture extracted with ether. The aqueous was made basic and extracted with ether. The extracts were dried and the solvent evaporated to give a straw-colored liquid. The HCl salt (0.41 g) crystallized from $CHCl_3$-EtOAc-ether, m.p. 189–190° C. (Compound 18).

EXAMPLE 19

(±)-3-(2-(2-Thienylthio)ethylthio)-4-(1-azabicyclo-[2.2.2]octyl-3-oxy)-1,2,5-thiadiazole A solution of the crude (compound 12) (1.0 g, 0.0041 mol) in DMF (25 mL) was treated portionwise with freshly ground flaked $Na_2S-9H_2O$ (1.1 g, 0.0045 mol). After 1 h, 1-chloro-2-(2-thienylthio)ethane (1.1 g, 0.0062 mol) was added and the reaction stirred overnight. The solvent was evaporated, the residue was acidified with 1 N HCl, and the mixture extracted with ether. The aqueous was made basic and extracted with ether. The extracts were dried, the solvent evaporated, and the residue purified by flash chromatography (10% EtOH-1% $NH_4OH$-$CHCl_3$) to give a liquid. The HCl salt (0.88 g) crystallized from ether, m.p. 179.5–181° C. (Compound 19).

EXAMPLE 20

(±)-3-(2,2,3,3,3-Pentafluoropropylthio)-4-(1-azabicyclo-[2.2.2]octyl-3-oxy)-1,2,5-thiadiazole A solution of the crude (compound 12) (0.5 g, 0.002 mol) in DMF (15 mL) was treated portionwise with freshly ground flaked $Na_2S-9H_2O$ (0.53 g, 0.0022 mol). After 1 h, 1-methanesulfonoxy-2,2,3,3,3-pentafluoropropane (0.003 mol) was added and the reaction stirred overnight. The solvent was evaporated, the residue was acidified with 1 N HCl, and the mixture extracted with ether. The aqueous was made basic and extracted with ether. The extracts were dried, the solvent evaporated, and the residue purified by flash chromatography (5% EtOH-0.5% $NH_4OH$-$CHCl_3$) to give a liquid. The HCl salt (0.016 g) crystallized from ether, m.p. 138–140° C. (Compound 20).

EXAMPLE 21

(±)-3-(3-(2-Thienyl)propylthio)-4-(1-azabicyclo [2.2.2]-octyl-3-oxy)-1,2,5-thiadiazole A solution of the crude (compound 12) (0.6 g, 0.0024 mol) in DMF (15 mL) was treated portionwise with freshly ground flaked $Na_2S-9H_2O$ (0.6 g, 0.0027 mol). After 1 h, 1-chloro-3-(2-thienyl)propane (0.6 g, 0.0036 mol) was added and the reaction stirred overnight. The solvent was evaporated, the residue was acidified with 1 N HCl, and the mixture extracted with ether. The aqueous was made basic and extracted with ether. The extracts were dried, the solvent evaporated, and the residue purified by flash chromatography (10% EtOH-1% NH$_4$OH-CHCl$_3$) to give a liquid. The HCl salt (0.16 g) crystallized from EtOH-EtOAc, m.p. 194–196° C. (Compound 21).

EXAMPLE 22

(±)-3-Butylthio-4-((1-azabicyclo[2.2.2]octan-3-yl)-methoxy)-1,2,5-thiadiazole

A solution of 3-hydroxymethyl-1-azabicyclo[2.2.2]octane (1.4 g, 0.01 mol) in THF (30 mL) was treated with 1.6 M n-butyllithium in hexane (6.5 mL, 0.0104 mol). The mixture was cooled to 10° C, and 3-chloro-4-ethylsulfonyl-1,2,5-thiadiazole (2.21 g, 0.0104 mol) in THF (10 mL) was added dropwise. Cooling was removed and the reaction stirred overnight. The reaction was treated with H$_2$O, diluted with ether, and extracted with 1 N HCl (25 mL). The acidic extracts were washed with ether, made basic, and extracted with ether. The extracts were dried and the solvent evaporated to give an orange liquid (1.82 g). The liquid was dissolved in DMF (32 mL) and treated with freshly ground flaked Na$_2$S-9H$_2$O (2.5 g, 0.0104 mol) in portions. After 55 min, the reaction was treated with 1-iodobutane (2.6 g, 0.014 mol) and warmed to 44° C. overnight. The solvent was evaporated, the residue acidified with 1 N HCl, and the mixture extracted with EtOAc-ether (1:1). The aqueous fraction was made basic and extracted with ether. The ether was dried, the solvent evaporated, and the residue purified by radial chromatography (5% EtOH-0.5% NH$_4$OH-CHCl$_3$) to give a liquid. The HCl salt (0.84 g) crystallized from EtOAc-ether, m.p. 170–171° C. (Compound 22).

EXAMPLE 23

(±)-exo-3-Pentylthio-4-(1-azabicyclo[3.2.1]octyl-6-oxy)-1,2,5-thiadiazole and (±)-Endo-3-pentylthio-4-(1-azabicyclo[3.2.1]-octyl-6-oxy)-1,2,5-thiadiazole A solution of the endo/exo mixture of 1-azabicyclo[3.2.1]octan-6-ol (1.95 g, 0.0153 mol, ref. Sternbach, L. H.; Kaiser, S. *J. Amer. Chem. Soc.* 1952, 74, 2215–2218.) in THF (25 mL) was treated with 1.6 M n-butyllithium in hexane (9.6 mL, 0.0153 mol). When the mixture had cooled to ambient temperature, 3-chloro-4-ethylsulfonyl-1,2,5-thiadiazole (2.96 g, 0.014 mol) in THF (15 mL) was added dropwise and the reaction stirred overnight. The reaction was treated with H$_2$O, diluted with ether, and extracted with 1 N HCl (32 mL). The acidic extract was made basic, extracted with ether, the extracts dried, and the solvent evaporated to give an orange liquid (1.25 g). The liquid was dissolved in DMF (25 mL) and treated with freshly ground flaked Na$_2$S-9H$_2$O (1.82 g, 0.0076 mol) in portions. After 40 min, 1-bromopentane (1.55 g, 0.0103 mol) was added and the reaction stirred overnight. The solvent was evaporated, the residue acidified, and the mixture extracted with ether. The aqueous fraction was made basic, extracted with ether, the extracts dried, and the solvent evaporated. The residue was purified by radial chromatography (2.5% EtOH-0.25% NH$_4$OH-CHCl$_3$) to first elute the exo isomer as a liquid. The HCl salt (0.26 g), crystallized from EtOAc, m.p. 159–160° C. (Compound 23). Further elution provided the endo isomer as a liquid. The HCl salt (0.23 g) crystallized from EtOAc, m.p. 190–193° C. (Compound 24).

EXAMPLE 24

(±)-endo-3-Butyloxy-4-(1-azabicyclo[2.2.1]heptyl-3-oxy)-1,2,5-thiadiazole

A solution of a mixture of (±)-endo and (±)-exo-1-azabicyclo[2.2.1]heptan3-ol (0.5 g, 0.0044 mol)(Ref. *J. Org. Chem.* 1969, 34, 3674–3676) in THF (20 mL) was cooled in an ice-water bath and treated dropwise with 1.6 M n-butyllithium in hexane (2.8 mL, 0.0044 mol). Cooling was removed, 3-butyloxy-4-methanesulfonyl-1,2,5-thiadiazole (1.4 g, 0.0059 mol) was added, and the reaction heated to reflux for 6 h. The solvent was evaporated, the residue acidified with 1 N HCl, and the mixture extracted with ether. The aqueous solution was made basic and extracted with EtOAc. The extracts were washed with H$_2$O, dried, and the solvent evaporated to give a clear oil. Radial chromatography (5% EtOH, 0.5% NH$_4$OH, CHCl$_3$) eluted the title compound as the more polar of the two UV active spots. The HCl salt of the title compound (0.5 g) crystallized from EtOAc with a quarter mole of H$_2$O, m.p. 161.5–163° C. (Compound 25).

EXAMPLE 25

(±)-Exo-3-butyloxy-4-(1-azabicyclo[2.2.1]heptyl-3-oxy)-1,2,5-thiadiazole

Rechromatography of the mixed fractions from the isolation of (compound 25) (5% EtOH, 0.5% NH$_4$OH, CHCl$_3$) gave the less polar UV active material. The HCl salt (0.036 g) crystallized from EtOAc with a quarter mole of water, m.p. 156–157° C. (Compound 26).

EXAMPLE 26

(±)-3-Butyloxy-4-(3-pyrrolidinyloxy)-1,2,5-thiadiazole

A suspension of NaH (0.066 g, 0.0028 mol) in THF (25 mL) was treated with 1-t-butylcarbamoyl-3-hydroxypyrrolidine (Ref. *Syn. Commun.* 15, 587.) (0.5 g, 0.0027 mol) and the reaction warmed to 50° C. for 30 min. After cooling to ambient temperature, 3-butyloxy-4-methanesulfonyl-1,2,5-thiadiazole (0.55 g, 0.0027 mol) in THF (5 mL) was added and the reaction heated to reflux for 2.5 h. The solvent was evaporated, the residue treated with ice-water, and the mixture extracted with ether. The extracts were washed with brine, dried, and the solvent evaporated. The residue was dissolved in ether (50 mL) and treated with a slow stream of HCl for 5 min. After stirring overnight, the reaction was extracted with cold water. The aqueous was washed with ether, made basic, and extracted with EtOAc. The extracts were washed with brine, dried, and the solvent evaporated to give a clear oil. The HCl salt (0.42 g) crystallized from EtOAc, m.p. 127–128° C. (Compound 27).

EXAMPLE 27

(±)-3-Butyloxy-4-(1-methyl-3-pyrrolidinyloxy)-1,2,5-thiadiazole

A solution of 1-methyl-3-pyrrolidinol (0.6 g, 0.0059 mol) in THF (20 mL) was treated with 1.6 M n-butyllithium in hexane (3.1 mL), 0.005 mol). To the solution was added 3-butyloxy-4-methanesulfonyl-1,2,5-thiadiazole (1.0 g, 0.0042 mol) and the reaction heated to reflux overnight. The solvent was evaporated, the residue acidified with cold 1 N HCl, and the mixture extracted with ether. The aqueous fraction was made basic, extracted with EtOAc, and the extracts washed with water. The extracts were dried and the solvent evaporated to give a liquid. The HCl salt (0.7 g) crystallized from EtOAc, m.p. 157–158° C. (Compound 28).

EXAMPLE 28

(±)-3-Butylthio-4-(1-methyl-3-piperidyloxy)-1,2,5-thiadiazole

A solution of 3-hydroxy-1-methylpiperidine (1.12 g, 0.0095 mol) in THF (25 mL) was treated with 1.6 M n-butyllithium in hexane (5.9 mL, 0.0095 mol). The mixture was cooled to 8° C. and treated dropwise with 3-chloro-4-ethylsulfonyl-1,2,5-thiadiazole (1.83 g, 0.0086 mol) in THF (20 mL). The cooling was removed and the reaction stirred overnight. The mixture was treated with $H_2O$, acidified with 1 N HCl and diluted with ether. The aqueous fraction was washed with ether, made basic, and extracted with ether. The extracts dried and solvent evaporated to give a brown liquid (1.95 g). The liquid was dissolved in DMF (38 mL) and treated with freshly ground flaked $Na_2S \cdot 9H_2O$ (2.98 g, 0.0124 mol) in portions. After 1 h, the mixture was treated with 1-iodobutane (3.1 g, 0.0169 mol) and stirred 64 h. The solvent was evaporated, the residue acidified with 1 N HCl, and the mixture extracted with ether. The aqueous solution was made basic and extracted with ether. The extracts were dried and the solvent evaporated to give an orange liquid. Purification by radial chromatography (2.5% EtOH-0.25% $NH_4OH$-$CHCl_3$) gave a liquid whose HCl salt (1.4 g) crystallized from $CHCl_3$-EtOAc-ether, m.p. 141°142° C. (Compound 29).

EXAMPLE 29

3-Butylthio-4-(1-methyl-4-piperidyloxy)-1,2,5-thiadiazole

A solution of 4-hydroxy-1-methylpiperidine (1.12 g, 0.0095 mol) in THF (25 mL) was treated with 1.6 M n-butyllithium in hexane (5.9 mL, 0.0095 mol). The mixture was cooled to 8° C. and treated dropwise with 3-chloro-4-ethylsulfonyl-1,2,5-thiadiazole (1.83 g, 0.0086 mol) in THF (20 mL). The cooling was removed and the reaction stirred overnight. The mixture was treated with $H_2O$, acidified with 1 N HCl, and diluted with ether. The aqueous fraction was washed with ether, made basic, and extracted with ether. The extracts dried and solvent evaporated to give a brown liquid (1.52 g). The liquid was dissolved in DMF (30 mL) and treated with freshly ground flaked $Na_2S \cdot 9H_2O$ (2.32 g, 0.0097 mol) in portions. After 50 min, the mixture was treated with 1-iodobutane (2.4 g, 0.013 mol) and stirred for 63 h. The solvent was evaporated, the residue acidified with dilute HCl, and the mixture extracted with ether. The aqueous fraction was made basic and extracted with ether. The extracts were dried and the solvent evaporated to give 1.3 g liquid. The HCl salt (1.3 g) crystallized from EtOAc-ether, m.p. 140–142° C. (Compound 30).

EXAMPLE 30

(S)-3-Butyloxy-4-(1-methyl-2-pyrrolidinylmethoxy)-1,2,5-thiadiazole

A solution of (S)-1-methyl-2-pyrrolidinemethanol (0.86, 0.0075 mol) in THF (20 mL) was treated with 1.6M n-butyllithium in hexane (4.7 mL, 0.0075 mol). To the solution was added 3-butyloxy-4-methanesulfonyl-1,2,5-thiadiazole (1.2 g, 0.005 mol) and the reaction heated to reflux for 6.5 h. The solvent was evaporated, the residue acidified with cold 1N HCl, and the mixture extracted with ether. The aqueous was made basic and extracted with EtOAc. The extracts were washed with water, dried, and the solvent evaporated to give a liquid. The HCl salt (0.72 g) crystallized from EtOAc, m.p. 115–116° C. (Compound 31).

EXAMPLE 31

(S)-3-Butyloxy-4-(2-pyrrolidinylmethoxy)-1,2,5-thiadiazole

A solution of (S)-1-butyloxycarbonyl-2-pyrrolidinemethanol (1.21, 0.006 mol) in THF (5 mL) was added to a suspension of 60% NaH in oil (0.24 g, 0.006 mol) in THF (30 mL). After 1 h, the mixture was heated to gentle reflux for 1 h. To the solution was added 3-butyloxy-4-methanesulfonyl-1,2,5-thiadiazole (1 g, 0.0042 mol) and the reaction heated to reflux overnight. The solvent was evaporated, the residue treated with cold $H_2O$, and the mixture extracted with EtOAc. The extracts were dried and treated with a stream of dry HCl for 3 min. After another hour, the solvent was evaporated, the residue treated with cold $H_2O$, and the mixture extracted with ether. The aqueous fraction was made basic and extracted with EtOAc. The extracts were washed with water, dried, and the solvent evaporated to give a liquid. The HCl salt (0.72 g) crystallized from EtOAc, m.p. 99–100° C. (Compound 32).

EXAMPLE 32

3-Butyloxy-4-(2-(dimethylamino)ethoxy)-1,2,5-thiadiazole

A solution of 2-dimethylaminoethanol (0.67 g, 0.0075 mol) in THF (20 mL) was treated with 1.6M n-butyllithium in hexane (4.7 mL, 0.0075 mol). To the solution was added 3-butyloxy-4-methanesulfonyl-1,2,5-thiadiazole (1.2 g, 0.005 mol) and the reaction heated to reflux for 6 h. The solvent was evaporated, the residue acidified with cold 1N HCl, and the mixture extracted with ether. The aqueous was made basic and extracted with EtOAc. The extracts were washed with water, dried, and the solvent evaporated to give a clear oil. The HCl salt (0.94 g) recrystallized from EtOAc to give a white solid, m.p. 97–98° C. (Compound 33).

EXAMPLE 33

3-Butylthio-4-(2-(diethylamino)ethoxy)-1,2,5-thiadiazole

A solution of 2-diethylaminoethanol (1.11 g, 0.0095 mol) in THF (25 mL) was treated with 1.6M n-butyllithium in hexane (5.9 mL, 0.0095 mol). The mixture was cooled to 8° C. and treated dropwise with 3-chloro-4-ethylsulfonyl-1,2, 5thiadiazole (1.83 g, 0.0086 mol) in THF (20 mL). The cooling was removed and the reaction stirred overnight. The mixture was treated with $H_2O$, acidified with 1N HCl, and diluted with ether. The aqueous fraction was washed with ether, made basic, and extracted with ether. The extracts dried and solvent evaporated to give a brown liquid (1.6 g). The liquid was dissolved in DMF (30 mL) and treated with freshly ground flaked $Na_2S \cdot 9H_2O$ (2.43 g, 0.010 mol) in portions. After 50 min, the mixture was treated with 1-iodobutane (2.52 g, 0.0137 mol) and stirred for 46 h. The solvent was evaporated, the residue acidified with dilute HCl, and the mixture extracted with ether. The aqueous fraction was made basic and extracted with ether. The extracts were dried, the solvent evaporated, and the residue purified by radial chromatography (5% EtOH-0.5%

NH$_4$OH-CHCl$_3$) to give a liquid. The HCl salt (1.15 g) crystallized from EtOAc-ether, m.p. 95–97° C. (Compound 34).

EXAMPLE 34

3-Butyloxy-4-(2-(trimethylamino)ethoxy)-1,2,5-thiadiazole iodide

A solution of (compound 33) (from 0.5 g, 0.0018 mol of the HCl salt) in EtOAc (30 mL) was treated with CH$_3$I (0.3 mL) and stirred overnight. The precipitant was collected, washed with EtOAc, and dried to give a white solid (0.64 g), m.p. 137–138° C. (Compound 35).

EXAMPLE 35

3-Butyloxy-4-(2-(dimethylamino)ethylthio)-1,2,5-thiadiazole

A suspension of 2-dimethylaminoethanthiol hydrochloride (0.57 g, 0.004 mol) in THF (25 mL) was treated with 1.6M n-butyllithium in hexane (5 mL, 0.008 mol). To the solution was added 3-butyloxy-4-methanesulfonyl-1,2,5-thiadiazole (0.71 g, 0.003 mol) and the reaction heated to reflux for 2 h followed by stirring at ambient temperature overnight. The solvent was evaporated, the residue acidified with cold 1N HCl, and the mixture extracted with ether. The aqueous was made basic and extracted with ether. The extracts were washed with water, dried, and the solvent evaporated. The residue was purified by radial chromatography (5% EtOH-0.5% NH$_4$OH-CHCl$_3$) to give a tan liquid. The HCl salt (0.22 g) recrystallized from EtOAc to give a white solid, m.p. 108–109° C. (Compound 36).

EXAMPLE 36

3-Chloro-4-(1-propylthio)-1,2,5-thiadiazole

Cyanogen (34 g, 0.65 mol) was bubbled into ether (250 mL) maintained at −10° C. To the solution was added dropwise diethylamine (3 mL) followed by dropwise addition of 1-propanethiol (57 mL, 0.63 mol) in ether (25 mL) at such a rate that the temperature did not exceed −5° C. After 5 h, cooling was removed and the reaction stirred overnight. Ether was distilled from the reaction until the pot temperature reached 50° C. The reaction was cooled to ambient and added dropwise to a solution of sulfur monochloride (125 mL, 1.56 mol) in DMF (125 mL) that was cooled in an ice-water bath. Cooling was removed and the reaction allowed to exotherm to 35° C., recooled to below 30° C., then stirred overnight. The reaction was cooled in EtOH-ice and the excess sulfur monochloride carefully destroyed by dropwise addition of H$_2$O (200 mL) such that the temperature did not exceed 30° C. The mixture was extracted with hexane, the extracts washed with brine, dried, and the solvent evaporated. The residue was distilled at 1.5 mm Hg to give a yellow liquid (98.6 g), b.p. 84–94° C. (Compound 37).

EXAMPLE 37

(R)-3-Pentylthio-4-(1-azabicyclo[2.2.2]octyl-3-oxy)-1,2,5-thiadiazole

A solution of (R)-1-azabicyclo[2.2.2]octan-3-ol (3.0 g, 0.0236 mol) in THF (40 mL) was cooled to 10° C. as 1.6M n-butyllithium in hexane (15 mL, 0.024 mol) was added dropwise. The resulting mixture was treated with 3-chloro-4-ethylsulfonyl-1,2,5-thiadiazole (5.01 g, 0.0236 mol) in THF (5 mL) and stirred for 22 h. The reaction was treated with H$_2$O (10 mL), ether (170 mL) and extracted with 1N HCl (35 mL). The aqueous fraction was washed with ether, made basic, and extracted with ether. The extracts were dried and the solvent evaporated to give an oil (2.35 g). The oil was dissolved in DMF (35 mL), treated portionwise with freshly ground flaked Na$_2$S-9H$_2$O (2.53 g, 0.0105 mol), and heated (40° C). After 1.25 h, 1-bromopentane (2.18 g, 0.0145 mol) was added and the reaction stirred overnight at 38° C. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH-CHCl$_3$). The HCl salt (1.68 g) crystallized from CHCl$_3$-EtOAc, m.p. 195–196° C., [α]$_D$=−24.6° (EtOH). (Compound 38).

EXAMPLE 38

(±)-3-(4-Methylpentylthio)-4-(1-azabicyclo[2.2.2]octyl-3-oxy)-1,2,5-thiadiazole A solution of the crude (compound 12) (1.65 g, 0.0067 mol) in DMF (25 mL) was treated portionwise with freshly ground flaked Na$_2$S-9H$_2$O (1.83 g, 0.0076 mol). After 1 h, 1-bromo-4-methylpentane (1.73 g, 0.0105 mol) was added and the reaction stirred three days at 40° C. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH-CHCl$_3$). The HCl salt (0.74 g) crystallized from CHCl$_3$-EtOAc-ether, m.p. 183–185° C. (Compound 39).

EXAMPLE 39

(±)-3-(3-Phenylpropylthio)-4-(1-azabicyclo[2.2.2]octyl-3-oxy)-1,2,5-thiadiazole A solution of the crude (compound 12) (0.9 g, 0.0037 mol) in DMF (25 mL) was treated portionwise with freshly ground flaked Na$_2$S-9H$_2$O (0.97 g, 0.004 mol). After 1 h, 1-bromo-3-phenylpropane (1.11 g, 0.056 mol) was added and the reaction stirred 17 h at 50° C. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (2.5% EtOH-0.25% NH$_4$OH-CHCl$_3$). The HCl salt (0.42 g) crystallized from CHCl$_3$-EtOAc-ether, m.p. 210–212° C. (Compound 40).

EXAMPLE 40

(±)-3-(4-Cyanobenzylthio)-4-(1-azabicyclo[2.2.2]octyl-3-oxy)-1,2,5-thiadiazole A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, 4-cyanobenzyl bromide (1.85 g, 0.094 mol) was added and the reaction stirred 22 h. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH- CHCl$_3$). The HCl salt (0.12 g) crystallized from CHCl$_3$-EtOAc-ether, m.p. 211–213° C. (Compound 41).

EXAMPLE 41

(±)-3-(4-Fluorobenzylthio)-4-(1-azabicyclo[2.2.2]
octyl-3-oxy)-1,2,5-thiadiazole A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, 4-fluorobenzyl chloride (1.37 g, 0.094 mol) was added and the reaction stirred 22 h. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH-CHCl$_3$). The HCl salt (0.89 g) crystallized from MeOH-EtOAc-ether, m.p. 236–237° C. (Compound 42).

EXAMPLE 42

(±)-3-(2-Phenylethylthio)-4-(1-azabicyclo[2.2.2]
octyl-3-oxy)-1,2,5-thiadiazole

A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, the reaction was cooled to −30° C. and treated with dropwise with 1-bromo-2-phenylethane (1.75 g, 0.095 mol) in DMF (22 mL). The cooling was removed after 1 h and the reaction stirred 22 h. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH-CHCl$_3$). The HCl salt (0.53 g) crystallized from MeOH-EtOAc-ether, m.p. 181–183° C. (Compound 43).

EXAMPLE 43

(±)-3-(2-Phenyloxyethylthio)-4-(1-azabicyclo[2.2.2]
octyl-3-oxy)-1,2,5-thiadiazole A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, the reaction was cooled to −50° C. and treated with dropwise with 1-bromo-2-phenyloxyethane (1.90 g, 0.0095 mol) in DMF (22 mL). The cooling was removed after 1 h and the reaction stirred 22 h. Another solution of bromo-2-phenyloxyethane (1.90 g, 0.0095 mol) in DMF (5 mL) was added in two portions with cooling to −30° C. After 2 h, the solvent was evaporated, the residue was acidified with 1N HCl, and the mixture extracted with ether. The aqueous was made basic and extracted with CHCl$_3$. The extracts were dried and the solvent evaporated to give a straw-colored liquid that was purified by radial chromatography (5% EtOH-0.5% NH$_4$OH-CHCl$_3$). The HCl salt (1.29 g) crystallized from MeOH-EtOAc-ether, m.p. 193–194° C. (Compound 44).

EXAMPLE 44

(±)-exo-3-Butyloxy-4-(N-methyl-8-azabicyclo[3.2.1]
octyl-1-oxy)-1,2,5-thiadiazole A solution of tropine (1.36 g, 0.0094 mol) in THF (25 mL) was treated dropwise with 1.6M n-butyllithium in hexane (5.9 mL, 0.00095 mol). To this solution was added 3-butyloxy-4-methanesulfonyl-1,2,5-thiadiazole (2.04 g, 0.0086 mol) in THF (25 mL) and the reaction heated to 40° C. for 19 h. The solution was treated with H$_2$O (40 mL), 5N HCl (5.5 mL), and ether (150 mL), the aqueous layer separated and made basic. The aqueous solution was extracted with ether, the extracts dried, and the solvent evaporated to give a clear oil. The oil was purified by radial chromatography (5% EtOH-0.5% NH$_4$OH-CHCl$_3$) and the HCl salt (1.49 g) crystallized from CHCl$_3$-EtOAc-ether, m.p. 168–169° C. (Compound 45).

EXAMPLE 45

(±) -exo-3-Butyloxy-4-(6-(N-methyl-8-azabicyclo
[3.2.1]octan-3-onoxy))-1,2,5-thiadiazole A suspension of NaH (0.11 g, 0.00275 mol) in THF (25 mL) was treated with (±)-exo-6-hydroxytropinone (1.36 g, 0.0094 mol) and the reaction heated to 50° C. for 1 h. To this solution was added 3-butyloxy-4-methanesulfonyl-1,2,5-thiadiazole (0.55 g, 0.0027 mol) and the reaction heated to reflux for 2 h. The solvent was evaporated, the residue suspended in ice-water, acidified, and the mixture extracted with ether. The aqueous layer was made basic, was extracted with ether, the extracts washed with brine, dried, and the solvent evaporated to give a clear oil. The oil was purified by radial chromatography (2.5% EtOH-0.25% NH$_4$OH-CHCl$_3$) and the HCl salt (0.325 g) crystallized from EtOAc, m.p. 178–179° C. (Compound 46).

EXAMPLE 46

(±)-exo-3-Chloro-4-(1-azabicyclo[3.2.1]octyl-6-
oxy)-1,2,5-thiadiazole and (±)-endo-3-Chloro-4-(1-
azabicyclo[3.2.1]octyl-6-oxy)-1,2,5-thiadiazole A solution of the endo/exo mixture of 1-azabicyclo[3.2.1] octan-6-ol (13 g, 0.102 mol, ref. Sternbach, L. H.; Kaiser, S. J. Amer. Chem. Soc. 1952, 74, 2215–2218), triethylamine (0.3 mL), and CHCl$_3$ (100 mL) was cooled to 3° C. and cyanogen (7.7 g, 0.148 mol) bubbled into the solution. After 1 h, the cooling was removed, the reaction stirred another 3 h, and the solvent evaporated. The residue was dissolved in DMF (30 mL) and added dropwise to a solution of S$_2$Cl$_2$ (47.3 g, 0.35 mol) in DMF (30 mL) that was cooled in an ice-water bath. Cooling was removed, the reaction stirred overnight, and, after further cooling, the excess S$_2$Cl$_2$ carefully destroyed with H$_2$O. The mixture was diluted with H$_2$O (200 mL), the aqueous solution decanted, and the sulfur residue triturated with H$_2$O. The combined aqueous solutions were evaporated to a small volume (150 mL) and extracted with hexane. The aqueous solution was cooled, made basic with 50% NaOH, and extracted with CHCl$_3$. The extracts were dried, the solvent thoroughly evaporated, the residue suspended in ether and filtered. Evaporation of the solvent gave a brown liquid (12.76 g), a 0.8 g sample of which was purified by radial chromatography (10% EtOH-1% NH$_4$OH-CHCl$_3$). The exo isomer eluted first and was converted to an HCl salt (0.1 g) that crystallized from acetone, m.p. 226° C., dec. (compound 47). Further elution provided the endo isomer that crystallized as an HCl salt (0.2 g) from 2-propanol, m.p. 199.5–201° C. (Compound 48).

EXAMPLE 47

(±)-endo-3-(4-Cyanobenzylthio)-4-(1-azabicyclo
[3.2.1]octyl-6-oxy)-1,2,5-thiadiazole A solution of the crude mixture of (compound 47) and (compound 48) (2.3 g, 0.0094 mol) in DMF (34 mL) was treated portionwise with freshly ground flaked Na₂S-9H₂O (3.36 g, 0.014 mol). After 2 h, the reaction was cooled to −30° C. and treated with dropwise with 4-cyanobenzyl bromide (3.7 g, 0.0189 mol) in DMF (34 mL). The cooling was removed and after 1.5 h, the reaction was treated with 5N NaOH (4 mL). The solvents were evaporated, the residue dissolved in a mixture of CHCl₃ and H₂O, the CHCl₃ extract separated, and washed with H₂O. The organic extracts were dried, the solvent evaporated, and the residue purified by radial chromatography (5% EtOH-0.5% NH₄OH-EtOAc) to give the endo isomer. The HCl salt (0.31 g) crystallized from MeOH-EtOAc-ether, m.p. 250–251° C. (Compound 49).

EXAMPLE 48

3-Butyloxy-4-(3-azetidinyloxy)-1,2,5-thiadiazole

A suspension of NaH (0.24 g, 0.006 mol) in THF (30 mL) was treated with 1-t-butylcarbamoyl-3-hydroxyazetidine (1.1 g, 0.006 mol), the reaction stirred 1 h, followed by addition of 3-butyloxy-4-methanesulfonyl-1,2,5-thiadiazole (1.0 g, 0.0042 mol) in THF (5 mL). The reaction was heated to reflux for 4 h, the solvent evaporated, the residue treated with ice-water, and the mixture extracted with EtOAc. The extracts were dried and treated with a slow stream of HCl for 3 min. After 0.5 h, the solvent was evaporated, the residue treated with ice-water, and the solution extracted with ether. The aqueous phase was made basic, extracted with EtOAc, the extracts washed with brine, dried, and the solvent evaporated to give a clear oil. The HCl salt (0.77 g) crystallized from 2-propanol, m.p. 167–168.5° C. (Compound 50).

EXAMPLE 49

3-Butylthio-4-(3-azetidinyloxy)-1,2,5-thiadiazole

A suspension of NaH (0.24 g, 0.006 mol) in THF (30 mL) was treated with 1-t-butylcarbamoyl-3-hydroxyazetidine (1.6 g, 0.0092 mol), and the reaction stirred 1 h. After cooling to 8° C., 3-chloro-4-ethylsulfonyl-1,2,5-thiadiazole (1.96 g, 0.0092 mol) in THF (5 mL) was added, the reaction stirred 30 min, cooling removed for 30 min, and the reaction heated to 35° C. for 45 min. Heating was removed, the reaction stirred overnight, and the solvent evaporated. The residue was suspended in cold water, the mixture extracted with EtOAc, the extracts washed with brine, dried, and the solvent evaporated to give a tan liquid, (2.98 g). A DMF (30 mL) solution of the liquid was treated with freshly ground flaked Na₂S-9H₂O (3.3 g, 0.0138 mol). After 1 h, 1-iodobutane (2.1 mL) was added, the reaction stirred 2 h, diluted with cold water, and extracted with ether. The ether was dried, the solvent evaporated, the residue dissolved in EtOAc, and the solution treated with a stream of dry HCl for 5 min. After 1 h, the reaction was treated with icewater and the organic solvent evaporated. The aqueous solution was extracted with ether, made basic, and extracted with EtOAc. The EtOAc extracts were dried and the solvent evaporated to give a tan liquid that was purified by radial chromatography (10% EtOH-1% NH₄OH-CHCl₃). The HCl salt (0.41 g) crystallized from EtOAc, m.p. 138–139° C. (Compound 51).

EXAMPLE 50

(±)-trans-3-Butyloxy-4-(2-dimethylaminocyclopentyloxy)-1,2,5-thiadiazole

A suspension of NaH (0.25 g, 0.006 mol) in THF (30 mL) was treated with (±)-trans-dimethylaminocyclopentanol (0.8 g, 0.006 mol), the reaction heated to reflux 1 h, followed by addition of 3-butyloxy-4-methanesulfonyl-1,2,5-thiadiazole (1.0 g, 0.0042 mol), and the heating continued overnight. The solvent was evaporated, the residue suspended in cold water, and the mixture acidified. The solution was extracted with ether, made basic, and extracted with EtOAc. The EtOAc extracts were washed with brine, dried, the solvent evaporated, and the residue purified by radial chromatography (10% EtOH-1% NH₄OH-CHCl₃). The HCl salt (0.98 g) crystallized from EtOAc, m.p. 148–149° C. (Compound 52).

EXAMPLE 51

(±)-3-Butylthio-4-(3-pyrrolidinyloxy)-1,2,5-thiadiazole

A suspension of NaH (0.22 g, 0.009 mol) in THF (30 mL) was treated with (±)-1-t-butylcarbamoyl-3-hydroxypyrrolidine (1.73 g, 0.0092 mol), and the reaction heated to reflux for 35 min. After cooling to 10° C., 3-chloro-4-ethylsulfonyl-1,2,5-thiadiazole (1.96 g, 0.0092 mol) in THF (5 mL) was added, cooling was removed, and the reaction heated to 35° C. for 16 h. The reaction was diluted with H₂O, ether added, and the ether extract separated. The ether extract was washed with H₂O, dried, and the solvent evaporated to give a tan liquid, (3.05 g). A DMF (42 mL) solution of the liquid was treated with freshly ground flaked Na₂S-9H₂O (3.3 g, 0.0138 mol). After 1 h, 1-iodobutane (3.42 g, 0.0186 mol) was added, and the reaction stirred at 40° C. for 16 h. The solvent was evaporated, the residue diluted with cold water, and the mixture extracted with ether. The ether was dried, the solvent evaporated, the residue dissolved in ether, and the solution treated with a stream of dry HCl for 5 min. After 66 h, the reaction was treated with ice-water and the organic solvent evaporated. The aqueous solution was extracted with ether, made basic, and extracted with ether. The ether extracts were dried and the solvent evaporated to give a tan liquid that was purified by radial chromatography (5% EtOH-0.5% NH₄OH-CHCl₃). The HCl salt (0.67 g) crystallized from EtOAc, m.p. 99–100.5° C. (Compound 53).

EXAMPLE 52

1-Chloro-2-(2-thio-5-trifluoromethylthienyl)ethane

A solution of 2-trifluoromethylthiophene (1.2 g, 0.0105 mol, *J. Fluorine Chem.* 1990, 46, 445–459) in THF (10 mL) was cooled to −40° C. as 1.6M n-butyllithium in hexane (6.5 mL, 0.0103 mol) was added dropwise. After 2 h, the reaction was cooled to −78° C. and S (0.32 g, 0.01 mol) was added and the reaction stirred 2 h. Cooling was removed and when temperature reached 0° C., the reaction was quenched with H₂O and dilute NaOH. The mixture was extracted with ether, the aqueous phase acidified, and the mixture extracted with ether. The final ether extracts were dried and the solvent evaporated to give 2 g of material. This was added to a mixture of KOH (0.6 g, 0.011 mol), N(butyl)₄HSO₄ (0.3 g, 0.001 mol), and 1-bromo-2-chloroethane (1.4 g, 0.01 mol) in THF (20 mL) and the reaction stirred at ambient overnight. The mixture was poured into H₂O, extracted with CH₂Cl₂, the extracts dried, and the solvent evaporated. The residue was purified by flash chromatography (5% EtOAc-hexane) to give a liquid (0.42 g). (Compound 54).

EXAMPLE 53

(±)-3-(2-(2-Thio-5-trifluoromethylthienyl)ethylthio)-4-(1-azabicyclo[2.2.2]octyl-3-oxy)-1,2,5-thiadiazole A solution of the crude (compound 12) (0.37 g, 0.0015 mol) in DMF (8 mL) was treated portionwise with freshly ground flaked Na$_2$S-9H$_2$O (0.41 g, 0.0017 mol). After 1 h, 1-chloro-2-(2-thio-5-trifluoromethylthienyl) ethane (0.42 g, 0.0017 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by radial chromatography (10% EtOH-1% NH$_4$OH-CHCl$_3$) to give a liquid. The oxalate salt (0.107 g) crystallized from 2-propanol, m.p. 65–69° C. (Compound 55).

EXAMPLE 54

2-(5-(2-Thienyl)thiophene)thiol

A solution of 2-(2-thienyl)thiophene (10 g, 0.0602 mol) in THF (50 mL) was cooled to −40° C. as 1.6M n-butyllithium in hexane (37.2 mL, 0.0595 mol) was added dropwise. After 2 h, the reaction was cooled to −78° C. and S (1.8 g, 0.0575 mol) was added and the reaction stirred 2 h. Cooling was removed and when temperature reached 0° C., the reaction was quenched with H$_2$O and dilute NaOH. The mixture was extracted with ether, the aqueous phase acidified, and the mixture extracted with ether. The final ether extracts were dried and the solvent evaporated to give 9.9 g of material. (Compound 56).

EXAMPLE 55

(±)-3-(2-(5-(2-Thienyl)thienyl)thio)-4-(1-azabicyclo[2.2.2]octyl-3-oxy)-1,2,5-thiadiazole A mixture of 2-(5-(2-thienyl)thiophene)thiol (1.2 g, 0.0061 mol), potassium t-butoxide (0.5 g, 0.0045 mol), and a trace of 18-Crown-6 in THF (90 mL) was stirred for 1.5 h. To the solution was added (compound 12) (1.0 g, 0.0041 mol) and the reaction heated to reflux overnight. The reaction was poured into H$_2$O, extracted with ether, the extracts dried, and the solvent evaporated. The residue was purified by flash chromatography (5% EtOH-0.5% NH$_4$OH-CHCl$_3$) and the oxalate salt (0.41 g) crystallized from acetone, m.p. 215° C., dec. (Compound 57).

EXAMPLE 56

1-Chloro-2-(2-(5-(2-thienyl)thienyl)thio)ethane

Crude 2-(5-(2-thienyl)thiophene)thiol (3 g, 0.0152 mol) was added to a mixture of KOH (0.93 g, 0.0166 mol), N(butyl)$_4$HSO$_4$ (0.51 g, 0.0015 mol), and 1-bromo-2-chloroethane (2.2 g, 0.0152 mol) in THF (100 mL) and the reaction stirred at ambient overnight. The mixture was poured into H$_2$O, extracted with CH$_2$Cl$_2$, the extracts dried, and the solvent evaporated to give the desired product (3.5 g). (Compound 58).

EXAMPLE 57

(±)-3-(2-(2-(5-(2-Thienyl)thienyl)thio)ethylthio)-4-(1-azabicyclo[2.2.2]octyl-3-oxy)-1,2,5-thiadiazole A solution of the crude (compound 12) (0.5 g, 0.002 mol) in DMF (10 mL) was treated portionwise with freshly ground flaked Na$_2$S-9H$_2$O (0.55 g, 0.0023 mol). After 1 h, 1-chloro-2-(2-(5-(2-thienyl)thienyl)thio)ethane (0.6 g, 0.0023 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by flash chromatography (5% EtOH-0.5% NH$_4$OH-CHCl$_3$) to give a liquid. The oxalate salt (0.43 g) crystallized from acetone, m.p. 102–105° C. (Compound 59).

EXAMPLE 58

(±)-3-(2-Thienyl)thio)-4-(1-azabicyclo[2.2.2]octyl-3-oxy)-1,2,5-thiadiazole

A mixture of 2-thiophenethiol (0.42 g, 0.0036 mol) and K$_2$CO$_3$ (0.59 g, 0.0043 mol), in DMF (20 mL) was heated at 60° C. for 3 h. To the solution was added (compound 12) (0.89 g, 0.0036 mol) and the reaction heated overnight. The reaction was poured into 1N HCl (50 mL), extracted with ether, the aqueous phase made basic, and the mixture extracted with EtOAc. The EtOAc extracts were dried, the solvent evaporated, and the residue purified by flash chromatography (5% EtOH-0.5% NH$_4$OH-CHCl$_3$). The oxalate salt (0.095 g) crystallized from acetone, m.p. 133–136° C. (Compound 60).

EXAMPLE 59

(±)-3-(3-N-(2-Thiazolidonyl)propylthio)-4-(1-azabicyclo[2.2.2]octyl-3-oxy)1,2,5-thiadiazole A solution of the crude (compound 12) (0.5 g, 0.002 mol) in DMF (10 mL) was treated portionwise with freshly ground flaked Na$_2$S-9H$_2$O (0.55 g, 0.0023 mol). After 1 h, 1-chloro-3-N-(2-thiazolidone) propane (0.41 g, 0.0023 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by radial chromatography (10% EtOH-1% NH$_4$OH-CHCl$_3$) to give a liquid. The oxalate salt (0.148 g) crystallized from acetone-ether, m.p. 70–75° C. (Compound 61).

EXAMPLE 60

(±)exo-Methyl-7-hydroxy-2-azabicyclo[2.2.2]oct-5-ene-2-carboxylate

A solution of 2.1 g (8.4 mmol) methyl 7-acetoxy-7-cyano-2-azabicyclo[2.2.2]oct-5-ene-2-carboxylate (*J. Org. Chem.* 1989, 54, 2893) in 25 mL ethanol and 5 mL H$_2$O was cooled in an ice bath. To this mixture was added 2.4 g (42 mmol) KOH followed by 0.65 g (17 mmol) NaBH$_4$. After 15 min. the ice bath was removed and the reaction was stirred for 16 h. The reaction was quenched by addition of 25 mL H$_2$O and then concentrated under vacuum. To the residue was added 25 mL H$_2$O and the mixture was extracted three times with 50 mL portions of EtOAc. The combined extracts were dried over NaCl/Na$_2$SO$_4$ and evaporated under vacuum. The residue was chromatographed (25% EtOAc/hexane) on silica gel to give 1.47 g of exo methyl 7-hydroxy-2-azabicyclo[2.2.2]oct-5-ene-2-carboxylate and 135 mg of endo methyl 7-hydroxy-2-azabicyclo[2.2.2]oct-5-ene-2-carboxylate. (Compound 62).

EXAMPLE 61

(±)exo-Methyl-6-hydroxy-2-azabicyclo[2.2.2]octane-2-carboxylate

A solution of 1.47 g (8 mmol) exo methyl 7-hydroxy-2-azabicyclo[2.2.2]oct-5-ene-2-carboxylate and 0.15 g 5% Pd/C in 50 mL methanol was hydrogenated at 50 psi on a Parr shaker for 5 h at room temperature. Removal of the catalyst by filtration followed by evaporation under vacuum afforded 1.43 g. (Compound 63).

EXAMPLE 62

(±)3-Butylthio-4-(exo-2-methoxycarbonyl-2-azabicyclo[2.2.2]oct-6-yloxy)-1,2,5-thiadiazole To a solution of 1.3 g (7.1 mmol) exo methyl 6-hydroxy-2-azabicyclo[2.2.2]octane-2-carboxylate and 0.80 g (7.1 mmol) potassium t-butoxide in 20 mL of THF was added 1.5 9 (7.1 mmol) 3-chloro-4-butylthio-1,2,5-thiadiazole. After stirring the mixture at room temperature for 20 h, 50 mL of brine was added and the solution was extracted five times with 50 mL portions of EtOAc. The combined extracts were dried over NaCl/$Na_2SO_4$ and evaporated under vacuum. Chromatography over silica gel (25% EtOAc/hexane) afforded 1.42 g. (Compound 64).

EXAMPLE 63

(±)3-Butylthio-4-(exo-2-azabicyclo[2.2.1]oct-6-yloxy)-1,2,5-thiadiazole

Trimethylsilyliodide 0.70 mL (4.9 mmol) was added to a solution of 3-butylthio-4-(exo-2-methoxycarbonyl-2-azabicyclo[2.2.2]oct-6-yloxy)-1,2,5-thiadiazole in 10 mL of $CH_2Cl_2$. After stirring for 5 h at room temperature, the solution was evaporated under vacuum. 10 mL of saturated $NaHCO_3$ was added and the solution was extracted three times with 20 mL portions of EtOAc. The combined extracts were dried over NaCl/$Na_2SO_4$ and evaporated under vacuum. The residue was chromatographed over silica gel (10% EtOH, 1% $NH_4OH$-$CHCl_3$) and the resulting oil converted to its oxalate salt. Recrystallization from EtOH/EtOAc afforded 789 mg (mp. 148–150° C.). (Compound 65).

EXAMPLE 64

3-Amino-4-butylthio-1,2,5-thiadiazole

A 1.04 g sample of 3-chloro-4-butylthio-1,2,5-thiadiazole was dissolved in 20 mL of THF and added to a 50 mL reaction vessel. The mixture was cooled to 0° C. A 10 mL sample of sodium bis(trimethylsilyl)amide in THF (1.0M) was added dropwise to the reaction vessel. The mixture was stirred at 0° C. The reaction was quenched using 50 mL water upon desired completion of reaction. The pH of the mixture was adjusted to 2.0 using HCl. The mixture was stirred for 15 min. and then adjusted to pH=11 using NaOH. The mixture was extracted using ether. The organic layers were combined, dried, and filtered. The filtrate was concentrated to dryness. The resulting product was purified using column chromatography. Yield: 1.07 g (65%). The N,N-bis (trimethylsilyl)-3-amino-4-butylthio-1,2,5-thiadiazole was suspended in 3N HCl and heated to about 50° C. The mixture was stirred for 3 h. The pH was adjusted to 11 using NaOH. The mixture was extracted using t-butylmethyl ester. The organics were combined, dried, filtered and concentrated to dryness. Yield: 0.43 g (45%). (Compound 66). The process substantially as described was repeated to yield 82% of the desired 3-amino-4-butylthio-1,2,5-thiadiazole.

EXAMPLE 65

3-Bromo-4-butylthio-1,2,5-thiadiazole

A 0.42 g sample of cupric bromide, 0.28 isoamyl nitrite and 6 mL acetonitrile were added to a 25 mL reaction vessel. The mixture was warmed to 65° C. The acetonitrile mixture was added to a 4 mL acetonitrile solution containing 0.30 g 4-amino-3-butylthio-1,2,5-thiadiazole. The mixture was stirred for 30 min. at 65°. The mixture was cooled to room temperature and quenched with 50 mL of 1N HCl. The organic layers were combined, dried, filtered and concentrated to dryness. Yield: 0.38 g (94%). The resulting material was purified using column chromatography to yield 0.30 g (73%) of material. (Compound 67).

The process substantially as described above was completed using copper(I) iodide (0.61 9) to provide 3-iodo-4-butylthio-1,2,5-thiadiazole. Yield: 0.23 g (48%). (Compound 68).

EXAMPLE 66

(±)3-(2,2,3,3,4,4,4-heDtafluorobutyloxy)-4-[-3-(1-azabicyclo[2.2.2]octyloxy)]-1,2,5-thiadiazole A solution of potassium t-butoxide (1.6 g, 0.0143 mol) in THF (12 mL) was treated with 2,2,3,3,4,4,4-heptafluorobutanol (2 mL, 0.016 mol). After 5 min, Compound 12 (0.75 g, 0.003 mol) was added, the reaction stirred 2 h followed by heating to reflux for 1.5 h. After stirring at ambient temperature overnight and heating to reflux for another 1.5 h, the solvent was evaporated, the residue suspended in $H_2O$, and the mixture extracted with EtOAc. The extracts were dried, the solvent evaporated, and the residue purified by radial chromatography (20% EtOH-2% $NH_4OH$-$CHCl_3$) to give an oil. The hydrochloride salt crystallized from EtOAc with a half mole of $H_2O$ as a flocculent white solid (0.43 g), m.p. 168.5–169.5° C. (Compound 69).

EXAMPLE 67

(±)3-(1-Butylthio)-4-[endo--6-(1-azabicyclo[3.2.1] octyloxy)]-1,2,5-thiadiazole

A solution of potassium t-butoxide (0.62 g, 0.0055 mol) in THF (12 mL) was treated with endo-1-azabicyclo[3.2.1] octan-6-ol (0.64 g, 0.005 mol). After 5 min, 3-chloro-4-(1-butylthio)-1,2,5-thiadiazole (1.2 g, 0.0057 mol) was added. After stirring overnight, the solvent was evaporated, the residue diluted with $H_2O$, acidified, and extracted with ether. The aqueous phase was made basic and extracted with EtOAc, the extracts dried, washed with brine, dried, and the solvent evaporated. The residue was purified by radial chromatography (20% EtOH-2% $NH_4OH$-$CHCl_3$). The HCl salt crystallized from EtOAc to give a white solid (0.68 g), m.p. 201–202 ° C. dec. (Compound 70).

EXAMPLE 68

(±)3-(3-Phenylpropylthio)-4-[endo--6-(1-azabicyclo [3.2.1]octyloxy)]-1,2,5-thiadiazole A solution of Compound 48 (0.9 g, 0.0037 mol) in DMF (25 mL) was treated portionwise with freshly ground flaked $Na_2S$-$9H_2O$ (0.97 g, 0.004 mol). After 2 h, the reaction was treated with dropwise with 1-bromo-3-phenylpropane (1.11 g, 0.0059 mol), the reaction stirred 3.25 h, followed by dropwise addition of additional 1-bromo-3-phenylpropane (1.11 g, 0.0059 mol) in DMF (5 mL). After stirring overnight, the solvents were evaporated, the residue suspended in $H_2O$, acidified, and the mixture extracted with ether. The aqueous phase was made basic, extracted with $CHCl_3$, the extracts dried, and the solvent evaporated. The residue purified by radial chromatography (MeOH:EtOAc:NH$_4$OH/15:30:1) to give an oil. The HCl salt (0.41 g) crystallized from CHCl$_3$-EtOAc-ether, m.p. 178–179 ° C. (Compound 72).

EXAMPLE 69

(±)3-[3-(4-Fluorophenyl)propylthio]-4-[-3-(1-azabicyclo[2.2.2]octyloxy)]-1,2,5-thiadiazole A solution of the crude Compound 12 (1.15 g, 0.0047 mol) in DMF (20 mL) was treated portionwise with freshly ground flaked Na$_2$S-9H$_2$O (1.68 g, 0.007 mol). After 1 h, 1-chloro-3-(4-fluorophenyl)propane (1.63 g, 0.0095 mol) in DMF (2 mL) was added dropwise and the reaction stirred 2.5 days. The reaction was then treated with additional 1-chloro-3-(4-fluorophenyl)propane (0.815 g, 0.0047 mol) and warmed at 35° C. for 6 h. The solvent was evaporated, the residue was acidified with 1N HCl, and the mixture extracted with ether. The aqueous was made basic and extracted with ether. The extracts were dried, the solvent evaporated, and the residue purified by radial chromatography (MeOH:EtOAc:NH$_4$OH/15:30:1). The HCl salt (0.19 g) crystallized from CHCl$_3$-EtOAc-ether, m.p. 189–191° C. (Compound 73),

EXAMPLE 70

(±)3-{3-[4-(Trifluoromethyl)phenyl]propylthio}-4-[-3-(1-azabicyclo[2.2.2]octyloxy)]-1,2,5-thiadiazole A solution of the Compound 12 (1.15 g, 0.0047 mol) in DMF (20 mL) was treated portionwise with freshly ground flaked Na$_2$S-9H$_2$O (1.68 g, 0.007 mol). After 2 h, the reaction was cooled to −35° C., treated dropwise with 1-bromo-3-[4-(trifluoromethyl)phenyl]propane (2.53 g, 0.0095 mol) in DMF (30 mL), and the reaction stirred 2 h. Cooling was removed, reaction stirred 3.5 h, and again cooled to −35° C. The reaction was then treated with additional 1-bromo-3-[4-(trifluoromethyl)phenyl]propane (1.75 g, 0.0043 mol) in DMF (5 mL), cooling removed, and reaction stirred over night. Additional 1-bromo-3-[4-(trifluoromethyl)phenyl]propane (0.75 g, 0.0028 mol) in DMF (5 mL) was added and stirring continued for 1.5 h. The solvent was evaporated, the residue suspended in H$_2$O, and the mixture extracted with ether. The extracts were dried, the solvent evaporated, and the residue purified by radial chromatography (MeOH:EtOAc:NH$_4$OH/15:30:1). The HCl salt (0.32 g) crystallized from CHCl$_3$-EtOAc-ether, m.p. 182–184° C. (Compound 74),

EXAMPLE 71

3-(1-Butylamino)-4-[(+,−)-3-(1-azabicyclo[2.2.2]octyloxy)]-1,2,5-thiadiazole

A mixture of Compound 12 (1.15 g, 0.0047 mol) and 1-butylamine (20 mL) was heated to reflux for 22 h. The solvent was evaporated, residue suspended in H$_2$O, the mixture acidified, and extracted with ether. The aqueous phase was made basic, extracted with EtOAc, extracts dried, and solvent evaporated. Purification by radial chromatography (MeOH:EtOAc:NH$_4$OH/15:30:1) and conversion to a HCl salt gave a solid partial hydrate (0.046 g), m.p. 193–195° C. (Compound 75),

EXAMPLE 72

Cyanogen Butyloxyimide

A solution of 1-butanol (92 mL, 1 mol) and triethylamine (3 mL) was cooled to −8° C. and cyanogen (58 g, 1.12 mol) was slowly bubbled through the solution while maintaining the temperature below 2° C. The reaction mixture was then distilled at 7 mm Hg to give a clear liquid (119.4 g) b.p. 43–49° C. (Compound 76).

EXAMPLE 73

3-Chloro-4-butyloxy-1,2,5-thiadiazole

A solution of DMF (400 mL) and sulfur monochloride (230 mL) was cooled to 5° C. and Compound 76 (119.4 g, 0.95 mol) was added dropwise such that the temperature did not exceed 10° C. Cooling was removed and the reaction was stirred over night. The reaction was cooled in an ice-water bath and the excess sulfur monochloride destroyed by dropwise addition of H$_2$O such that the temperature did not exceed 30° C. The liquid was decanted from the semi-solid sulfur precipitant and the sulfur residue triturated with hexane. The aqueous fraction was extracted with hexane (3×) and the combined extracts and triturants were washed with H$_2$O, aqueous NaHCO$_3$, brine, dried, and the solvent evaporated. The yellow liquid residue was distilled at 14 mm Hg to give a clear liquid (153 g), b.p. 120–125° C. (Compound 77).

EXAMPLE 74

3-Methylthio-4-butyloxy-1,2,5-thiadiazole

A solution of Compound 77 (6 g, 0.031 mol) in DMF (75 mL) was rapidly stirred as ground flaked Na$_2$S-9H$_2$O (8 g, 0.034 mol) was added. After 1 h, CH$_3$I (3 mL, 0.048 mol) was added and the reaction stirred 30 min. Ice-water (150 mL) was added to the reaction and the mixture extracted with hexane (3×). The extracts were washed with H$_2$O (2×), dried and the solvent evaporated to give a clear liquid (6.04 g). (Compound 78).

EXAMPLE 75

3-Methylsulfonyl-4-butyloxy-1,2,5-thiadiazole

To a solution of Oxone (18.4 g, 0.03 mol) in H$_2$O (100 mL) was added dropwise Compound 78 (3 g, 0.0147 mol) in THF (45 mL). After stirring overnight, the organics were evaporated and the residue extracted with ether (3×). The extracts were washed with H$_2$O (2×), dried, and the solvent evaporated. The residue was purified by radial chromatography eluting with 50% EtOAc-hexane to give a clear colorless liquid (2.93 g) that solidified on standing, m.p. 39–40° C. (Compound 79),

EXAMPLE 76

3-Methylthio-4-hexyloxy-1,2,5-thiadiazole

A solution of 3-chloro-4-hexyloxy-1,2,5-thiadiazole (CA 60, 2796e, 1964) ( 1.1 g, 0.005 mol) in DMF (30 mL) was rapidly stirred as ground flaked Na$_2$S-9H$_2$O (1.5 g, 0.00625 mol) was added. After stirring overnight, CH$_3$I (2 mL ) was added and the reaction stirred 30 min. Ice-water (150 mL) was added to the reaction and the mixture extracted with ether (2×). The extracts were washed with H$_2$O (2×), dried and the solvent evaporated to give a clear liquid (1.025 g). (Compound 80),

EXAMPLE 77

3-Methylsulfonyl-4-hexyloxy-1,2,5-thiadiazole

To a solution of Oxone (18.4 g, 0.03 mol) in H$_2$O (100 mL) was added dropwise Compound 80 (3.4 g, 0.0147 mol)

in THF (50 mL). After stirring for three days, the organics were evaporated and the residue extracted with ether (3×). The extracts were washed with $H_2O$ (2×), dried, and the solvent evaporated. The residue was purified by radial chromatography eluting with 50% EtOAc-hexane to give a clear colorless liquid (3.58 g). (Compound 81).

EXAMPLE 78

Cyanogen Propyloxyimide

A solution of 1-propanol (40 mL, 0.536 mol) and triethylamine (1.5 mL) was cooled to −8° C. and cyanogen (36 g, 0.69 mol) was slowly bubbled through the solution while maintaining the temperature below 2° C. The reaction mixture was then distilled at 20 mm Hg to give a clear liquid ( 59 g) b.p. 63–64° C. (Compound 82),

EXAMPLE 79

3-Chloro-4-propyloxy-1,2,5-thiadiazole

A solution of DMF (180 mL) and sulfur monochloride (120 mL, 1.5 mol) was cooled to 5° C. and Compound 82 (59 g, 0.527 mol) was added dropwise such that the temperature did not exceed 10° C. Cooling was removed and the reaction was stirred over night. The reaction was cooled in an ice-water bath and the excess sulfur monochloride destroyed by dropwise addition of $H_2O$ such that the temperature did not exceed 30° C. The liquid was decanted from the semi-solid sulfur precipitant and the sulfur residue triturated with hexane. The aqueous fraction was extracted with hexane (3×) and the combined extracts and triturants were washed with $H_2O$, aqueous $NaHCO_3$, brine, dried, and the solvent evaporated. The yellow liquid residue was distilled at 15 mm Hg to give a clear liquid (79.9 g), b.p. 103–106° C. (Compound 83),

EXAMPLE 80

3-Methylthio-4-propyloxy-1,2,5-thiadiazole

A solution of Compound 83 (11.1 g, 0.062 mol) in DMF (150 mL) was rapidly stirred as ground flaked $Na_2S$-9 $H_2O$ (16.4 g, 0.068 mol) was added. After 1 h, $CH_3I$ (6 mL, 0.096 mol) was added and the reaction stirred 30 min. Ice-water (300 mL) was added to the reaction and the mixture extracted with hexane (3×). The extracts were washed with $H_2O$ (2×), dried and the solvent evaporated to give a clear liquid (11.02 g). (Compound 84),

EXAMPLE 81

(±)-3-(4,4,4-Trifluorobutyloxy)-4-(1-azabicyclo [2.2.2]octyl-3-oxy)-1,2,5-thiadiazole A solution of 4,4,4-trifluorobutanol (0.75 g) in THF (20 mL) was cooled to 0° C. and potassium t-butoxide (0.65 g) was added. After 5 min, a solution of Compound 102 (0.6 g) in THF (5 mL) was added and the reaction stirred one hour. The reaction was quenched with 5N HCl (1.5 mL) and the solvent evaporated. The residue was suspended in water and extracted with ether. The aqueous phase was made basic and extracted with EtOAc. The extracts were dried, the solvent evaporated, and the residue purified by radial chromatography eluting with 20%-EtOH-1%-$NH_4OH$-$CHCl_3$ to give a clear oil. The HCl salt was recrystallized from EtOAc-ether to give a white solid, m.p. 122–124° C. (0.43 g). (Compound 104).

EXAMPLE 82

(±) -endo-3-Propylsulfonyl-4-(1-azabicyclo[3.2.1] octyl-6-oxy)-1,2,5-thiadiazole A solution of (±)-endo-3-propylthio-4-(1-azabicyclo [3.2.1]octyl-6-oxy)-1,2,5-thiadiazole (5.7 g) in 1N HCl (24 mL) was cooled in ice-water and Oxone (36.8 g) in $H_2O$ (75 mL) was added dropwise over 5 min. Cooling was removed and after 5 h, excess oxidant was destroyed with $NaHSO_3$. The reaction was poured into ice and the pH adjusted to 12. The mixture was extracted with EtOAc, the extracts washed with water, the solvent dried, and the solvent evaporated to give analytically pure (i)-endo-3-propylsulfonyl-4-(1-azabicyclo[3.2.1]octyl-6-oxy)-1,2,5-thiadiazole as an oil (4.6 g). (Compound 166).

EXAMPLE 83

(±)-3-Butyloxy-4-(1-azabicyclo[2.2.2]octyl-3-oxy) -1,2,5-oxadiazole

A suspension of 3,4-diphenylsulfonyl-1,2,5-oxadiazole oxide (4.6 g, 0.126 mol, Ref. *J. Chem. Soc.* 1964, 904.) in 1-butanol (400 mL) was heated to 55–60° C. as a solution of sodium 1-butyloxide (0.3 g Na, 40 mL 1-butanol) was added dropwise. After 1 h, the solvent was evaporated, residue was treated with $H_2O$, and the mixture extracted with ether (3×). The extracts were washed with $H_2O$, dried, and the solvent evaporated to give a white solid (3.15 g). The solid was heated to reflux overnight in $P(OCH_3)_3$ (30 mL) then poured into ice-$H_2O$ containing HCl (6 mL, 5N). The mixture was extracted with ether, the extracts washed with brine, dried, and the solvent evaporated to give a yellow liquid. Radial chromatography (15% EtOAc/hexane) gave a clear liquid (1.85 g). The liquid was dissolved in THF (30 mL) and added dropwise to a mixture prepared from 1-azabicyclo [2.2.2]octan-3-ol(1.85 g 0.014 mol), THF (20 mL), and 1.6M n-butyl lithium in hexane (8.4 mL, 0.013 mol). The reaction was then warmed to 52° C. for 5 h. The cooled reaction was acidified with dilute HCl and diluted wit ether. the aqueous fraction was washed with ether, made basic, and extracted with ether. The extracts were dried and evaporated to give a clear liquid. The HCl salt (1.4 g) crystallized from $CHCl_3$-EtOAc-ether, m.p. 186–188° C. (Compound 1).

EXAMPLE 1'

(±)-endo-2-(4-Methyl-3-pentenylthio)-3-(1-azabicyclo[3.2.1]octyl-6-oxy)pyrazine

Obtained from Compound 19 and 1-bromo-4-methyl-3-pentene in 8% yield as a foam. (Compound 43).

EXAMPLE 2'

(+/−)-3-Chloro-2-(1-azabicyclo[2.2.2]octyl-3-oxy) pyrazine

A solution of 1-azabicyclo[2.2.2]octan-3-ol (5 g, 0.039 mol) in THF (400 mL) was treated with 1.6M n-butyllithium in hexane (25 mL, 0.04 mol). After 1 h, the solution was cooled in an ice-water bath and 2,3-dichloropyrazine (6.6 g, 0.044 mol) in THF (30 mol) was added in one portion. Cooling was removed and after 30 min., the reaction was heated to reflux for 2.5 h. The solvent was evaporated, the residue acidified with 1N HCl, and the mixture extracted with ether. The aqueous fraction was made basic and extracted with ether. The extracts were washed with water, dried, and the solvent evaporated to give a tacky solid. Recrystallization from ether gave a yellow solid (1.74 g), m.p. 112.5–114° C. (Compound 2).

EXAMPLE 3'

(+/−)-3-Butyloxy-2-(1-azabicyclo[2.2.2]octyl-3-oxy) pyrazine

A solution of sodium butyloxide (0.25 g Na, 0.0109 mol, 1-butanol, 30 mL) was added to (compound 2) (0.48 g, 0.002 mol), the reaction stirred overnight, then heated to 80° C. for 4 h. The solution was acidified and the solvent evaporated. The residue was suspended in $H_2O$, extracted with ether, and the aqueous solution made basic. The aqueous fraction was extracted with EtOAc, the extracts washed with $H_2O$, dried, and the solvent evaporated to give a yellow oil. The HCl salt (0.32 g) crystallized from EtOAc as a white powder, m.p. 150–151° C. (Compound 3).

EXAMPLE 4'

(+/−)-3-Propyloxy-2-(1-azabicyclo[2.2.2]octyl-3-oxy)pyrazine

To a solution of lithium 1-propyloxide (7 mL 1.6M n-butyllithium, 0.011 mol, 1-propanol, 30 mL) was added (compound 2) (0.63 g, 0.0026 mol) and the reaction heated to reflux for 6 h. The solvent was evaporated, the residue suspended in $H_2O$, and the mixture extracted with EtOAc. The extracts were washed with $H_2O$, dried, and the solvent evaporated to give an oil. The HCl salt (0.34 g) crystallized from acetone as a tan solid, m.p. 186–190° C. (Compound 4).

EXAMPLE 5'

(+/−)-3-Hexyloxy-2-(1-azabicyclo[2.2.2]octyl-3-oxy)pyrazine

To a solution of lithium 1-hexyloxide (7.8 mL 1.6M n-butyllithium, 0.013 mol, 1-hexanol, 20 mL) was added (compound 2) (0.6 g, 0.0025 mol) and the reaction heated to 80° C. overnight. The solution was cooled, treated with 1N HCl (15 mL) and the solvent evaporated. The residue was suspended in $H_2O$, the mixture washed with ether, and made basic. The aqueous fraction was extracted with EtOAc, the extracts dried, and the solvent evaporated to give an oil. The HCl salt (0.34 g) crystallized from EtOAc as a hemihydrate, m.p. 162–164° C. (Compound 5).

EXAMPLE 6'

(+/−)-3-Butylthio-2-(1-azabicyclo[2.2.2]octyl-3-oxy)pyrazine

A solution of 1-butanethiol (1.1 mL) in THF (100 mL) was treated with 1.6M n-butyl lithium in hexane (4.7 mL, 0.0075 mol). After 10 min, (compound 2) (0.6 g, 0.0025 mol) was added and the reaction heated to reflux for 3 h. The solvent was evaporated, the residue acidified with cold dilute HCl, and the mixture extracted with ether. The aqueous was made basic and extracted with ether. The ether was dried and the solvent evaporated to give a clear liquid. The HCl salt (0.59 g) crystallized from EtOAc as white crystals, m.p. 192–193° C. (Compound 6).

EXAMPLE 7'

(+/−)-3-Pentylthio-2-(1-azabicyclo[2.2.2]octyl-3-oxy)pyrazine

A solution of 1-pentanethiol (1.2 mL) in THF (50 mL) was treated with 1.6M n-butyl lithium in hexane (4.7 mL, 0.0075 mol). After 10 min, (compound 2) (0.6 g, 0.0025 mol) was added and the reaction heated to reflux for 2 h. The solvent was evaporated, the residue acidified with cold dilute HCl, and the mixture extracted with ether. The aqueous was made basic and extracted with ether. The aqueous was made basic and extracted with EtOAc. The EtOAc was dried and the solvent evaporated to give a clear liquid. The HCl salt (0.44 g) crystallized from EtOAc, m.p. 169–171° C. (Compound 7).

EXAMPLE 8'

(+/−)-2-(1-Azabicyclo[2.2.2]octyl-3-oxy)pyrazine

A suspension of 60% NaH in oil (1 g, 0.025 mol) in DMF (30 mL) was treated with 1-azabicyclo[2.2.2]octan-3-ol (3.28 g, 0.025 mol) and the mixture heated to 50° C. for 65 min. The mixture was treated dropwise with 2-chloropyrazine (3.16 g, 0.027 mol) and heating continued for 3 h. Heating was discontinued and the reaction stirred overnight. The solvent was evaporated, the residue treated with water, acidified, and extracted with ether. The extracts were dried, the solvent evaporated, and the residue purified by radial chromatography (30% MeOH-EtOAc-trace $NH_4OH$) to give an oil. The HCl salt (2.07 g) crystallized from MeOH-EtOAc, m.p. 256–258° C. (Compound 8).

EXAMPLE 9'

(+/−)-3-(1-Pentyloxy)-2-(1-azabicyclo[2.2.2]octyl-3-oxy)pyrazine

To a solution of lithium 1-pentoxide (1.6M n-butyllithium, 7.6 mL, 0.012 mol, 1-pentanol, 20 mL) was added (Compound 2) (0.58 g, 0.0024 mol) and the reaction heated to 90° C. overnight. The solution was acidified and the solvent evaporated. The residue was suspended in $H_2O$, extracted with ether, and the aqueous solution made basic. the aqueous fraction was extracted with EtOAc, the extracts washed with $H_2O$, dried, and the solvent evaporated to give an oil. The oil was purified by raidal chromatography (10% EtOH-1% $NH_4OH$-$CHCl_3$) and the HCl salt (0.2 g) crystallized from EtOAc as a white powder, m.p. 163–165° C. (Compound 9).

EXAMPLE 10'

(+/−) -3-Methoxy-2-(1-azabicyclo[2.2.2]octyl-3-oxy)pyrazine

To a solution of sodium methoxide (Na, 0.4 g, 0.0174 mol, methanol, 25 mL) was added (compound 2) (0.8 g, 0.0033 mol) and the reaction heated to reflux overnight. The solvent was evaporated, the residue suspended in $H_2O$, and the mixture extracted with EtOAc. The extracts were dried, the solvent evaporated, and the residue purified by radial chromatography (10% EtOH-1% $NH_4OH$-$CHCl_3$). The HCl salt (0.34 g) crystallized from 2-propanol as a hemihydrate, m.p. 215–218° C. (Compound 10).

EXAMPLE 11'

(+/−)-3-Ethoxy-2-(1-azabicyclo[2.2.2]octyl-3-oxy)pyrazine

To a solution of sodium ethoxide (Na, 0.4 g, 0.0174 mol, ethanol, 25 mL) was added (compound 2) (0.8 g, 0.0033 mol) and the reaction heated to reflux overnight. The solvent was evaporated, the residue suspended in $H_2O$, and the mixture extracted with EtOAc. The extracts were dried, the solvent evaporated, and the residue purified by radial chromatography (10% EtOH-1% $NH_4OH$-$CHCl_3$). The HCl salt (0.086 g) crystallized from 2-propanol, m.p. 215–218° C. (compound 11).

EXAMPLE 12'

(+/−)-3-(1-Hexylthio)-2-(1-azabicyclo[2.2.2]octyl-3-oxy)pyrazine

A solution of 1-hexanethiol (1.4 mL) in THF (50 mL) was treated with 1.6M n-butyllithium in hexane (4.7 mL, 0.0075 mol). After 10 min, (compound 2) (0.6 g, 0.0025 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried and the solvent evaporated to give a clear liquid. The HCl salt (0.57 g) crystallized from EtOAc, m.p. 171–174° C. (Compound 12).

EXAMPLE 13'

(+/−)-3-Methylthio-2-(1-azabicyclo[2.2.2]octyl-3-oxy)pyrazine

A suspension of NaH (0.42 g, 0.018 mol) in DMF (25 mL) was treated with 5.19M methanethiol in DMF (6.44 mL, 0.033 mol). After 10 min, (compound 2) (0.8 g, 0.0033 mol) was added and the reaction heated to 50° C. for 3 h. The reaction was cooled, acidified, and the solvent evaporated. The residue was suspended in cold water, extracted with ether, the aqueous made basic, and the mixture extracted with EtOAc. The EtOAc was dried and the solvent evaporated to give a clear liquid. The HCl salt (0.63 g) crystallized from MeOH-EtOAc, m.p. 243–247° C. (Compound 13).

EXAMPLE 14'

(+/−)-3-Ethylthio-2-(1-azabicyclo[2.2.2]octyl-3-oxy) pyrazine

A solution of ethanethiol (2.6 mL) in THF (90 mL) was treated with 1.6M n-butyllithium in hexane (9 mL, 0.0167 mol). After 15 min, (compound 2) (0.6 g, 0.0025 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried, the solvent evaporated, and the residue purified by radial chromatography (5% EtOH-0.5% NH$_4$OHCHCl$_3$). The HCl salt (0.48 g) crystallized from EtOAc, m.p. 269–272° C. (Compound 14).

EXAMPLE 15'

(+/−)-3-(1-Propylthio-2-(1-azabicyclo[2.2.2]octyl-3-oxy)pyrazine

A solution of 1-propanethiol (2.7 mL) in THF (90 mL) was treated with 1.6M n-butyllithium in hexane (7 mL, 0.0117 mol). After 15 min, (compound 2) (0.7 g, 0.0029 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried, the solvent evaporated to give an oil. The HCl salt (0.76 g) crystallized from MeOH-EtOAc, m.p. 231–234° C. (Compound 15).

EXAMPLE 16'

(+/−)-3-(1-Heptylthio-2-(1-azabicyclo[2.2.2]octyl-3-oxy)pyrazine

A solution of 1-heptanethiol (4.9 mL) in THF (90 mL) was treated with 1.6M n-butyllithium in hexane (7 mL, 0.0117 mol). After 15 min, (compound 2) (0.7 g, 0.0029 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried, the solvent evaporated to give an oil. The HCl salt (0.767 g) crystallized from MeOH-EtOAc as a hemihydrate, m.p. 169–173° C. (Compound 16).

EXAMPLE 17'

3-(1-Butylthio-2-(2-(dimethylamino)ethoxy)pyrazine

A solution of 2-dimethylaminoethanol (2.13 mL, 0.021 mol) in THF (130 mL) was treated with 1.6M n-butyllithium in hexane (13.1 mL, 0.021 mol) with cooling in an ice-water bath. To the solution was added 2,3-dichloropyrazine (3.13 g, 0.021 mol) and the reaction heated to reflux overnight. The solvent was evaporated, the residue acidified with cold 1N HCl, and the mixture extracted with ether. The aqueous was made basic and extracted with EtOAc. The extracts were washed with water, dried, and the solvent evaporated to give a clear oil (3.86 g). The oil was added to a solution of lithium 1-butanethioxide (1.6M n-butanethioxide (1.6M n-butyllithium, 17 mL, 0.0273 mol, 1-butanethiol, 19.7 mL, 0.184 mol) in THF (100 mL), the reaction heated to reflux for 2 h, heating removed, and the reaction stirred over the weekend. The solvent was evaporated, the residue dissolved in dilute HCl, and the mixture extracted with ether. The aqueous phase was made basic, extracted with EtOAc, the extracts dried, and the solvent evaporated. The residue was purified by radial chromatography (5% EtOH-0.5% NH$_4$OH-CHCl$_3$) to give an oil (3.4 g). The HCl salt crystallized from EtOAc to give a white solid, m.p. 120–123° C. (Compound 17).

EXAMPLE 18'

3-(1-Butylthio)-2-(2-(trimethylamino)ethoxy) pyrazine iodide

A solution of (compound 17) (0.7 g, 0.0028 mol) in EtOAc (40 mL) was treated with iodomethane (0.4 mL) and the reaction stirred overnight. The white solid (1.04 g) was collected by filtration and dried, m.p. 140–142° C. (Compound 18).

EXAMPLE 19'

3-Chloro-2-[endo-(+,−)-6-(1-azabicyclo[3.2.1] octyloxy)]pyrazine

A solution of potassium t-butoxide (0.62 g, 0.0055 mol) in THF (10 mL) was treated with endo-(+,−)-1-azabicyclo [3.2.1]octan-6-ol (0.64 g, 0.005 mol). After 5 min, 2,3-dichloropyrazine (2 g, 0.0134 mol) was added and the reaction stirred overnight. The reaction was diluted with H$_2$O, acidified, and extracted with ether. The aqueous phase was made basic and extracted with EtOAc, the extracts dried, washed with brine, dried, and the solvent evaporated. The residue was purified by radial chromatography (20% EtOH-2% NH$_4$OH-CHCl$_3$) to give an oil. The HCl salt crystallized from acetone (0.44 g), m.p. 200° C. dec. (Compound 19).

EXAMPLE 20'

3-Methyl-2-[endo-(+,−)-6-(1-azabicyclo[3.2.1] octyloxy)]pyrazine

A solution of potassium t-butoxide (0.62 g, 0.0055 mol) in THF (10 mL) was treated with endo-(+,−)-1-azabicyclo [3.2.1]octan-6-ol (0.64 g, 0.005 mol). After 5 min, reaction was cooled in an ice-water bath and 2-chloro-3-methylpyrazine (1.3 g, 0.01 mol) was added in a single portion. Cooling was removed and the reaction stirred for 3 days. The solvent was evaporated, the residue diluted with H₂O, acidified, and extracted with ether. The aqueous phase was made basic and extracted with EtOAc, the extracts dried, washed with brine, dried, and the solvent evaporated. The residue was converted to an HCl salt and recrystallized from 2-propanol to give a flocculant powder (0.5 g), m.p. 240° C. dec. (Compound 20).

EXAMPLE 21'

2-[endo-(+,-)-6-(1-azabicyclo[3.2.1]octyloxy)]-pyrazine

A solution of potassium t-butoxide (0.62 g, 0.0055 mol) in THF (10 mL) was treated with endo-(+,-)-1-azabicyclo[3.2.1]octan-6-ol (0.64 g, 0.005 mol). After 5 min, reaction was cooled in an ice-water bath and 2-chloro-3-methylpyrazine (1.2 g, 0.01 mol) was added in a single portion. Cooling was removed and the reaction stirred 4 h. The solvent was evaporated, the residue diluted with H₂O, acidified, and extracted with ether. The aqueous phase was made basic and extracted with EtOAc, the extracts dried, washed with brine, dried, and the solvent evaporated. The solid residue was converted to an HCl salt and recrystallized from 2-propanol to give a white solid (0.92 g), m.p. 250° C. dec. (Compound 21).

EXAMPLE 22'

6-Chloro-2-[endo-(+,-)-6-(1-azabicyclo[3.2.1]octyloxy)]pyrazine

A solution of potassium t-butoxide (0.62 g, 0.0055 mol) in THF (10 mL) was treated with endo-(+,-)-1-azabicyclo[3.2.1]octan-6-ol (0.64 g, 0.005 mol). After 5 min, reaction was cooled in an ice-water bath and 2,6-dichloropyrazine (1 g, 0.0067 mol) was added in a single portion. Cooling was removed and the reaction stirred over night. The solvent was evaporated, the residue diluted with H₂O, acidified, and extracted with ether. The aqueous phase was made basic and extracted with EtOAc, the extracts dried, washed with brine, dried, and the solvent evaporated. The residue was purified by radial chromatography (20% EtOH-2% NH₄OH-CHCl₃). The HCl salt crystallized from acetone to give a white solid (0.33 g), m.p. 211–213° C. dec. (Compound 22).

EXAMPLE 23'

3-(1-butyloxy)-2-[endo-(+,-)-6-(1-azabicyclo[3.2.1]octyloxy)]-pyrazine

A solution of potassium t-butoxide (1 g, 0.0089 mol) in THF (20 mL) was treated with 1-butanol (1 mL). After 5 min, reaction was cooled in an ice-water bath and Compound 19 (0.65 g, 0.0027 mol) in THF (10 mL) was added. Cooling was removed and the reaction stirred for 3 days. The solvent was evaporated, the residue diluted with H₂O, acidified, and extracted with ether. The aqueous phase was made basic and extracted with EtOAc, the extracts dried, washed with brine, dried, and the solvent evaporated. The residue was purified by radial chromatography (20% EtOH-2% NH₄OH-CHCl₃). The HCl salt crystallized from EtOAc to give a white solid (0.23 g), m.p. 171.5–172.5° C. dec. (Compound 23).

EXAMPLE 24'

3-(1-butylthio)-2-[endo-(+,-)-6-(1-azabicyclo[3.2.1]octyloxy)]-pyrazine

A solution of potassium t-butoxide (1 g, 0.0089 mol) in THF (20 mL) was cooled in ice-water and treated with 1-butanethiol (1 mL). After 5 min, cooling was removed and Compound 19 (0.6 g, 0.0025 mol) in THF (10 mL) was added. After stirring overnight, the solvent was evaporated, the residue diluted with H₂O, acidified, and extracted with ether. The aqueous phase was made basic and extracted with EtOAc, the extracts dried, washed with brine, dried, and the solvent evaporated. The residue was purified by radial chromatography (20% EtOH-2% NH₄OH-CHCl₃). The HCl salt crystallized from EtOAc to give a white solid (0.64 g), m.p. 157–158° C. dec. (Compound 24).

EXAMPLE 25' endo-(8-Methyl-8-azabicyclo[3.2.1]octyl-3-oxy)]pyrazine

A solution of potassium tert-butoxide (0.62 g) in THF (15 mL) was treated with tropine (0.7 g). After 5 min, the reaction was cooled in ice-water and chloropyrazine (1.2 g) was added. The cooling was removed and the reaction stirred over night. The solvent was evaporated, the residue dissolved in cold 1N HCl, and the mixture exracted with ether. The aqueous fraction was made basic, extracted with EtOAc, the extracts washed with water, brine, the solvent dried, and the solvent evaporated. The residue was purified by radial chromatography eluting with 20%-EtOH-2%-NH₄OH-CHCl₃ to give endo-(8-methyl-8-azabicyclo[3.2.1]octyl-3-oxy)pyrazine (0.6 g) that was isolated as a HCl salt that crystallized from 2-propanol, m.p. 240° C., dec. (Compound 25).

EXAMPLE 26'

2-(2-Dimethylaminoethoxy)pyrazine

A solution of 2-dimethylaminoethanol (1 mL) in THF (20 mL) was treated with potassium tert-butoxide (1.2 g). After 5 min, chloropyrazine (2 g) was added and the reaction stirred 2 h. The solvent was evaporated, the residue suspended in cold water, the mixture acidified, and the mixture extracted with ether. The aqueous fraction was made basic and extracted with EtOAc. The extracts were dried, the solvent evaporated, and the residue purified by radial chromatography eluting with 10%-EtOH-1%-NH₄OH-CHCl₃ to give 2-(2-dimethylaminoethoxy)pyrazine (1.3 g). The HCl salt crystallized from 2-propanol as a white solid, m.p. 151–153° C. (Compound 26).

EXAMPLE 27'

2-(2-Trimethylaminoethoxy)pyrazine iodide

A solution of the free base of Compound 26 (0.7 g) in EtOAc (40 mL) was treated with methyl iodide (1 mL) and the reaction stirred over night. The resulting solid was collected and dried to give 2-(2-trimethylaminoethoxy) pyrazine iodide as a off white solid (1.34 g), m.p. 164° C., dec. (Compound 27).

EXAMPLE 28'

(S)-2-(1-Methyl-2-pyrrolidinylmethoxy)pyrazine

A solution of (S)-1-methyl-2-pyrrolidinemethanol (1.15 g) in THF (45 mL) was treated with potassium tert-butoxide (1.2 g). After 10 min, chloropyrazine was added and the reaction stirred for 1.5 h. The reaction was quenched with 5N HCl (4 mL) and the solvent evaporated. The residue was suspended in water and extracted with ether. The aqueous fraction was made basic and extracted with CHCl₃. The extracts were dried, the solvent evaporated, and the residue purified by radial chromatography eluting with 20%-EtOH-2%-NH$_4$OH-CHCl$_3$ to give (S)-2-(1-methyl-2-pyrrolidinylmethoxy)pyrazine (1.1). The HCl salt crystallized from EtOAc as a white solid, m.p. 121–122° C. (Compound 28).

EXAMPLE 29'

(±)-endo-2-Propylthio-3-(1-azabicyclo[3.2.1]octyl-6-oxy)pyrazine

Potassium t-butoxide (0.9 g, 8 mmoles) was added at 0° C. to propanethiol (0.61 g, 8 mmoles) in 20 ml THF and stirred for 5 min. Compound 19 (0.5 g, 2 mmoles) was added and the reaction stirred for 24 hr at room temperature. 200 ml of 1N HCl was added and the aqueous solution washed with ethyl acetate. The pH was adjusted to 12.0. The product was extracted with ethyl acetate, dried over sodium sulfate and evaporated. The HCl salt was formed in ether and filtered to yield (±)-endo-2-propylthio-3-(1-azabicyclo[3.2.1]octyl-6-oxy)pyrazine hydrochloride (0.38 g), m.p. 159–160° C. (Compound 29).

The following compounds were prepared in substantially the same manner as Compound 29 by substituting the appropriate alkylthiol for propanethiol.

EXAMPLE 30'

(±)-endo-2-Pentylthio-3-(1-azabicyclo[3.2.1]octyl-6-oxy)pyrazine

Obtained from Compound 19 and pentanethiol in 60% yield, m.p. 159–160° C. (Compound 30).

EXAMPLE 31'

(±)-endo-2-(2-Methylpropylthio)-3-(1-azabicyclo[3.2.1]octyl-6-oxy)pyrazine

Obtained from Compound 19 and 2-methylpropanethiol in 8% yield, m.p. 142–143° C. (Compound 31).

EXAMPLE 32'

(±)-endo-2-Ethylthio-3-(1-azabicyclo[3.2.1]octyl-6-oxy)pyrazine

Obtained from Compound 19 and ethanethiol in 53% yield, m.p. 196–197° C. (Compound 32).

EXAMPLE 33'

(±) -endo-2-(2,2,2,-Trifluoroethylthio)-3-(1-azabicyclo[3.2.1]octyl-6-oxy)pyrazine Obtained from Compound 19 and 2,2,2-trifluoroethanethiol in 14% yield, m.p. 116–117° C. (Compound 33).

EXAMPLE 34'

(±)-endo-2-(trans-2-Butenylthio)-3-(1-azabicyclo[3.2.1]octyl-6-oxy)pyrazine

Obtained from Compound 19 and trans-2-butenethiol in 13% yield, m.p. 128–130° C. (Compound 34).

EXAMPLE 35'

(±)-endo-2-(4,4,4-Trifluorobutylthio)-3-(1-azabicyclo[3.2.1]octyl-6-oxy)pyrazine Obtained from Compound 19 and 4,4,4-trifluorobutanethiol in 30% yield, m.p. 173–174° C. (Compound 35).

EXAMPLE 36'

(±)-endo-2-(2-propenylthio)-3-(1-azabicyclo[3.2.1]octyl-6-oxy)pyrazine

Obtained from Compound 19 and 2-propenethiol in 70% yield, m.p. 254–255° C. (Compound 36).

EXAMPLE 37'

(±)-endo-2-(3-Methylbutylthio)-3-(1-azabicyclo[3.2.1]octyl-6-oxy)pyrazine

Obtained from Compound 19 and 3-methylbutanethiol in 26% yield, m.p. 174–176° C. (Compound 37).

EXAMPLE 38'

(±)-endo-2-(4-Trifluoromethoxybenzylthio)-3-(1-azabicyclo[3.2.1]octyl-6-oxy)pyrazine Obtained from Compound 19 and 4-trifluoromethoxybenzylthiol in 57% yield, m.p. 175–176° C. (Compound 38).

EXAMPLE 39'

(±)-endo-2-Propylthio-6-(1-azabicyclo[3.2.1]octyl-6-oxy)pyrazine

Obtained from Compound 22 and propanethiol in 11% yield as a foam. (Compound 39).

EXAMPLE 40'

(±)-endo-2-(2.2.2-Trifluoroethylthio)-6-(1-azabicyclo[3.2.1]octyl-6-oxy)pyrazine Obtained from Compound 22 and 2,2,2-trifluoroethanethiol in 7% yield, m.p. 125–126° C. (Compound 40).

EXAMPLE 41'

(±)-endo-2-(2-Methoxyethylthio)-3-(1-azabicyclo[3.2.1]octyl-6-oxy)pyrazine

Compound 19 (1.15 g, 4.7 mmoles) and sodium sulfide (Na$_2$S.9H$_2$O), 1.68 g, 7 mmoles) were heated in 30 ml DMF at 50° C. for 3.5 hr, cooled to 0° C. and 2-Bromoethylmethylether (1.3 g, 9 mmoles) added. The reaction was stirred at room temperature overnight and diluted with ethyl acetate and 100 ml of 5N HCl. The aqueous layer was washed with ethyl acetate and the pH adjusted to 12.0. The product was extracted with ethyl acetate, dried over sodium sulfate, condensed and purified by HPLC eluted with 94%CHCl$_3$/5% ethanol/1% ammonium hydroxide. The HCl salt was formed in ether and filtered to give (±)-endo-2-(2-Methoxyethylthio)-3-(1-azabicyclo[3.2.1]octyl-6-oxy)pyrazine hydrochloride (0.3 g), m.p. 165–166° C. (Compound 41).

The following compounds were prepared in substantially the same manner as Compound 41 substituting the appropriate alkylhalide for 2-bromoethylmethylether.

EXAMPLE 42'

(±)-endo-2-(3-Phenyl-2-propenylthio)-3-(1-azabicyclo[3.2.1]octyl-6-oxy)pyrazine

Obtained from Compound 19 and cinnamyl bromide in 36% yield, m.p. 165–167° C. (Compound 42).

EXAMPLE 43'

Alternate Synthesis of Compound 19

A sample of (±)-(endo)-1-Azabicyclo[3.2.1]octan-6-ol (3.0 g, 23.6 mmoles, was added to a stirred solution of potassium t-butoxide (2.9 g, 26 mmoles) in 60 ml THF at room temperature. The reaction was cooled to 5° C. and 2,3-dichloropyrazine (7.03 g, 47 mmoles) in 15 ml THF was added. The solution was stirred at room temperature for 2 hrs, condensed, and diluted with water and ethyl acetate. The organic solution was dried and condensed. Purification by HPLC eluting with 94% $CHCl_3$, 5% ethanol, 1% ammonium hydroxide yielded 4.9 g, (Compound 19).

We claim:

1. A composition for treating pain comprising an analgesic dose of a First Compound selected from the group consisting of:

Formula I

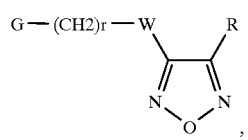

Formula I'

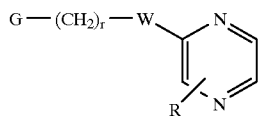

wherein

W is oxygen or sulphur;

R is hydrogen, amino, halogen, $NHR^6$, $NR^6R^7$, $R^4$, $—OR^4$, $—SR^4$, $—SOR^4$, $—SO_2R^4$, $C_{3-10}$-cycloalkyl, $C_{4-12}$-(cycloalkylalkyl), $—Z—C_{3-10}$-cycloalkyl and $—Z—C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $—CF_3$, $—CN$, Y, phenyl or phenoxy wherein phenyl or phenoxy is optionally substituted with halogen, $—CN$, $C_{1-4}$-alkyl, $C_{1-4}$-alkoxy, $—OCF_3$, $—CF_3$, $—CONH_2$ or $—CSNH_2$; or R is phenyl or benzyloxycarbonyl, each of which is optionally substituted with halogen, $—CN$, $C_{1-4}$-alkyl, $C_{1-4}$-alkoxy, $—OCF_3$, $—CF_3$, $—CONH_2$ or $—CSNH_2$; or R is $—OR^5Y$, $—SR^5Y$, $OR^5—Z—Y$, $—SR^5ZY$, $—O—R^5—Z—R^4$ or $—S—R^5—Z—R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

het-1

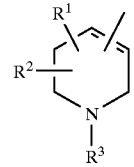
het-2

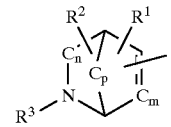
het-3

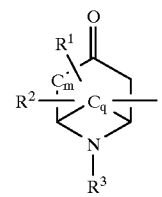
het-4

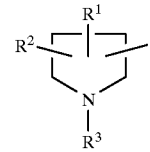
het-5

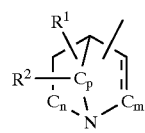
het-6

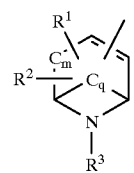
het-7 or G can optionally be substituted $C_3–C_8$ cycloalkyl or optionally substituted $C_{1-6}$-alkyl wherein the substitution is $—NR^6R^7$;

$R^6$ and $R^7$ independently are hydrogen, $C_{1-6}$-alkyl; or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with $—OH$, $—COR^{6'}$, $CH_2—OH$, halogen, $—NH_2$, carboxy, or phenyl;

$R^3$ is hydrogen, $C_{1-5}$-alkyl, $C_{2-5}$-alkenyl or $C_{2-5}$-alkynyl;

$R^{6'}$ is hydrogen, $C_{1-6}$-alkyl;

n is 0, 1 or 2;

m is 0, 1 or 2;

p is 0, 1 or 2;

q is 1 or 2;

r is 0, 1 or 2;

....... is a single or double bond; and

Formula I$^{1'}$

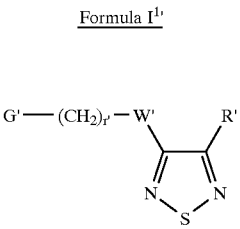

(I$^{1'}$)

wherein

W' is oxygen or sulfur;

R' is hydrogen, amino, halogen, NHR$^{6'}$, NR$^{6'}$R$^{7'}$, R$^{4'}$, —OR$^{4'}$, —SR$^{4'}$, —SOR$^{4'}$, —SO$_2$R$^{4'}$, C$_{3-10}$-cycloalkyl, C$_{4-12}$-(cycloalkylalkyl), —Z'—C$_{3-10}$-cycloalkyl and —Z'—C$_{4-12}$-(cycloalkylalkyl) wherein R$^{4'}$ is C$_{1-15}$-alkyl, C$_{2-15}$-alkenyl, C$_{2-15}$-alkynyl, each of which is optionally substituted with one or more halogen(s), —CF$_3$, —CN, Y', phenyl or phenoxy wherein phenyl or phenoxy is optionally substituted with halogen, —CN, C$_{1-4}$-alkyl, C$_{1-4}$-alkoxy, —OCF$_3$, —CF$_3$, —CONH$_2$ or —CSNH$_2$; or R' is phenyl or benzyloxycarbonyl, each of which is optionally substituted with halogen, —CN, C$_{1-4}$-alkyl, C$_{1-4}$-alkoxy, —OCF$_3$, —CF$_3$, —CONH$_2$ or —CSNH$_2$; or R' is —OR$^{5'}$Y', —SR$^{5'}$Y', OR$^{5'}$—Z'—Y', —SR$^{5'}$Z'Y', —O—R$^{5'}$—Z—R$^{4'}$ or —S—R$^{5'}$—Z'—R$^{4'}$ wherein Z' is oxygen or sulphur, R$^{5'}$ is C$_{1-15}$-alkyl, C$_{2-15}$-alkenyl, C$_{2-15}$-alkynyl, and Y' is a 5 or 6 membered heterocyclic group; and G' is selected from one of the following azacyclic or azabicyclic ring systems:

het-1

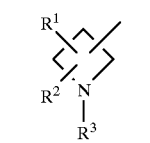

het-2

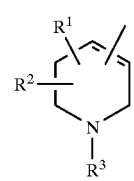

het-3

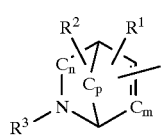

het-4

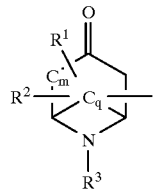

het-5

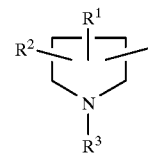

het-6

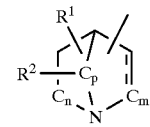

het-7

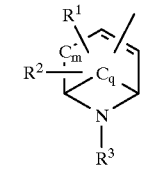

or G' can optionally be substituted C$_3$-C$_8$ cycloalkyl or optionally substituted C$_{1-6}$-alkyl wherein the substitution is —NR$^{6'}$R$^{7'}$;

R$^{6'}$ and R$^{7'}$ independently are hydrogen, C$_{1-6}$-alkyl; or

R$^{6'}$ and R$^{7'}$ together with the nitrogen atom optionally form a 4- to 6-member ring;

R$^1$ and R$^2$ independently are hydrogen, C$_{1-15}$-alkyl, C$_{2-5}$-alkenyl, C$_{2-5}$-alkynyl, C$_{1-10}$-alkoxy, C$_{1-5}$-alkyl substituted with —OH, —COR$^{6''}$, CH$_2$—OH, halogen, —NH$_2$, carboxy, or phenyl;

R$^3$ is hydrogen, C$_{1-5}$-alkyl, C$_{2-5}$-alkenyl or C$_{2-5}$-alkynyl;

R$^{6''}$ is hydrogen, C$_{1-15}$-alkyl n is 0, 1 or 2;

m is 0, 1 or 2;

p is 0, 1 or 2;

q is 1 or 2;

r is 0, 1 or 2;

....... is a single or double bond; or a pharmaceutically acceptable salt or solvate thereof;

and one or more Synergistic Analgesics in a weight ratio of First Compound to Synergistic Analgesic of from about 1 to about 1000.

2. A composition as claimed by claim 1 wherein the First Compound is selected from the group consisting of Formula I$^{1'}$ and Formula I; or a pharmaceutically acceptable salt or solvate thereof.

3. A composition as claimed by claim 1 wherein the Synergistic Analgesic is a nonsteroidal anti-inflammatory drug.

4. A composition as claimed by claim 3 wherein the nonsteroidal anti-inflammatory drug is selected from the group consisting of indomethacin, ibuprofen, naproxen, fenoprofen, tolmetin, sulindac, meclofenamate, keoprofen, piroxicam, flurbiprofen, and diclofenac.

5. A composition as claimed by claim 3 wherein the nonsteroidal anti-inflammatory drug is ibuprofen.

6. A composition as claimed by claim 3 wherein the First Compound is selected from the group consisting of Formula I and Formula I¹', or a pharmaceutically acceptable salt or solvate thereof.

7. A composition as claimed by claim 3 wherein the First Compound is selected from the group consisting of (±)-3-Methoxy-4-(1-azabicyclo[2.2.2]octyl-3-oxy)-1,2,5-thiadiazole, (±)-3-Ethoxy-4-(1-azabicyclo[2.2.2]octyl-3-oxy)-1,2,5-thiadiazole, (±)-3-Propyloxy-4-(1-azabicyclo[2.2.2]octyl-3-oxy)-1,2,5-thiadiazole, (±)-3-Butyloxy-4-(1-azabicyclo[2.2.2]octyl-3-oxy)-1,2,5-thiadiazole, (±)-3-Pentyloxy-4-(1-azabicyclo[2.2.2]octyl-3-oxy)-1,2,5-thiadiazole, (±)-3-Hexyloxy-4-(1-azabicyclo[2.2.2]octyl-3-oxy)-1,2,5-thiadiazole, (±)-3-(4-Methylpentyloxy)-4-(1-azabicyclo[2.2.2]octyl-3-oxy)-1,2,5-thiadiazole, (±)-3-Chloro-4-(1-azabicyclo[2.2.2]octyl-3-oxy)-1,2,5-thiadiazole, (±)-3-Propylthio-4-(1-azabicyclo[2.2.2]octyl-3-oxy)-1,2,5-thiadiazole, (±)-3-Butylthio-4-(1-azabicyclo[2.2.2]octyl-3-oxy)-1,2,5-thiadiazole, (±)-3-Pentylthio-4-(1-azabicyclo[2.2.2]octyl-3-oxy)-1,2,5-thiadiazole, (S)-3-Pentylthio-4-(1-azabicyclo[2.2.2]octyl-3-oxy)-1,2,5-thiadiazole, (±)-3-Hexylthio-4-(1-azabicyclo[2.2.2]octyl-3-oxy)-1,2,5-thiadiazole, (±)-3-(3,3-Dimethylbutylthio)-4-(1-azabicyclo[2.2.2]octyl-3-oxy)-1,2,5-thiadiazole, (±)-3-(2-(2-Thienylthio)ethylthio)-4-(1-azabicyclo[2.2.2]octyl-3-oxy)-1,2,5-thiadiazole, (±)-3-(2,2,3,3,3-Pentafluoropropylthio)-4-(1-azabicyclo[2.2.2]octyl-3-oxy)-1,2,5-thiadiazole, (±)-3-(3-(2-Thienyl)propylthio)-4-(1-azabicyclo[2.2.2]octyl-3-oxy)-1,2,5-thiadiazole, (±)-3-Butylthio-4-((1-azabicyclo[2.2.2]octan-3-yl)methoxy)-1,2,5-thiadiazole, (±)-Exo-3-pentylthio-4-(1-azabicyclo[3.2.1]octyl-6-oxy)-1,2,5-thiadiazole, (±)-Endo-3-pentylthio-4-(1-azabicyclo[3.2.1]octyl-6-oxy)-1,2,5-thiadiazole, (±)-Endo-3-butyloxy-4-(1-azabicyclo[2.2.1]heptyl-3-oxy)-1,2,5-thiadiazole, (±)-Exo-3-butyloxy-4-(1-azabicyclo[2.2.1]heptyl-3-oxy)-1,2,5-thiadiazole, (±)-3-Butyloxy-4-(3-pyrrolidinyloxy)-1,2,5-thiadiazole, (±)-3-Butyloxy-4-(1-methyl-3-pyrrolidinyloxy)-1,2,5-thiadiazole, (±)-3-Butylthio-4-(1-methyl-3-piperidyloxy)-1,2,5-thiadiazole, 3-Butylthio-4-(1-methyl-4-piperidyloxy)-1,2,5-thiadiazole, (S)-3-Butyloxy-4-(1-methyl-2-pyrrolidinylmethoxy)-1,2,5-thiadiazole, (S)-3-Butyloxy-4-(2-pyrrolidinylmethoxy)-1,2,5-thiadiazole, 3-Butyloxy-4-(2-(dimethylamino)ethoxy)-1,2,5-thiadiazole, 3-Butylthio-4-(2-(diethylamino)ethoxy)-1,2,5-thiadiazole, 3-Butyloxy-4-(2-(trimethylamino)ethoxy)-1,2,5-thiadiazole iodide, (R)-3-Pentylthio-4-(1-azabicyclo[2.2.2]octyl-3-oxy)-1,2,5-thiadiazole, (±)-3-(4-Methylpentylthio)-4-(1-azabicyclo[2.2.2]octyl-3-oxy)-1,2,5-thiadiazole, (±)-3-(3-Phenylpropylthio)-4-(1-azabicyclo[2.2.2]octyl-3-oxy)-1,2,5-thiadiazole, (±)-3-(4-Cyanobenzylthio)-4-(1-azabicyclo[2.2.2]octyl-3-oxy)-1,2,5-thiadiazole, (±)-3-(4-Fluorobenzylthio)-4-(1-azabicyclo[2.2.2]octyl-3-oxy)-1,2,5- thiadiazole, (±)-3-(2-Phenylethylthio)-4-(1-azabicyclo[2.2.2]octyl-3-oxy)-1,2,5-thiadiazole, (±)-3-(2-Phenyloxyethylthio)-4-(1-azabicyclo[2.2.2]octyl-3-oxy)-1,2,5-thiadiazole, Endo-3-butyloxy-4-(N-methyl-8-azabicyclo[3.2.1]octyl-3-oxy)-1,2,5-thiadiazole, (±)-Exo-3-butyloxy-4-(6-(N-methyl-8-azabicyclo[3.2.1]octan-3-onoxy))-1,2,5-thiadiazole, (±)-Exo-3-chloro-4-(1-azabicyclo[3.2.1]octyl-6-oxy)-1,2,5-thiadiazole, (±)-Endo-3-chloro-4-(1-azabicyclo[3.2.1]octyl-6-oxy)-1,2,5-thiadiazole, (±)-Endo-3-(4-cyanobenzylthio)-4-(1-azabicyclo[3.2.1]octyl-6-oxy)-1,2,5-thiadiazole, 3-Butyloxy-4-(3-azetidinyloxy)-1,2,5-thiadiazole, 3-Butylthio-4-(3-azetidinyloxy)-1,2,5-thiadiazole, (±)-Trans-3-butyloxy-4-(2-dimethylaminocyclopentyloxy)-1,2,5-thiadiazole, (±)-3-Butylthio-4-(3-pyrrolidinyloxy)-1,2,5-thiadiazole, (±)-3-(2-(2-(5-(2-Thienyl)thienyl)thio)ethylthio)-4-(1-azabicyclo[2.2.2]octyl-3-oxy)-1,2,5-thiadiazole, (±)-3-(2-(5-(2-Thienyl)thienyl)thio)-4-(1-azabicyclo[2.2.2]octyl-3-oxy)-1,2,5-thiadiazole, (±)-3-(3-N-(2-Thiazolidonyl)propylthio)-4-(1-azabicyclo[2.2.2]octyl-3-oxy)-1,2,5-thiadiazole, (±)3-Butylthio-4-(exo-2-azabicyclo[2.2.2]oct-6-yloxy)-1,2,5-thiadiazole, (±)3-(2,2,3,3,4,4,4-heptafluorobutyloxy)-4-[-3-(1-azabicyclo[2.2.2]octyloxy)]-1,2,5-thiadiazole, (±)3-(1-butylthio)-4-[endo-6-(1-azabicyclo[3.2.1]octyloxy)]-1,2,5-thiadiazole, (±)3-(3-phenylpropylthio)-4-[endo-6-(1-azabicyclo-[3.2.1]octyloxy)]-1,2,5-thiadiazole (±)3-[3-(4-fluorophenyl)propylthio]-4-[-3-(1-azabicyclo-[2.2.2]octyloxy)]-1,2,5-thiadiazole (±)3-(3-[4-(trifluoromethyl)phenyl]propylthio)-4-[-3-(1-azabicyclo[2.2.2]octyloxy)]-1,2,5-thiadiazole; and (±)³-(1-Butylamino)-4-[-3-(1-azabicyclo[2.2.2]octyloxy)]-1,2,5-thiadiazole; and (±)-3-(2-Methylthioethyl)-4-(1-azabicyclo[2.2.2]octyl-3-oxy)-1,2,5-thiadiazole (±)-3-(1-Azabicyclo[2.2.2]octyl-3-oxy)-1,2,5-thiadiazole (±)-3-Hexyl-4-(1-azabicyclo[2.2.2]octyl-3-oxy)-1,2,5-thiadiazole (±)-3-Butylsulfonyl-4-(1-azabicyclo[2.2.2]octyl-3-oxy)-1,2,5-thiadiazole (±)-3-Propylsulfonyl-4-(1-azabicyclo[2.2.2]octyl-3-oxy)-1,2,5-thiadiazole
(±)-3-(4,4,4-Trifluorobutyloxy)-4-(1-azabicyclo[2.2.2]octyl-3-oxy)-1,2,5-thiadiazole
(±)-3-(2-Butynyloxy)-4-(1-azabicyclo[2.2.2]octyl-3-oxy)-1,2,5-thiadiazole
(±)-3-(Cyclopropylmethoxy)-4-(1-azabicyclo[2.2.2]octyl-3-oxy)-1,2,5-thiadiazole,
(±)-3-(3-Phenylpropynyloxy)-4-(1-azabicyclo[2.2.2]octyl-3-oxy)-1,2,5-thiadiazole
(±)-3-(3-Butenyloxy)-4-(1-azabicyclo[2.2.2]octyl-3-oxy)-1,2,5-thiadiazole
(±)-3-(trans-2-Butenyloxy)-4-(1-azabicyclo[2.2.2]octyl-3-oxy)-1,2,5-thiadiazole
(±)-3-(cis-2-Butenyloxy)-4-(1-azabicyclo[2.2.2]octyl-3-oxy)-1,2,5-thiadiazole
(±)-3-(2-Methoxyethoxy)-4-(1-azabicyclo[2.2.2]octyl-3-oxy)-1,2,5-thiadiazole
(±)-3-(2-Phenoxyethoxy)-4-(1-azabicyclo[2.2.2]octyl-3-oxy)-1,2,5-thiadiazole
(±)-3-(3-Butynoxy)-4-(1-azabicyclo[2.2.2]octyl-3-oxy)-1,2,5-thiadiazole
(±)-3-(2-Cyclopropylethoxy)-4-(1-azabicyclo[2.2.2]octyl-3-oxy)-1,2,5-thiadiazole
(±)-3-(2-(Methylthio)ethoxy)-4-(1-azabicyclo[2.2.2]octyl-3-oxy)-1,2,5-thiadiazole
(±)-3-(3-Chloropropoxy)-4-(1-azabicyclo[2.2.2]octyl-3-oxy)-1,2,5-thiadiazole
(±)-3-(4-Fluorobutyloxy)-4-(1-azabicyclo[2.2.2]octyl-3-oxy)-1,2,5-thiadiazole
(±)-3-(2-[4-Chlorophenoxy]ethoxy)-4-(1-azabicyclo[2.2.2]octyl-3-oxy)-1,2,5-thiadiazole
(±)-3-(3-[2-methoxy-5-pyridyl]propyloxy)-4-(1-azabicyclo[2.2.2]octyl-3-oxy)-1,2,5-thiadiazole
(±)-3-(trans-3-Chloro-2-propenyloxy)-4-(1-azabicyclo[2.2.2]octyl-3-oxy)-1,2,5-thiadiazole
(±)-3-(2-[4-Fluorophenoxy]ethoxy)-4-(1-azabicyclo[2.2.2]octyl-3-oxy)-1,2,5-thiadiazole
(±)-3-(4-Pentenyloxy)-4-(1-azabicyclo[2.2.2]octyl-3-oxy)-1,2,5-thiadiazole
(±)-3-(3-Fluoropropyloxy)-4-(1-azabicyclo[2.2.2]octyl-3-oxy)-1,2,5-thiadiazole
(±)-3-(Cyclobutylmethoxy)-4-(1-azabicyclo[2.2.2]octyl-3-oxy)-1,2,5-thiadiazole
(±)-3-(3,3,3,2,2-Pentafluoropropyloxy)-4-(1-azabicyclo[2.2.2]octyl-3-oxy)-1,2,5-thiadiazole
(±)-3-(2-[Phenylthio]ethoxy)-4-(1-azabicyclo[2.2.2]octyl-3-oxy)-1,2,5-thiadiazole
(±)-3-(2-[1-napthyloxy]ethoxy)-4-(1-azabicyclo[2.2.2]octyl-3-oxy)-1,2,5-thiadiazole
(±)-3-(2-[4-Bromophenoxy]ethoxy)-4-(1-azabicyclo[2.2.2]octyl-3-oxy)-1,2,5-thiadiazole
(±)-3-(2-Hydroxyethoxy)-4-(1-azabicyclo[2.2.2]octyl-3-oxy)-1,2,5-thiadiazole
3-Butylthio-4-hydroxy-1,2,5-thiadiazole
(±)Exo-3-Butylthio-4-(1-azabicyclo[2.2.1]heptyl-3-oxy)-1,2,5-thiadiazole
(±)-3-(2-[3-{1,2,5-Thiadiazoyloxy}]ethoxy)-4-(1-azabicyclo[2.2.2]octyl-3-oxy)-1,2,5-thiadiazole
(±)-exo-3-Butyloxy-4-(7-azabicyclo[2.2.1]heptyl-3-oxy)-1,2,5-thiadiazole
(±)-3-Butyloxy-4-(3-piperidinyloxy)-1,2,5-thiadiazole
3-Butyloxy-4-(cis-1R-2-aminocyclopentanoxy)-1,2,5-thiadiazole
(±)-endo-3-Hexyloxy-4-(1-azabicyclo[3.2.1]octyl-6-oxy)-1,2, 5-thiadiazole
(5S,6S)-endo-3-Butylthio-4-(1-azabicyclo[3.2.1]octyl-6-oxy)-1,2,5-thiadiazole
(5R, 6R)-endo-3-Butylthio-4-(1-azabicyclo[3.2.1]octyl-6-oxy)-1,2,5-thiadiazole
(±)-trans-3-Butylthio-4-(1-azabicyclo[4.3.0]nonyl-5-oxy)-1,2,5-thiadiazole
(±)-cis-3-Butylthio-4-(1-azabicyclo[4.3.0]nonyl-5-oxy)-1,2,5-thiadiazole
(±)-trans-3-Butylthio-4-(2-dimethylaminocyclopentyloxy)-1,2,5-thiadiazole
3-Butylthio-4-(2-dimethylaminoethoxy)-1,2,5-thiadiazole
(±)-trans-3-Butylthio-4-(N-tert-butylcarboxy-4-hydroxy-pyrollidin-3-oxy)-1,2,5-thiadiazole
(±)-trans-3-Butylthio-4-(4-hydroxy-pyrollidin-3-oxy)-1,2,5-thiadiazole
(±)-endo-3-Butyloxy-4-(1-azabicyclo[3.2.1]octyl-6-oxy)-1,2,5-thiadiazole
(±)-3-(4-Phenylbutylthio)-4-(1-azabicyclo[2.2.2]octyl-3-oxy)-1,2,5-thiadiazole
(±)-3-(3-Phenyl-2-propenylthio)-4-(1-azabicyclo[2.2.2]octyl-3-oxy)-1,2,5-thiadiazole
(±)-3-(3-[4-Fluorophenyl]propan-3-onethio)-4-(1-azabicyclo[2.2.2]octyl-3-oxy)-1,2,5-thiadiazole
(±)-3-(3-[N-Phenothiazinyl]propylthio)-4-(1-azabicyclo[2.2.2]octyl-3-oxy)-1,2,5-thiadiazole
(±)-3-(3-[4-Fluorophenyl]-3-[4-fluorophenoxy]propylthio)-4-(1-azabicyclo[2.2.2]octyl-3-oxy)-1,2,5-thiadiazole
(±)-3-(3-Phenyl-3-[4-trifluoromethylphenoxy]propylthio)-4-(1-azabicyclo[2.2.2]octyl-3-oxy)-1,2,5-thiadiazole
(±)-3-(4,4,4-Trifluorobutylthio)-4-(1-azabicyclo[2.2.2]octyl-3-oxy)-1,2,5-thiadiazole
(±)-3-(3-[3-Pyridyl]propylthio)-4-(1-azabicyclo[2.2.2]octyl-3-oxy)-1,2,5-thiadiazole
(±)-endo-3-(2-Phenoxyethylthio)-4-(1-azabicyclo[3.2.1]octyl-6-oxy)-1,2,5-thiadiazole
(±)-exo-3-Propythio-4-(2-methoxycarbonyl-2-azabicyclo[2.2.2]octyl-6-oxy)-1,2,5-thiadiazole
(±)-exo-3-Propylsulfonyl-4-(2-methoxycarbonyl-2-azabicyclo[2.2.2]octyl-6-oxy)-1,2,5-thiadiazole
(±)-exo-3-(4,4,4-Trifluorobutyloxy)-4-(2-methoxycarbonyl-2-azabicyclo[2.2.2)octyl-6-oxy)-1,2, 5-thiadiazole
(±)-exo-3-(4,4,4-Trifluorobutyloxy)-4-(2-azabicyclo[2.2.2]octyl-6-oxy)-1,2,5-thiadiazole
(±)-exo-3-(Hexyloxy)-4-(2-azabicyclo[2.2.2]octyl-6-oxy)-1,2,5-thiadiazole
(±)-endo-3-(4,4,4-Trifluorobutyloxy)-4-(2-azabicyclo[2.2.2]octyl-6-oxy)-1,2,5-thiadiazole
(±)-exo-3-(2-[Fluorophenoxy]ethylthio)-4-(2-methoxycarbonyl-2-azabicyclo[2.2.2]octyl-6-oxy)-1,2, 5-thiadiazole
(±)-exo-3-(2-[Fluorophenoxy]ethylthio)-4-(2-azabicyclo[2.2.2]octyl-6-oxy)-1,2,5-thiadiazole
(±)-endo-3-Propylthio-4-(1-azabicyclo[3.2.1]octyl-6-oxy)-1,2,5-thiadiazole (±)-endo-3-Propylsulfonyl-4-(1-azabicyclo[3.2.1]octyl-6-oxy)-1,2,5-thiadiazole (±)-endo-3-(4,4,4-Trifluorobutoxy)-4-(1-azabicyclo[3.2.1]octyl-6-oxy)-1,2,5-thiadiazole (±)-endo-3-(2-Butynyloxy)-4-(1-azabicyclo [3.2.1]octyl-6-oxy)-1,2,5-thiadiazole (±)-endo-3-(trans-2-Butenyloxy)-4-(1-azabicyclo[3.2.1]octyl-6-oxy)-1,2,5-thiadiazole (±)-endo-3-(2-Methylthioethoxy)-4-(1-azabicyclo[3.2.1]octyl-6-oxy)-1,2,5-thiadiazole (±)-endo-3-(2-(4-Methyl-1,3-thiazol-5-yl)ethoxy)-4-(1-azabicyclo[3.2.1]octyl-6-oxy)-1,2,5-thiadiazole (±)-endo-3-(4-Methylthiobenzyloxy)-4-(1-azabicyclo[3.2.1]octyl-6-oxy)-1,2,5-thiadiazole (±)-endo-3-(2-Thienylmethoxy)-4-(1-azabicyclo [3.2.1)octyl-6-oxy)-1,2,5-thiadiazole (±)-endo-3-(2-cyclohexenyloxy)-4-(1-azabicyclo[3.2.1]octyl-6-oxy)-1,2,5-thiadiazole (±)-endo-3-(3-Pentynyloxy)-4-(1-azabicyclo[3 .2.1]octyl-6-oxy)-1,2,5-thiadiazole (±)-endo-3-(3-Hexynyloxy)-4-(1-azabicyclo[3.2.1]octyl-6-oxy)-1,2,5-thiadiazole (±)-endo-3-(3-Chloropropoxy)-4-(1-azabicyclo[3.2.1]octyl-6-oxy)-1,2,5-thiadiazole (±)-endo-3-[2-(2-Napthalyl)ethoxy]-4-(1-azabicyclo[3.2.1]octyl-6-oxy)-1,2,5-thiadiazole (±)-endo-3-(4-Chloro-α-cyclopropyl-benzyloxy)-4-(1-azabicyclo [3.2.1]octyl-6-oxy)-1,2,5-thiadiazole (±)-endo-3-(4-Methyl-3-pentenyloxy)-4-(1-azabicyclo[3.2.1]octyl-6-oxy)-1,2,5-thiadiazole (±)-endo-3-(cis-2-Butenyloxy)-4-(1-azabicyclo[3 .2.1]octyl-6-oxy)-1,2,5-thiadiazole (±)-endo-3-(Cyclopropylmethoxy)-4-(1-azabicyclo[3.2.1]octyl-6-oxy)-1,2,5-thiadiazole (±)-endo-3-(2-Methoxyethoxy)-4-(1-azabicyclo[3.2.1]octyl-6-oxy)-1,2,5-thiadiazole (±)-endo-3-(3-Butenyloxy)-4-(1-azabicyclo[3.2.1]octyl-6-oxy)-1,2,5-thiadiazole (±)-endo-3-(2-cyclopropylethoxy)-4-(1-azabicyclo[3.2.1]octyl-6-oxy)-1,2,5-thiadiazole (±)-endo-3-(3-Butynyloxy)-4-(1-azabicyclo [3.2.1]octyl-6-oxy)-1,2,5-thiadiazole (±)-endo-3-(4,4,4,3,3,2,2-Heptafluorobutoxy)-4-(1-azabicyclo[3.2.1]octyl-6-oxy)-1,2,5-thiadiazole (±)-endo-3-[2-(3-Trifluoromethylphenyl)ethoxy]-4-(1-azabicyclo[3.2.1]octyl-6-oxy)-1,2,5-thiadiazole (±)-endo-3-[2-(2-Thienyl)ethoxy]-4-(1-azabicyclo[3.2.1]octyl-6-oxy)-1,2,5-thiadiazole (±)-endo-3-(3,3,3,2,2,Pentafluoropropoxy)-4-(1-azabicyclo[3.2.1]octyl-6-oxy)-1,2,5-thiadiazole (±)-endo-3-(2-Phenoxyethoxy)-4-(1-azabicyclo[3.2.1]octyl-6-oxy)-1,2,5-thiadiazole (±)-endo-3-(4-n-Butylbenzyloxy)-4-(1-azabicyclo[3.2.1]octyl-6-oxy)-1,2,5-thiadiazole (±)-endo-3-[3-(4-Methoxyphenyl)propoxy]-4-(1-azabicyclo[3.2.1]octyl-6-oxy)-1,2,5-thiadiazole (±)-endo-3-(4-Fluorobenzyloxy)-4-(1-azabicyclo[3.2.1]octyl-6-oxy)-1,2,5-thiadiazole (±)-endo-3-(2,4-Difluorobenzyloxy)-4-(1-azabicyclo[3.2.1]octyl-6-oxy)-1,2,5-thiadiazole (±)-endo-3-[4-(Trifluoromethoxy)benzyloxy]-4-(1-azabicyclo[3.2.1]octyl-6-oxy)-1,2,5-thiadiazole (±)-endo-3-(4-Fluorobutoxy)-4-(1-azabicyclo[3.2.1]octyl-6-oxy)-1,2,5-thiadiazole (±)-endo-3-(4-tert-Butylbenzyloxy)-4-(1-azabicyclo[3.2.1]octyl-6-oxy)-1,2,5-thiadiazole (±)-endo-3-(1-Cyclopropylethoxy)-4-(1-azabicyclo[3.2.1]octyl-6-oxy)-1,2,5-thiadiazole (±)-endo-3-(2-Cyclohexylethoxy)-4-(1-azabicyclo[3.2.1]octyl-6-oxy)-1,2,5-thiadiazole (±)-endo-3-(3-Methyl-2-butenyloxy)-4-(1-azabicyclo[3.2.1]octyl-6-oxy)-1,2,5-thiadiazole (±)-endo-3-(4-Cyclohexylbutoxy)-4-(1-azabicyclo[3.2.1]octyl-6-oxy)-1,2,5-thiadiazole (±)-endo-3-(3-Butyn-2-oxy)-4-(1-azabicyclo[3.2.1]octyl-6-oxy)-1,2,5-thiadiazole (±)-endo-3-(3-Methyl-3-phenylbutoxy)-4-(1-azabicyclo[3.2.1]octyl-6-oxy)-1,2,5-thiadiazole (±)-endo-3-(3-Fluoropropoxy)-4-(1-azabicyclo[3.2.1]octyl-6-oxy)-1,2,5-thiadiazole (±)-endo-3-[3-(2-Thienyl)propoxy]-4-(1-azabicyclo[3.2.1]octyl-6-oxy)-1,2,5-thiadiazole (±)-3-(2-[4-Fluorophenoxy]ethylthio)-4-(1-azabicyclo[2.2.2]octyl-3-oxy)-1,2,5-thiadiazole (±)-3-(2-Methylthioethyl)-4-(1-azabicyclo[2.2.2]octyl-3-oxy)-1,2,5-thiadiazole (±)-3-(1-Azabicyclo[2.2.2]octyl-3-oxy)-1,2,5-thiadiazole (±)-3-Hexyl-4-(1-azabicyclo[2.2.2]octyl-3-oxy)-1,2,5-thiadiazole 3-Butylthio-4-hydroxy-1,2,5-thiadiazole (±)-3-(2- [3-{1, 2, 5-Thiadiazoyloxy}]ethoxy)-4-(1-azabicyclo[2.2.2]octyl-3-oxy)-1,2,5-thiadiazole (+/−)-3-butylthio-4-(azabicyclo[2.2.2]octyl-3-oxy)-1,2,5-oxadiazole, (+/−)-3-(2-butyloxy)-4-[(+/−)-3-azabicyclo[2.2.2]octyloxy)-1,2,5-oxadiazole, (+/−)-3-butyloxy-4-[endo-(+/−)-6-[1-azabicyclo[3.2.1]octyloxy)]-1,2,5-oxadiazole, 3-(2,2,3,3,4,4,4-heptaflurorobutyloxy)-4-[(+/−)-3-(1-azabicyclo[2.2.2]octyloxy)]-1,2,5-oxadiazole, 3-methoxy-4-(1-azabicyclo[2.2.2]octyl-3-oxy)-1,2,5-oxadiazole, 3-pentylthio-4-(1-azabicyclo[2.2.2]ocytl-3-oxy)-1,2,5-oxadiazole, trans-3-butyloxy-4-(2-dimethylaminocyclopentyloxy)-1,2,5-oxadiazole, 3-butylthio-4-(3-azetidinyloxy)-1,2,5-oxadiazole, 3-(3-N-(2-thiazolidonyl)propylthio)-4-(1-azabicyclo[2.2.2]octyl-3-oxy)-1,2,5-oxadiazole, 3-chloro-4-(1-azabicyclo[3.2.1]octyl-6-oxy)-1,2,5-oxadiazole, 3-(2-2-thio-5-trifluoromethylthienyl)ethylthio)-4-azabicyclo[2.2.2]octyl-3-oxy)-1,2,5-oxadiazole, 3-butylthio-4-[3-±-endo-(1-azabicyclo[2.2.1]heptyloxy)]-1,2,5-oxadiazole, 3-hexyloxy-4-[6-±-endo-(2-azabicyclo[2.2.2]ocyloxy)]-1,2,5-oxadiazole, 3-(4,4,4-trifluorobutylthio)-4-[2-±-exo-(7-azabicyclo[2.2.1]heptyloxy)]-1,2,5-oxadiazole, 3-(2-phenoxyethylthio)-4-[3-±-endo-(1-azabicyclo[3.2.1]octyloxy)]-1,2,5-oxadiazole, 3-(5-hexenyloxy)-4-[7-±-endo-(2-azabicyclo[2.2.1]heptyloxy)]-1,2,5-oxadiazole, 3-butyl-4-[5-(1-azabicyclo[3.2.1]octyloxy)]-1,2,5-oxadiazole, 3-cyclobutylmethyl-4-[2-i-endo-(8-azabicyclo[3.2.1]octyloxy)]-1,2,5-oxadiazole, (+/−)-3-butylthio-4-(azabicyclo[2.2.2]octyl-3-oxy)-pyrazine, (+/−)-3-(2-butyloxy)-4-[(+/−)-3-azabicyclo[2.2.2]octyloxy)-pyrazine, (+/−)-3-butyloxy-4-[endo-(+/−)-6-[1-azabicyclo[3.2.1]octyloxy)]-pyrazine, 3-(2,2,3,3,4,4,4-heptaflurorobutyloxy)-4-[(+/−)-3-(1-azabicyclo[2.2.2]

octyloxy)]-pyrazine, 3-methoxy-4-(1-azabicyclo[2.2.2] octyl-3-oxy)-pyrazine, 3-pentylthio-4-(1-azabicyclo [2.2.2]ocytl-3-oxy)-pyrazine, trans-3-butyloxy-4-(2-dimethylaminocyclopentyloxy)-pyrazine, 3-butylthio-4-(3-azetidinyloxy)-pyrazine, 3-(3-N-(2-thiazolidonyl)propylthio)-4-(1-azabicyclo[2.2.2]octyl-3-oxy)-pyrazine, 3-chloro-4-(1-azabicyclo[3.2.1]octyl-6-oxy)-pyrazine, 3-(2-2-thio-5-trifluoromethylthienyl) ethylthio)-4-azabicyclo[2.2.2]octyl-3-oxy)-pyrazine, 3-butylthio-4-[3-+-endo-(1-azabicyclo[2.2.1] heptyloxy)]-pyrazine, 3-hexyloxy-4-[6-±-endo-(2-azabicyclo[2.2.2]ocyloxy)]-pyrazine, 3-(4,4,4-trifluorobutylthio)-4-[2-±-exo-(7-azabicyclo[2.2.1] heptyloxy)]-pyrazine, 3-(2-phenoxyethylthio)-4-[3-±-endo-(1-azabicyclo[3.2.1]octyloxy)]-pyrazine, 3-(5-hexenyloxy)-4-[7-±-endo-(2-azabicyclo[2.2.1] heptyloxy)]-pyrazine, 3-butyl-4-[5-(1-azabicyclo [3.2.1]octyloxy)]-pyrazine, and 3-cyclobutylmethyl-4-[2-±-endo-(8-azabicyclo[3.2.1]octyloxy)]-pyrazine, 2-[exo-(+/−)-3-[1-azabicyclo[3.2.1]octyloxy)] pyrazine, 3-butylthio-2-(1-azabicyclo[2.2.2]ocytl-3-oxy)]pyrazine, 3-butyloxy-2-[3-±-endo-(1-azabicyclo [2.2.1]heptyloxy)]pyrazine, 3-(2-butynyloxy)-2-[6-±-endo-(1-azabicyclo[3.2.1]octyloxy)pyrazine, 3-hexylthio-2-[6-±-exo-(2-azabicyclo[2.2.1] heptyloxy)]pyrazine, 3-(3-phenylpropynylthio)-2-[2-±-exo-(7-azabicyclo[2.2.1]heptyloxy)]pyrazine, 3-(2-methylthioethoxy)-2-[3-±-exo-(1-azabicyclo[3.2.1] octyloxy)]pyrazine, 3-propargyl-2-[4-(1-azabicyclo [2.2.1]heptyloxy)]pyrazine, and 3-cyclopropylmethylthio-2-[2-±-exo-(8-azabicyclo [3.2.1loctyloxy)]pyrazine; or a pharmaceutically acceptable salt or solvate thereof.

8. A composition as claimed by claim 1 wherein the Synergistic Analgesic is an opioid.

9. A composition as claimed by claim 8 wherein the First Compound is selected from the group consisting of Formula I and Formula I$^{1'}$ or a pharmaceutically acceptable salt or solvate thereof.

10. A composition as claimed by claim 8 wherein the First Compound is Formula I' or a pharmaceutically acceptable salt or solvate thereof.

11. A composition as claimed by claim 8 wherein the First Compound is selected from the group consisting of (±)-3-Ethoxy-4-(1-azabicyclo[2.2.2]octyl-3-oxy)-1,2,5-thiadiazole, (±)-3-Propyloxy-4-(1-azabicyclo[2.2.2]octyl-3-oxy)-1,2,5-thiadiazole, (±)-3-Butyloxy-4-(1-azabicyclo[2.2.2]octyl-3-oxy)-1,2,5-thiadiazole, (±)-3-Pentyloxy-4-(1-azabicyclo[2.2.2]octyl-3-oxy)-1,2,5-thiadiazole, (±)-3-Hexyloxy-4-(1-azabicyclo[2.2.2]octyl-3-oxy)-1,2,5-thiadiazole, (±)-3-(4-Methylpentyloxy)-4-(1-azabicyclo[2.2.2]octyl-3-oxy)-1,2,5-thiadiazole, (±)-3-Chloro-4-(1-azabicyclo[2.2.2]octyl-3-oxy)-1,2,5-thiadiazole, (±)-3-Propylthio-4-(1-azabicyclo[2.2.2]octyl-3-oxy)-1,2,5-thiadiazole, (±)-3-Butylthio-4-(1-azabicyclo[2.2.2]octyl-3-oxy)-1,2,5-thiadiazole, (±)-3-Pentylthio-4-(1-azabicyclo[2.2.2]octyl-3-oxy)-1,2,5-thiadiazole, (S)-3-Pentylthio-4-(1-azabicyclo[2.2.2]octyl-3-oxy)-1,2,5-thiadiazole, (±)-3-Hexylthio-4-(I-azabicyclo[2.2.2]octyl-3-oxy)-1,2,5-thiadiazole, (±)-3-(3,3-Dimethylbutylthio)-4-(1-azabicyclo[2.2.2] octyl-3-oxy)-1,2,5-thiadiazole, (±)-3-(2-(2-Thienylthio)ethylthio)-4-(1-azabicyclo[2.2.2] octyl-3-oxy)-1,2,5-thiadiazole, (±)-3-(2,2,3,3,3-Pentafluoropropylthio)-4-(1-azabicyclo [2.2.2]octyl-3-oxy)-1,2,5-thiadiazole, (±)-3-(3-(2-Thienyl)propylthio)-4-(1-azabicyclo[2.2.2) octyl-3-oxy)-1,2,5-thiadiazole, (±)-3-Butylthio-4-((1-azabicyclo[2.2.2]octan-3-yl) methoxy)-1,2,5-thiadiazole, (±)-Exo-3-pentylthio-4-(1-azabicyclo[3.2.1]octyl-6-oxy)-1,2,5-thiadiazole, (±)-Endo-3-pentylthio-4-(1-azabicyclo[3.2.1]octyl-6-oxy)-1,2,5-thiadiazole, (±)-Endo-3-butyloxy-4-(1-azabicyclo[2.2.1]heptyl-3-oxy)-1,2,5-thiadiazole, (±)-Exo-3-butyloxy-4-(1-azabicyclo[2.2.1)heptyl-3-oxy)-1,2,5-thiadiazole, (±)-3-Butyloxy-4-(3-pyrrolidinyloxy)-1,2,5-thiadiazole, (±)-3-Butyloxy-4-(1-methyl-3-pyrrolidinyloxy)-1,2,5-thiadiazole, (±)-3-Butylthio-4-(1-methyl-3-piperidyloxy)-1,2,5-thiadiazole, 3-Butylthio-4-(1-methyl-4-piperidyloxy)-1,2,5-thiadiazole, (S)-3-Butyloxy-4-(1-methyl-2-pyrrolidinylmethoxy)-1,2,5-thiadiazole, (S)-3-Butyloxy-4-(2-pyrrolidinylmethoxy)-1,2,5-thiadiazole, 3-Butyloxy-4-(2-(dimethylamino)ethoxy)-1,2,5-thiadiazole, 3-Butylthio-4-(2-(diethylamino)ethoxy)-1,2,5-thiadiazole, 3-Butyloxy-4-(2-(trimethylamino)ethoxy)-1,2,5-thiadiazole iodide, (R)-3-Pentylthio-4-(1-azabicyclo[2.2.2]octyl-3-oxy)-1,2,5-thiadiazole, (±)-3-(4-Methylpentylthio)-4-(1-azabicyclo[2.2.2]octyl-3-oxy)-1,2,5-thiadiazole, (±)-3-(3-Phenylpropylthio)-4-(1-azabicyclo[2.2.2]octyl-3-oxy)-1,2,5-thiadiazole, (±)-3-(4-Cyanobenzylthio)-4-(1-azabicyclo[2.2.2)octyl-3-oxy)-1,2,5-thiadiazole, (±)-3-(4-Fluorobenzylthio)-4-(1-azabicyclo[2.2.2]octyl-3-oxy)-1,2,5- thiadiazole, (±)-3-(2-Phenylethylthio)-4-(1-azabicyclo[2.2.2]octyl-3-oxy)-1,2,5-thiadiazole, (±)-3-(2-Phenyloxyethylthio)-4-(1-azabicyclo[2.2.2] octyl-3-oxy)-1,2,5-thiadiazole, Endo-3-butyloxy-4-(N-methyl-8-azabicyclo[3.2.1]octyl-3-oxy)-1,2,5-thiadiazole, (±)-Exo-3-butyloxy-4-(6-(N-methyl-8-azabicyclo [3.2.1] octan-3-onoxy))-1,2,5-thiadiazole, (±)-Exo-3-chloro-4-(1-azabicyclo[3.2.1]octyl-6-oxy)-1,2,5-thiadiazole, (±)-Endo-3-chloro-4-(1-azabicyclo[3.2.1]octyl-6-oxy)-1,2,5-thiadiazole, (±)-Endo-3-(4-cyanobenzylthio)-4-(1-azabicyclo[3.2.1] octyl-6-oxy)-1,2,5-thiadiazole, 3-Butyloxy-4-(3-azetidinyloxy)-1,2,5-thiadiazole,
3-Butylthio-4-(3-azetidinyloxy)-1,2,5-thiadiazole,
(±)-Trans-3-butyloxy-4-(2-dimethylaminocyclopentyloxy)-1,2,5-thiadiazole,
(±)-3-Butylthio-4-(3-pyrrolidinyloxy)-1,2,5-thiadiazole,
(±)-3-(2-(2-(5-(2-Thienyl) thienyl) thio) ethylthio)-4-(1-azabicyclo[2.2.2]octyl-3-oxy)-1,2,5-thiadiazole,
(±)-3-(2-(5-(2-Thienyl)thienyl)thio)-4-(1-azabicyclo[2.2.2]octyl-3-oxy)-1,2,5-thiadiazole,
(±)-3-(3-N-(2-Thiazolidonyl)propylthio)-4-(1-azabicyclo[2.2.2]octyl-3-oxy)-1,2,5-thiadiazole,
(±)3-Butylthio-4-(exo-2-azabicyclo[2.2.2]oct-6-yloxy)-1,2,5-thiadiazole,
(±)3-(2,2,3,3,4,4,4-heptafluorobutyloxy)-4- [-3-(1-azabicyclo[2.2.2]octyloxy) ]-1,2,5-thiadiazole,
(±)3-(1-butylthio)-4-[endo-6-(1-azabicyclo[3.2.1]octyloxy)]-1,2,5-thiadiazole,
(±)3-(3-phenylpropylthio)-4-[endo-6-(1-azabicyclo-[3.2.1]octyloxy)]-1,2,5-thiadiazole
(±)3-[3-(4-fluorophenyl)propylthio]-4-[-3-(1-azabicyclo-[2.2.2]octyloxy)]-1,2,5-thiadiazole
(±)3-{3-[4-(trifluoromethyl)phenyl]propylthio}-4-[-3-(1-azabicyclo[2.2.2]octyloxy)]-1,2,5-thiadiazole; and
(±)3-(1-Butylamino)-4-[-3-(1-azabicyclo[2.2.2]octyloxy)]-1,2,5-thiadiazole; and
(±)-3-(2-Methylthioethyl)-4-(1-azabicyclo[2.2.2]octyl-3-oxy)-1,2,5-thiadiazole
(±)-3-(1-Azabicyclo[2.2.2]octyl-3-oxy)-1,2,5-thiadiazole
(±)-3-Hexyl-4-(1-azabicyclo[2.2.2]octyl-3-oxy)-1,2,5-thiadiazole
(±)-3-Butylsulfonyl-4-(1-azabicyclo[2.2.2]octyl-3-oxy)-1,2,5-thiadiazole
(±)-3-Propylsulfonyl-4-(1-azabicyclo[2.2.2]octyl-3-oxy)-1,2,5-thiadiazole
(±)-3-(4,4,4-Trifluorobutyloxy)-4-(1-azabicyclo[2.2.2]octyl-3-oxy)-1,2,5-thiadiazole
(±)-3-(2-Butynyloxy)-4-(1-azabicyclo[2.2.2]octyl-3-oxy)-1,2,5-thiadiazole
(±)-3-(Cyclopropylmethoxy)-4-(1-azabicyclo[2.2.2]octyl-3-oxy)-1,2,5-thiadiazole
(±)-3-(3-Phenylpropynyloxy)-4-(1-azabicyclo[2.2.2]octyl-3-oxy)-1,2,5-thiadiazole
(±)-3-(3-Butenyloxy)-4-(1-azabicyclo[2.2.2]octyl-3-oxy)-1,2,5-thiadiazole
(±)-3-(trans-2-Butenyloxy)-4-(1-azabicyclo[2.2.2]octyl-3-oxy)-1,2,5-thiadiazole
(±)-3-(cis-2-Butenyloxy)-4-(1-azabicyclo[2.2.2]octyl-3-oxy)-1,2,5-thiadiazole
(±)-3-(2-Methoxyethoxy)-4-(1-azabicyclo[2.2.2]octyl-3-oxy)-1,2,5-thiadiazole
(±)-3-(2-Phenoxyethoxy)-4-(1-azabicyclo[2.2.2]octyl-3-oxy)-1,2,5-thiadiazole
(±)-3-(3-Butynoxy)-4-(1-azabicyclo[2.2.2)octyl-3-oxy)-1,2,5-thiadiazole
(±)-3-(2-Cyclopropylethoxy)-4-(1-azabicyclo[2.2.2]octyl-3-oxy)-1,2,5-thiadiazole
(±)-3-(2-(Methylthio)ethoxy)-4-(1-azabicyclo[2.2.2]octyl-3-oxy)-1,2,5-thiadiazole
(±)-3-(3-Chloropropoxy)-4-(1-azabicyclo[2.2.2]octyl-3-oxy)-1,2,5-thiadiazole
(±)-3-(4-Fluorobutyloxy)-4-(1-azabicyclo[2.2.2]octyl-3-oxy)-1,2,5-thiadiazole (±)-3-(2-[4-Chlorophenoxy]ethoxy)-4-(1-azabicyclo[2.2.2]octyl-3-oxy)-1,2,5-thiadiazole
(±)-3-(3-[2-methoxy-5-pyridyl]propyloxy)-4-(1-azabicyclo[2.2.2]octyl-3-oxy)-1,2,5-thiadiazole
(±)-3-(trans-3-Chloro-2-propenyloxy)-4-(1-azabicyclo[2.2.2]octyl-3-oxy)-1,2,5-thiadiazole
(±)-3-(2-[4-Fluorophenoxy]ethoxy)-4-(1-azabicyclo[2.2.2]octyl-3-oxy)-1,2,5-thiadiazole
(±)-3-(4-Pentenyloxy)-4-(1-azabicyclo[2.2.2]octyl-3-oxy)-1,2,5-thiadiazole
(±)-3-(3-Fluoropropyloxy)-4-(1-azabicyclo[2.2.2]octyl-3-oxy)-1,2,5-thiadiazole
(±)-3-(Cyclobutylmethoxy)-4-(1-azabicyclo[2.2.2]octyl-3-oxy)-1,2,5-thiadiazole
(±)-3-(3,3,3,2,2-Pentafluoropropyloxy)-4-(1-azabicyclo[2.2.2]octyl-3-oxy)-1,2,5-thiadiazole
(±)-3-(2-[Phenylthio]ethoxy)-4-(1-azabicyclo[2.2.2]octyl-3-oxy)-1,2,5-thiadiazole
(±)-3-(2-[1-napthyloxy]ethoxy)-4-(1-azabicyclo[2.2.2]octyl-3-oxy)-1,2,5-thiadiazole
(±)-3-(2-[4-Bromophenoxy]ethoxy)-4-(1-azabicyclo[2.2.2]octyl-3-oxy)-1,2,5-thiadiazole
(±)-3-(2-Hydroxyethoxy)-4-(1-azabicyclo[2.2.2]octyl-3-oxy)-1,2,5-thiadiazole
3-Butylthio-4-hydroxy-1,2,5-thiadiazole
(±)Exo-3-Butylthio-4-(1-azabicyclo[2.2.1]heptyl-3-oxy)-1,2,5-thiadiazole
(±)-3-(2- [3-{1, 2, 5-Thiadiazoyloxy}]ethoxy)-4-(1-azabicyclo[2.2.2]octyl-3-oxy)-1,2,5-thiadiazole
(±)-exo-3-Butyloxy-4-(7-azabicyclo[2.2.1]heptyl-3-oxy)-1,2,5-thiadiazole
(±)-3-Butyloxy-4-(3-piperidinyloxy)-1,2,5-thiadiazole
3-Butyloxy-4-(cis-1R-2-aminocyclopentanoxy)-1,2,5-thiadiazole
(±)-endo-3-Hexyloxy-4-(1-azabicyclo[3.2.1]octyl-6-oxy)-1,2,5-thiadiazole
(5S,6S)-endo-3-Butylthio-4-(1-azabicyclo[3.2.1]octyl-6-oxy)-1,2,5-thiadiazole
(5R, 6R)-endo-3-Butylthio-4-(1-azabicyclo[3.2.1]octyl-6-oxy)-1,2,5-thiadiazole
(±)-trans-3-Butylthio-4-(1-azabicyclo[4.3.0]nonyl-5-oxy)-1,2,5-thiadiazole
(±)-cis-3-Butylthio-4-(1-azabicyclo[4.3.0]nonyl-5-oxy)-1,2,5-thiadiazole
(±)-trans-3-Butylthio-4-(2-dimethylaminocyclopentyloxy)-1,2,5-thiadiazole
3-Butylthio-4-(2-dimethylaminoethoxy)-1,2,5-thiadiazole
(±)-trans-3-Butylthio-4-(N-tert-butylcarboxy-4-hydroxy-pyrollidin-3-oxy)-1,2,5-thiadiazole
(±)-trans-3-Butylthio-4-(4-hydroxy-pyrollidin-3-oxy)-1,2,5-thiadiazole
(±)-endo-3-Butyloxy-4-(1-azabicyclo [3.2.1]octyl-6-oxy)-1,2,5-thiadiazole
(±)-3-(4-Phenylbutylthio)-4-(1-azabicyclo[2.2.2]octyl-3-oxy)-1,2,5-thiadiazole
(±)-3-(3-Phenyl-2-propenylthio)-4-(1-azabicyclo[2.2.2]octyl-3-oxy)-1,2,5-thiadiazole
(±)-3-(3-[4-Fluorophenyl]propan-3-onethio)-4-(1-azabicyclo[2.2.2]octyl-3-oxy)-1,2,5-thiadiazole
(±)-3-(3-[N-Phenothiazinyl]propylthio)-4-(1-azabicyclo[2.2.2]octyl-3-oxy)-1,2,5-thiadiazole (±)-3-(3-[4-Fluorophenyl]-3-[4-fluorophenoxy]
 propylthio)-4-(1-azabicyclo[2.2.2]octyl-3-oxy)-1,2,5-
 thiadiazole
(±)-3-(3-Phenyl-3-[4-trifluoromethylphenoxy]
 propylthio)-4-(1-azabicyclo[2.2.2]octyl-3-oxy)-1,2,5-
 thiadiazole
(±)-3-(4,4,4-Trifluorobutylthio)-4-(1-azabicyclo[2.2.2]
 octyl-3-oxy)-1,2,5-thiadiazole
(±)-3-(3-[3-Pyridyl]propylthio)-4-(1-azabicyclo[2.2.2]
 octyl-3-oxy)-1,2,5-thiadiazole
(±)-endo-3-(2-Phenoxyethylthio)-4-(1-azabicyclo[3.2.1]
 octyl-6-oxy)-1,2,5-thiadiazole
(±)-exo-3-Propythio-4-(2-methoxycarbonyl-2-azabicyclo
 [2.2.2]octyl-6-oxy)-1,2,5-thiadiazole
(±)-exo-3-Propylsulfonyl-4-(2-methoxycarbonyl-2-
 azabicyclo[2.2.2]octyl-6-oxy)-1,2,5-thiadiazole
(±)-exo-3-(4,4,4-Trifluorobutyloxy)-4-(2-
 methoxycarbonyl-2-azabicyclo[2.2.2]octyl-6-oxy)-1,2,
 5-thiadiazole
(±)-exo-3-(4,4,4-Trifluorobutyloxy)-4-(2-azabicyclo
 [2.2.2]octyl-6-oxy)-1,2,5-thiadiazole
(±)-exo-3-(Hexyloxy)-4-(2-azabicyclo[2.2.2]octyl-6-
 oxy)-1,2,5-thiadiazole
(±)-endo-3-(4,4,4-Trifluorobutyloxy)-4-(2-azabicyclo
 [2.2.2]octyl-6-oxy)-1,2,5-thiadiazole
(±)-exo-3-(2-[Fluorophenoxy]ethylthio)-4-(2-
 methoxycarbonyl-2-azabicyclo[2.2.2]octyl-6-oxy)-1,2,
 5-thiadiazole
(±)-exo-3-(2-[Fluorophenoxy]ethylthio)-4-(2-azabicyclo
 [2.2.2]octyl-6-oxy)-1,2,5-thiadiazole
(±)-endo-3-Propylthio-4-(1-azabicyclo[3.2.1]octyl-6-
 oxy)-1,2,5-thiadiazole
(±)-endo-3-Propylsulfonyl-4-(1-azabicyclo[3.2.1]octyl-
 6-oxy)-1,2,5-thiadiazole
(±)-endo-3-(4,4,4-Trifluorobutoxy)-4-(1-azabicyclo
 [3.2.1]octyl-6-oxy)-1,2,5-thiadiazole
(±)-endo-3-(2-Butynyloxy)-4-(1-azabicyclo[3.2.1]octyl-
 6-oxy)-1,2,5-thiadiazole
(±)-endo-3-(trans-2-Butenyloxy)-4-(1-azabicyclo[3.2.1]
 octyl-6-oxy)-1,2,5-thiadiazole
(±)-endo-3-(2-Methylthioethoxy)-4-(1-azabicyclo[3.2.1]
 octyl-6-oxy)-1,2,5-thiadiazole
(±)-endo-3-(2-(4-Methyl-1,3-thiazol-5-yl)ethoxy)-4-(1-
 azabicyclo[3.2.1]octyl-6-oxy)-1,2,5-thiadiazole
(±)-endo-3-(4-Methylthiobenzyloxy)-4-(1-azabicyclo
 [3.2.]octyl-6-oxy)-1,2,5-thiadiazole
(±)-endo-3-(2-Thienylmethoxy)-4-(1-azabicyclo[3.2.1]
 octyl-6-oxy)-1,2,5-thiadiazole
(±)-endo-3-(2-Cyclohexenyloxy)-4-(1-azabicyclo[3.2.1]
 octyl-6-oxy)-1,2,5-thiadiazole
(±)-endo-3-(3-Pentynyloxy)-4-(1-azabicyclo[3.2.1]octyl-
 6-oxy)-1,2,5-thiadiazole
(±)-endo-3-(3-Hexynyloxy)-4-(1-azabicyclo[3.2.1]octyl-
 6-oxy)-1,2,5-thiadiazole
(±)-endo-3-(3-Chloropropoxy)-4-(1-azabicyclo[3.2.1]
 octyl-6-oxy)-1,2,5-thiadiazole
(±)-endo-3-[2-(2-Napthalyl)ethoxy]-4-(1-azabicyclo
 [3.2.1]octyl-6-oxy)-1,2,5-thiadiazole
(±)-endo-3-(4-Chloro-α-cyclopropyl-benzyloxy)-4-(1-
 azabicyclo[3.2.1]octyl-6-oxy)-1,2,5-thiadiazole
(±)-endo-3-(4-Methyl-3-pentenyloxy)-4-(1-azabicyclo
 [3.2.1]octyl-6-oxy)-1,2,5-thiadiazole
(±)-endo-3-(cis-2-Butenyloxy)-4-(1-azabicyclo[3.2.1]
 octyl-6-oxy)-1,2,5-thiadiazole
(±)-endo-3-(Cyclopropylmethoxy)-4-(1-azabicyclo
 [3.2.1]octyl-6-oxy)-1,2,5-thiadiazole
(±)-endo-3-(2-Methoxyethoxy)-4-(1-azabicyclo[3 .2.1]
 octyl-6-oxy)-1,2,5-thiadiazole
(±)-endo-3-(3-Butenyloxy)-4-(1-azabicyclo[3.2.1]octyl-
 6-oxy)-1,2,5-thiadiazole
(±)-endo-3-(2-cyclopropylethoxy)-4-(1-azabicyclo
 [3.2.1]octyl-6-oxy)-1,2,5-thiadiazole
(±)-endo-3-(3-Butynyloxy)-4-(1-azabicyclo[3.2.1]octyl-
 6-oxy)-1,2,5-thiadiazole
(±)-endo-3-(4,4,4,3,3,2,2-Heptafluorobutoxy)-4-(1-
 azabicyclo[3.2.1]octyl-6-oxy)-1,2,5-thiadiazole
(±)-endo-3-[2-(3-Trifluoromethylphenyl)ethoxy]-4-(1-
 azabicyclo[3.2.1]octyl-6-oxy)-1,2,5-thiadiazole
(±)-endo-3-[2-(2-Thienyl)ethoxy]-4-(1-azabicyclo[3.2.1]
 octyl-6-oxy)-1,2,5-thiadiazole
(±)-endo-3-(3,3,3,2,2,Pentafluoropropoxy)-4-(1-
 azabicyclo[3.2.1]octyl-6-oxy)-1,2,5-thiadiazole
(±)-endo-3-(2-Phenoxyethoxy)-4-(1-azabicyclo[3.2.1]
 octyl-6-oxy)-1,2,5-thiadiazole
(±)-endo-3-(4-n-Butylbenzyloxy)-4-(1-azabicyclo [3.2.1]
 octyl-6-oxy)-1,2,5-thiadiazole
(±)-endo-3- [3-(4-Methoxyphenyl)propoxy]-4-(1-
 azabicyclo[3.2.1]octyl-6-oxy)-1,2,5-thiadiazole
(±)-endo-3-(4-Fluorobenzyloxy)-4-(1-azabicyclo [3.2.1]
 octyl-6-oxy)-1,2,5-thiadiazole
(±)-endo-3-(2,4-Difluorobenzyloxy)-4-(1-azabicyclo
 [3.2.1]octyl-6-oxy)-1,2,5-thiadiazole
(±)-endo-3-[4-(Trifluoromethoxy)benzyloxy]-4-(1-
 azabicyclo[3.2.1]octyl-6-oxy)-1,2,5-thiadiazole
(±)-endo-3-(4-Fluorobutoxy)-4-(1-azabicyclo[3.2.1]
 octyl-6-oxy)-1,2,5-thiadiazole
(±)-endo-3-(4-tert-Butylbenzyloxy)-4-(1-azabicyclo
 [3.2.1]octyl-6-oxy)-1,2,5-thiadiazole
(±)-endo-3-(1-Cyclopropylethoxy)-4-(1-azabicyclo
 [3.2.1]octyl-6-oxy)-1,2,5-thiadiazole
(±)-endo-3-(2-Cyclohexylethoxy)-4-(1-azabicyclo[3.2.1]
 octyl-6-oxy)-1,2,5-thiadiazole
(±)-endo-3-(3-Methyl-2-butenyloxy)-4-(1-azabicyclo
 [3.2.1]octyl-6-oxy)-1,2,5-thiadiazole
(±)-endo-3-(4-Cyclohexylbutoxy)-4-(1-azabicyclo[3.2.1]
 octyl-6-oxy)-1,2,5-thiadiazole
(±)-endo-3-(3-Butyn-2-oxy)-4-(1-azabicyclo[3.2.1]octyl-
 6-oxy)-1,2,5-thiadiazole
(±)-endo-3-(3-Methyl-3-phenylbutoxy)-4-(1-azabicyclo
 [3.2.1]octyl-6-oxy)-1,2,5-thiadiazole
(±)-endo-3-(3-Fluoropropoxy)-4-(1-azabicyclo[3.2.1]
 octyl-6-oxy)-1,2,5-thiadiazole
(±)-endo-3-[3-(2-Thienyl)propoxy]-4-(1-azabicyclo
 [3.2.1]octyl-6-oxy)-1,2,5-thiadiazole
(±)-3-(2-[4-Fluorophenoxy]ethylthio)-4-(1-azabicyclo
 [2.2.2]octyl-3-oxy)-1,2,5-thiadiazole
(±)-3-(2-Methylthioethyl)-4-(1-azabicyclo[2.2.2]octyl-3-
 oxy)-1,2,5-thiadiazole
(±)-3-(1-Azabicyclo[2.2.2]octyl-3-oxy)-1,2,5-thiadiazole
(±)-3-Hexyl-4-(1-azabicyclo[2.2.2]octyl-3-oxy)-1,2,5-
 thiadiazole
3-Butylthio-4-hydroxy-1,2,5-thiadiazole
(±)-3-(2-[3-{1,2,5-Thiadiazoyloxy}]ethoxy)-4-(1-
 azabicyclo[2.2.2]octyl-3-oxy)-1,2,5-thiadiazole (+/−)-3-butylthio-4-(azabicyclo[2.2.2]octyl-3-oxy)-1,2,5-oxadiazole, (+/−)-3-(2-butyloxy)-4-[(+/−)-3-azabicyclo[2.2.2]octyloxy)-1,2,5-oxadiazole, (+/−)-3-butyloxy-4-[endo-(+/−)-6-[1-azabicyclo[3.2.1]octyloxy)]-1,2,5-oxadiazole, 3-(2,2,3,3,4,4,4-heptaflurorobutyloxy)-4-[(+/−)-3-(1-azabicyclo[2.2.2]octyloxy)]-1,2,5-oxadiazole, 3-methoxy-4-(1-azabicyclo[2.2.2]octyl-3-oxy)-1,2,5-oxadiazole, 3-pentylthio-4-(1-azabicyclo[2.2.2]ocytl-3-oxy)-1,2,5-oxadiazole, trans-3-butyloxy-4-(2-dimethylaminocyclopentyloxy)-1,2,5-oxadiazole, 3-butylthio-4-(3-azetidinyloxy)-1,2,5-oxadiazole, 3-(3-N-(2-thiazolidonyl)propylthio)-4-(1-azabicyclo[2.2.2]octyl-3-oxy)-1,2,5-oxadiazole, 3-chloro-4-(1-azabicyclo[3.2.1]octyl-6-oxy)-1,2,5-oxadiazole, 3-(2-2-thio-5-trifluoromethylthienyl)ethylthio)-4-azabicyclo[2.2.2]octyl-3-oxy)-1,2,5-oxadiazole, 3-butylthio-4-[3-±-endo-(1-azabicyclo[2.2.1]heptyloxy)]-1,2,5-oxadiazole, 3-hexyloxy-4-[6-±-endo-(2-azabicyclo[2.2.2]ocyloxy)]-1,2,5-oxadiazole, 3-(4,4,4-trifluorobutylthio)-4-[2-+-exo-(7-azabicyclo[2.2.1]heptyloxy)]-1,2,5-oxadiazole, 3-(2-phenoxyethylthio)-4-[3-±-endo-(1-azabicyclo[3.2.1]octyloxy)]- 1,2,5-oxadiazole, 3-(5-hexenyloxy)-4-[7-+-endo-(2-azabicyclo[2.2.1]heptyloxy)]-1,2,5-oxadiazole, 3-butyl-4-[5-(1-azabicyclo[3.2.1]octyloxy)]-1,2,5-oxadiazole, 3-cyclobutylmethyl-4-[2-±-endo-(8-azabicyclo[3.2.1]octyloxy)]-1,2,5-oxadiazole, (+/−)-3-butylthio-4-(azabicyclo[2.2.2]octyl-3-oxy)-pyrazine, (+/−)-3-(2-butyloxy)-4-[(+/−)-3-azabicyclo[2.2.2]octyloxy)pyrazine, (+/−)-3-butyloxy-4-[endo-(+/−)-6-[1-azabicyclo[3.2.1]octyloxy)]-pyrazine, 3-(2,2,3,3,4,4,4-heptaflurorobutyloxy)-4-[(+/−)-3-(1-azabicyclo[2.2.2]octyloxy)]-pyrazine, 3-methoxy-4-(1-azabicyclo[2.2.2]octyl-3-oxy)-pyrazine, 3-pentylthio-4-(1-azabicyclo[2.2.2]ocytl-3-oxy)-pyrazine, trans-3-butyloxy-4-(2-dimethylaminocyclopentyloxy)-pyrazine, 3-butylthio-4-(3-azetidinyloxy)-pyrazine, 3-(3-N-(2-thiazolidonyl)propylthio)-4-(1-azabicyclo[2.2.2]octyl-3-oxy)-pyrazine, 3-chloro-4-(1-azabicyclo[3.2.1]octyl-6-oxy)-pyrazine, 3-(2-2-thio-5-trifluoromethylthienyl)ethylthio)-4-azabicyclo[2.2.2]octyl-3-oxy)-pyrazine, 3-butylthio-4-[3-±-endo-(1-azabicyclo[2.2.1]heptyloxy)]-pyrazine, 3-hexyloxy-4-[6-±-endo-(2-azabicyclo[2.2.2]ocyloxy)]-pyrazine, 3-(4,4,4-trifluorobutylthio)-4-[2-±-exo-(7-azabicyclo[2.2.1]heptyloxy)]-pyrazine, 3-(2-phenoxyethylthio)-4-[3-±-endo-(1-azabicyclo[3.2.1]octyloxy)]-pyrazine, 3-(5-hexenyloxy)-4-[7-±-endo-(2-azabicyclo[2.2.1]heptyloxy)]-pyrazine, 3-butyl-4-[5-(1-azabicyclo[3.2.1]octyloxy)]-pyrazine, and 3-cyclobutylmethyl-4-[2-+-endo-(8-azabicyclo[3.2.1]octyloxy)]-pyrazine, 2-[exo-(+/−)-3-[1-azabicyclo[3.2.1]octyloxy)]pyrazine, 3-butylthio-2-(1-azabicyclo[2.2.2]ocytl-3-oxy)]pyrazine, 3-butyloxy-2-[3-±-endo-(1-azabicyclo[2.2.1]heptyloxy)]pyrazine, 3-(2-butynyloxy)-2-[6-±-endo-(1-azabicyclo[3.2.1]octyloxy)]pyrazine, 3-hexylthio-2-[6-±-exo-(2-azabicyclo[2.2.1]heptyloxy)]pyrazine, 3-(3-phenylpropynylthio)-2-[2-+-exo-(7-azabicyclo[2.2.1]heptyloxy)]pyrazine, 3-(2-methylthioethoxy)-2-[3-+-exo-(1-azabicyclo[3.2.1]octyloxy)]pyrazine, 3-propargyl- 2-[4-(1-azabicyclo[2.2.1]heptyloxy)]pyrazine, and 3-cyclopropylmethylthio-2-[2-±-exo-(8-azabicyclo[3.2.1]octyloxy)]pyrazine; or a pharmaceutically acceptable salt thereof.

12. A composition as claimed by claim 8 wherein the opioid is selected from the group consisting of morphine, codeine, meperidine, methadone, propoxyphene, levorphanol, hydromorphone, oxymorphone, oxycodone, brompton's cocktail, naloxone, naltrexone, pentazocine, butorphanol, nabuphine, and buprenorphine.

13. A composition as claimed by claim 8 wherein the opioid is selected from the group consisting of hydromorphone, hydrocodone, meperidone, buprenorphine, butorphenol, nalbuphine, pentazocine, oxymorphine, oxycodone, levorphanol, fentanyl, and alphaprodine.

14. A composition as claimed by claim 8 wherein the opioid is selected from the group consisting of propoxyphene, methadone, hydrocodone, hydromorphine, and codeine.

15. A composition as claimed by claim 1 wherein the Synergistic Analgesic is acetaminophen.

16. A composition as claimed by claim 15 wherein the First Compound is selected from the group consisting of Formula I and Formula I$^{1'}$; or a pharmaceutically acceptable salt or solvate thereof.

17. A composition as claimed by claim 15 wherein the First Compound is Formula II; or a pharmaceutically acceptable salt thereof.

18. A composition as claimed by claim 1 wherein the Synergistic Analgesic is an alpha-adrenergic compound.

19. A composition as claimed by claim 18 wherein the First Compound is selected from the group consisting of Formula I and Formula I$^{1'}$; or a pharmaceutically acceptable salt or solvate thereof.

20. A composition as claimed by claim 19 wherein the First Compound is Formula I'; or a pharmaceutically acceptable salt thereof.

21. A method for treating pain comprising administering an analgesic dose of a composition comprising a a First Compound selected from the group consisting of:

Formula I

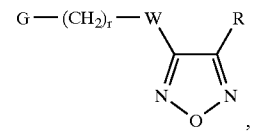

Formula I'

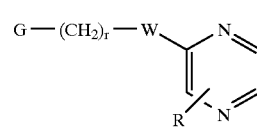

wherein

W is oxygen or sulphur;

R is hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl) $-Z-C_{3-10}$-cycloalkyl and $-Z-C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $-CF_3$, $-CN$, Y, phenyl or phenoxy wherein phenyl or phenoxy is optionally substituted with halogen, $-CN$, $C_{1-4}$-alkyl, $C_{1-4}$-alkoxy, $-OCF_3$, $-CF_3$, $-CONH_2$ or $-CSNH_2$; or R is phenyl or benzyloxycarbonyl, each of which is optionally substituted with halogen, —CN, $C_{1-4}$-alkyl, $C_{1-4}$-alkoxy, —OCF$_3$, —CF$_3$, —CONH$_2$ or —CSNH$_2$; or R is —OR$^5$Y, —SR$^5$Y, OR$^5$—Z—Y, —SR$^5$ZY, —O—R$^5$—Z—R$^4$ or —S—R$^5$—Z—R$^4$ wherein Z is oxygen or sulphur, R$^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

het-1
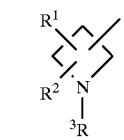

het-2
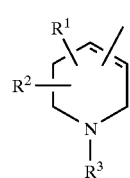

het-3
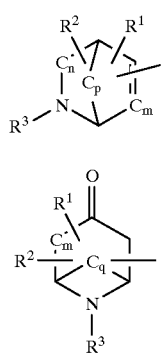

het-4 het-5
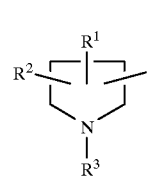

het-6
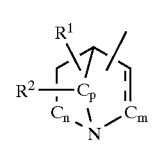
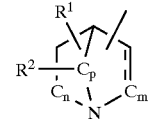

het-7
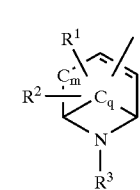

or G can optionally be substituted $C_3$–$C_8$ cycloalkyl or optionally substituted $C_{1-6}$-alkyl wherein the substitution is —NR$^6$R$^7$;

R$^6$ and R$^7$ independently are hydrogen, $C_{1-6}$-alkyl; or R$^6$ and R$^7$ together with the nitrogen atom optionally form a 4- to 6-member ring;

R$^1$ and R$^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —COR$^{6'}$, CH$_2$—OH, halogen, —NH$_2$, carboxy, or phenyl;

R$^3$ is hydrogen, $C_{1-5}$-alkyl, $C_{2-5}$-alkenyl or $C_{2-5}$-alkynyl;

R$^{6'}$ is hydrogen, $C_{1-6}$-alkyl;

n is 0, 1 or 2;

m is 0, 1 or 2;

p is 0, 1 or 2;

q is 1 or 2;

r is 0, 1 or 2;

...... is a single or double bond; and

Formula I$^{1'}$

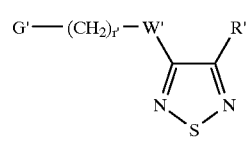
(I$^{1'}$)

wherein

W' is oxygen or sulfur;

R' is hydrogen, amino, halogen, NHR6', NR$^{6'}$R$^{7'}$, R$^{4'}$, —OR$^{4'}$, —SR$^{4'}$, —SOR$^{4'}$, —SO$_2$R$^{4'}$, $C_{3-10}$-cycloalkyl, $C_{4-12}$-(cycloalkylalkyl), —Z'-$C_{3-10}$-cycloalkyl and —Z'-$C_{4-12}$-(cycloalkylalkyl) wherein R$^{4'}$ is $C_{1-5}$-alkyl, $C_{2-15}$-alkenyl, $C_{2-15}$-alkynyl, each of which is optionally substituted with one or more halogen(s), —CF$_3$, —CN, Y', phenyl or phenoxy wherein phenyl or phenoxy is optionally substituted with halogen, —CN, $C_{1-4}$-alkyl, $C_{1-4}$-alkoxy, —OCF$_3$, —CF$_3$, —CONH$_2$ or —CSNH$_2$; or R' is phenyl or benzyloxycarbonyl, each of which is optionally substituted with halogen, —CN, $C_{1-4}$-alkyl, $C_{1-4}$-alkoxy, —OCF$_3$, —CF$_3$, —CONH$_2$ or —CSNH$_2$; or R' is —OR$^{5'}$Y', —SR$^{5'}$Y', OR$^5$—Z'—Y', —SR$^5$Z'Y', —O—R$^{5'}$—Z—R$^{4'}$ or —S—R$^5$—Z'—R$^{4'}$ wherein Z' is oxygen or sulphur, R$^{5'}$ is $C_{1-15}$-alkyl, $C_{2-15}$-alkenyl, $C_{2-15}$-alkynyl, and Y' is a 5 or 6 membered heterocyclic group; and G' is selected from one of the following azacyclic or azabicyclic ring systems:

het-1
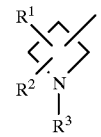

het-2
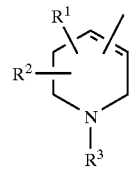

-continued

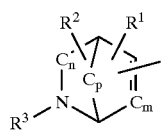
het-3

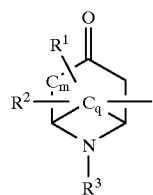
het-4

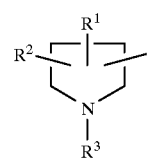
het-5

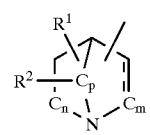
het-6

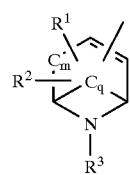
het-7 or G' can optionally be substituted $C_3$–$C_8$ cycloalkyl or optionally substituted $C_{1-6}$-alkyl wherein the substitution is —$NR^{6'}R^{7'}$;

$R^{6'}$ and $R^{7'}$ independently are hydrogen, $C_{1-6}$-alkyl; or $R^{6'}$ and $R^{7'}$ together with the nitrogen atom optionally form a 4- to 6-member ring;

$R^1$ and $R^2$ independently are hydrogen, $C_{1-5}$-alkyl, $C_{2-5}$-alkenyl, $C_{2-5}$-alkynyl, $C_{1-10}$-alkoxy, $C_{1-5}$-alkyl substituted with —OH, —$COR^{6''}$, $CH_2$—OH, halogen, —$NH_2$, carboxy, or phenyl;

$R^3$ is hydrogen, $C_{1-5}$-alkyl, $C_{2-5}$-alkenyl or $C_{2-5}$-alkynyl;

$R^{6''}$ is hydrogen, $C_{1-15}$-alkyl n is 0, 1 or 2;

m is 0, 1 or 2;

p is 0, 1 or 2;

q is 1 or 2;

r is 0, 1 or 2;

....... is a single or double bond; or a pharmaceutically acceptable salt or solvate thereof;

and one or more Synergistic Analgesics in a weight ratio of First Compound to Synergistic Analgesic of from about 1 to about 1000.

22. A method as claimed by claim 21 wherein the First Compound is selected from the group consisting of Formula I and Formula I$^{1'}$; or a pharmaceutically acceptable salt or solvate thereof.

23. A method as claimed by claim 21 wherein the Synergistic Analgesic is a nonsteroidal anti-inflammatory drug.

24. A method as claimed by claim 23 wherein the nonsteroidal anti-inflammatory drug is selected from the group consisting of indomethacin, ibuprofen, naproxen, fenoprofen, tolmetin, sulindac, meclofenamate, keoprofen, piroxicam, flurbiprofen, and diclofenac.

25. A method as claimed by claim 23 wherein the nonsteroidal anti-inflammatory drug is ibuprofen.

26. A method as claimed by claim 23 wherein the First Compound is selected from the group consisting of Formula I and Formula I$^{1'}$; or a pharmaceutically acceptable salt or solvate thereof.

27. A method as claimed by claim 21 wherein the Synergistic Analgesic is an opioid.

28. A method as claimed by claim 27 wherein the First Compound is selected from the group consisting of Formula I and Formula I$^{1'}$; or a pharmaceutically acceptable salt or solvate thereof.

29. A method as claimed by claim 27 wherein the First Compound is Formula I'; or a pharmaceutically acceptable salt thereof.

30. A method as claimed by claim 27 wherein the opioid is selected from the group consisting of morphine, codeine, meperidine, methadone, propoxyphene, levorphanol, hydromorphone, oxymorphone, oxycodone, brompton's cocktail, naloxone, naltrexone, pentazocine, butorphanol, nabuphine, and buprenorphine.

31. A method as claimed by claim 27 wherein the opioid is selected from the group consisting of hydromorphone, hydrocodone, meperidone, buprenorphine, butorphenol, nalbuphine, pentazocine, oxymorphine, oxycodone, levorphanol, fentanyl, and alphaprodine.

32. A method as claimed by claim 27 wherein the opioid is selected from the group consisting of propoxyphene, methadone, hydrocodone, hydromorphine, and codeine.

33. A method as claimed by claim 21 wherein the Synergistic Analgesic is acetaminophen.

34. A method as claimed by claim 33 wherein the First Compound is selected from the group consisting of Formula I and Formula I$^{1'}$; or a pharmaceutically acceptable salt or solvate thereof.

35. A method as claimed by claim 21 wherein the Synergistic Analgesic is an alpha-adrenergic compound.

36. A method as claimed by claim 35 wherein the First Compound is selected from the group consisting of Formula I and Formula I$^{1'}$; or a pharmaceutically acceptable salt or solvate thereof.

37. The use of a First Compound selected from the group consisting of:

Formula I

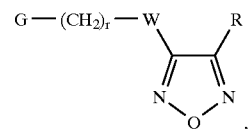

I

-continued

Formula I'

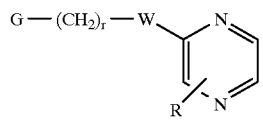

wherein

W is oxygen or sulphur;

R is hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl) $-Z-C_{3-10}$-cycloalkyl and $-Z-C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $-CF_3$, $-CN$, Y, phenyl or phenoxy wherein phenyl or phenoxy is optionally substituted with halogen, $-CN$, $C_{1-4}$-alkyl, $C_{1-4}$-alkoxy, $-OCF_3$, $-CF_3$, $-CONH_2$ or $-CSNH_2$; or R is phenyl or benzyloxycarbonyl, each of which is optionally substituted with halogen, $-CN$, $C_{1-4}$-alkyl, $C_{1-4}$-alkoxy, $-OCF_3$, $-CF_3$, $-CONH_2$ or $-CSNH_2$; or R is $-OR^5Y$, $-SR^5Y$, $OR^5-Z-Y$, $-SR^5ZY$, $-O-R^5-Z-R^4$ or $-S-R^5-Z-R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

het-1

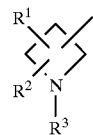

het-2

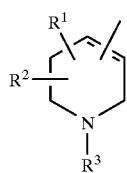

het-3

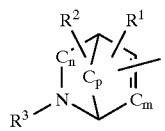

het-4

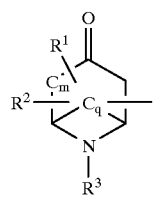

het-5

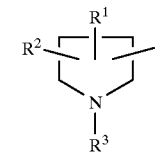

het-6

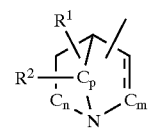

het-7

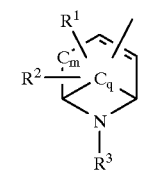

or G can optionally be substituted $C_3$–$C_8$ cycloalkyl or optionally substituted $C_{1-6}$-alkyl wherein the substitution is $-NR^6R^7$;

$R^6$ and $R^7$ independently are hydrogen, $C_{1-6}$-alkyl; or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with $-OH$, $-COR^{6'}$, $CH_2-OH$, halogen, $-NH_2$, carboxy, or phenyl;

$R^3$ is hydrogen, $C_{1-5}$-alkyl, $C_{2-5}$-alkenyl or $C_{2-5}$-alkynyl;

$R^{6'}$ is hydrogen, $C_{1-6}$-alkyl;

n is 0, 1 or 2;

m is 0, 1 or 2;

p is 0, 1 or 2;

q is 1 or 2;

r is 0, 1 or 2;

is a single or double bond; and

Formula I<sup>1'</sup>

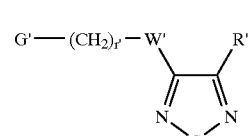

wherein

W' is oxygen or sulfur;

$R^1$ is hydrogen, amino, halogen, NHR6', $NR^{6'}R^{7''}$, $R^{4''}$, $-OR^{4'}$, $-SR^{4'}$, $-SOR^{4'}$, $-SO_2R^{4'}$, $C_{3-10}$-cycloalkyl, $C_{4-12}$-(cycloalkylalkyl), $-Z'-C_{3-10}$-cycloalkyl and $-Z'-C_{4-12}$-(cycloalkylalkyl) wherein $R^{4'}$ is $C_{1-15}$-alkyl, $C_{2-15}$-alkenyl, $C_{2-15}$-alkynyl, each of which is optionally substituted with one or more halogen(s), $-CF_3$, $-CN$, Y', phenyl or phenoxy wherein phenyl or phenoxy is optionally substituted with halogen, $-CN$, $C_{1-4}$-alkyl, $C_{1-4}$-alkoxy, $-OCF_3$, $-CF_3$, $-CONH_2$ or $-CSNH_2$; or R' is phenyl or benzyloxycarbonyl, each of which is optionally substituted with halogen, $-CN$, $C_{14}$-alkyl, $C_{1-4}$-alkoxy, $-OCF_3$, $-CF_3$, $-CONH_2$ or $-CSNH_2$; or R' is —OR⁵'Y', —SR⁵'Y', OR⁵'—Z'—Y', —SR⁵'Z'Y', —O—R⁵'—Z—R⁴'or —S—R⁵—Z'—R⁴' wherein Z' is oxygen or sulphur, R⁵' is $C_{1-15}$-alkyl, $C_{2-15}$-alkenyl, $C_{2-15}$-alkynyl, and Y' is a 5 or 6 membered heterocyclic group; and G' is selected from one of the following azacyclic or azabicyclic ring systems:

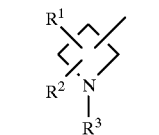

het-1

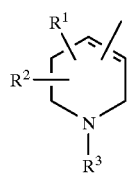

het-2

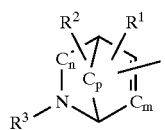

het-3

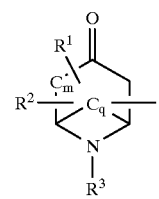

het-4

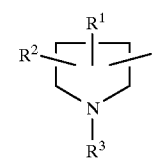

het-5

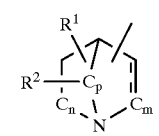

het-6

-continued

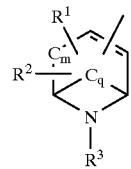

het-7 or G' can optionally be substituted $C_3$–$C_8$ cycloalkyl or optionally substituted $C_{1-6}$-alkyl wherein the substitution is —NR⁶'R⁷';

R⁶' and R⁷' independently are hydrogen, $C_{1-6}$-alkyl; or

R⁶' and R⁷' together with the nitrogen atom optionally form a 4- to 6-member ring;

R¹ and R² independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —COR⁶', $CH_2$—OH, halogen, —$NH_2$, carboxy, or phenyl;

R³ is hydrogen, $C_{1-5}$-alkyl, $C_{2-5}$-alkenyl or $C_{2-5}$-alkynyl;

R⁶' is hydrogen, $C_{1-15}$-alkyl n is 0, 1 or 2;

m is 0, 1 or 2;

p is 0, 1 or 2;

q is 1 or 2;

r is 0, 1 or 2;

....... is a single or double bond; or a pharmaceutically acceptable salt or solvate thereof; and one or more Synergistic Analgesics in a weight ratio of Compound to Synergistic Analgesic of from about 1 to about 1000 for the manufacture of a medicament for therapeutic application in the treatment of pain.

38. A use as claimed by claim 37 wherein the Synergistic Analgesic is an opioid.

39. A use as claimed by claim 37 wherein the Synergistic Analgesic is acetaminophen.

40. A use as claimed by claim 37 wherein the Synergistic Analgesic is a nonsteroidal anti-inflammatory drug.

41. A use as claimed by claim 37 wherein the Synergistic Analgesic is an alpha-adrenergic compound.

* * * * *

UNITED STATES PATENT AND TRADEMARK OFFICE
CERTIFICATE OF CORRECTION

PATENT NO. : 5,998,434

DATED : December 7, 1999

INVENTOR(S) : Charles H. Mitch, et al.

It is certified that error appears in the above-indentified patent and that said Letters Patent is hereby corrected as shown below:

In column 88, line 61, please delete "i-endo-" and insert therefor -- ±-endo- --.

In column 90, line 1, please delete "I-azabicyclo" and insert therefor -- 1-azabicyclo --.

In column 93, line 50, please delete "[3.2.]" and insert therefor -- [3.2.1.] --.

In column 94, line 5, please delete "[3 .2.1]" and insert therefor -- [3.2.1] --.

In column 96, line 23, please delete "Formula II" and insert therefor -- Formula I --.

In column 99, line 44, please delete "$C_{16}$-alkyl" and insert therefor -- $C_{1-6}$-alkyl --.

In column 99, line 50, please delete "$C_{1-5}$-alkyl" and insert therefor -- $C_{1-15}$-alkyl --.

In column 102, line 65, please delete "$C_{14}$-alkyl" and insert therefor -- $C_{1-4}$-alkyl --.

Signed and Sealed this

Third Day of April, 2001

Attest:

NICHOLAS P. GODICI

*Attesting Officer*   Acting Director of the United States Patent and Trademark Office